US009925536B2

(12) United States Patent
Ermantraut et al.

(10) Patent No.: US 9,925,536 B2
(45) Date of Patent: Mar. 27, 2018

(54) ASSAYS FOR MEASURING NUCLEIC ACIDS

(75) Inventors: Eugen Ermantraut, Jena (DE); Thomas Kaiser, Hohlstedt (DE); Torsten Schulz, Jena (DE); Katrin Steinmetzer, Jena (DE); Thomas Ullrich, Jena (DE)

(73) Assignee: CLONDIAG GMBH, Jena (DE)

(*) Notice: Subject to any disclaimer, the term of this patent is extended or adjusted under 35 U.S.C. 154(b) by 621 days.

(21) Appl. No.: 12/670,088

(22) PCT Filed: Jul. 23, 2008

(86) PCT No.: PCT/EP2008/059670
§ 371 (c)(1),
(2), (4) Date: May 28, 2010

(87) PCT Pub. No.: WO2009/013321
PCT Pub. Date: Jan. 29, 2009

(65) Prior Publication Data
US 2010/0255473 A1    Oct. 7, 2010

Related U.S. Application Data

(60) Provisional application No. 60/951,358, filed on Jul. 23, 2007.

(51) Int. Cl.
*B01L 3/00* (2006.01)
*C12Q 1/68* (2018.01)
*C12Q 1/70* (2006.01)

(52) U.S. Cl.
CPC ....... *B01L 3/502738* (2013.01); *B01L 3/5027* (2013.01); *C12Q 1/6816* (2013.01); *C12Q 1/6848* (2013.01); *C12Q 1/703* (2013.01); *C12Q 1/708* (2013.01); *B01L 2300/0816* (2013.01); *B01L 2300/0887* (2013.01); *B01L 2300/18* (2013.01); *B01L 2400/0415* (2013.01); *B01L 2400/0481* (2013.01); *B01L 2400/0655* (2013.01)

(58) Field of Classification Search
None
See application file for complete search history.

(56) References Cited

U.S. PATENT DOCUMENTS

| | | | | |
|---|---|---|---|---|
| 5,501,963 | A * | 3/1996 | Burckhardt | 435/91.2 |
| 5,922,591 | A * | 7/1999 | Anderson et al. | 435/287.2 |
| 5,989,831 | A * | 11/1999 | Cros | C12Q 1/6804 435/7.1 |
| 6,440,725 | B1 * | 8/2002 | Pourahmadi et al. | 435/288.5 |
| 2003/0190608 | A1 | 10/2003 | Blackburn | |
| 2006/0166233 | A1 | 7/2006 | Wu et al. | |
| 2006/0281112 | A1 * | 12/2006 | Remacle | C12Q 1/6834 435/6.12 |
| 2007/0051415 | A1 | 3/2007 | Wang | |
| 2007/0184478 | A1 * | 8/2007 | Gumbrecht | C12Q 1/6837 435/6.16 |
| 2008/0013092 | A1 * | 1/2008 | Maltezos et al. | 356/417 |
| 2008/0057572 | A1 | 3/2008 | Petersen et al. | |
| 2008/0207461 | A1 | 8/2008 | Ermantraut et al. | |

FOREIGN PATENT DOCUMENTS

| | | |
|---|---|---|
| DE | DE 10 2004 022 263 | 12/2005 |
| EP | 0122695 | 10/1984 |
| EP | 0590327 | 4/1994 |
| EP | 0637999 | 2/1995 |
| EP | 1418243 | 5/2004 |
| EP | 1045036 B1 * | 6/2007 |
| JP | H06277062 | 10/1994 |
| JP | 2006516743 | 7/2006 |
| JP | 2010534328 | 11/2010 |
| WO | WO 94/26414 | 1/1994 |
| WO | 97/22825 | 6/1997 |
| WO | WO 01/02094 | 1/2001 |
| WO | 02/053921 | 7/2002 |
| WO | 2004/072097 | 8/2004 |
| WO | WO 2005/108604 | 6/2005 |
| WO | 2005/093388 | 10/2005 |
| WO | 2005/108620 | 11/2005 |
| WO | 2006/007567 | 1/2006 |
| WO | 2006/051088 | 5/2006 |
| WO | 2006132666 | 12/2006 |
| WO | WO 2007/051861 | 5/2007 |
| WO | 2007/066479 | 6/2007 |
| WO | 2007/076549 | 7/2007 |
| WO | 2008/055915 | 5/2008 |
| WO | 2009/013321 | 1/2009 |

OTHER PUBLICATIONS

Liao et al. Nucleic Acids Research (2005) 33(18): e156.*
Deregt et al. Journal of Veterinary Diagnostic Investigation (2002) 14: 433-437.*
Liu et al. Analytical Chemistry (2004) 76: 1824-1831.*
Lyamuya et al. Journal of Clinical Virology (2000) 17(1): 57-63.*
Liao et al. Journal of Clinical Microbiology (2006) 44(2): 561-570.*
Esch et al. Analytical Chemistry (2001) 73: 3162-3167.*
Yuen et al. Genome Research 11: 405-412 (2001).*
U.S. Appl. No. 11/593,021, filed Nov. 6, 2006, Bickel et al.

(Continued)

*Primary Examiner* — Angela M Bertagna
(74) *Attorney, Agent, or Firm* — Steptoe & Johnson LLP

(57) ABSTRACT

A device comprising a rigid substrate, a flexible cover element at least partially covering the substrate, a first structure formed in the substrate, adapted for accommodating liquids and adapted for releasing contents of one or more cells, spores, or viruses, the contents including the target molecules, a second structure formed in the substrate, adapted for accommodating liquids and comprising at least one binding member adapted for capturing the target molecules and for determining a value indicative for the presence and/or amount of the target molecules, a microfluidic network interconnecting at least the first structure and the second structure, and an actuator member adapted for effecting a fluid flow between the first structure and the second structure by pressing the flexible cover element against the substrate to selectively close a portion of the microfluidic network.

5 Claims, 46 Drawing Sheets

(56) References Cited

OTHER PUBLICATIONS

Boom R., Sol C.J., Salimans M.M., Jansen C.L., Wertheim-van Dillen P.M., van der Noordaa J., Rapid and Simple Method for Purification of Nucleic Acids, J. Clin. Microbiol. Mar. 1990;28(3):495-503.

Büchen-Osmond, C. (2003). *Taxonomy and Classification of Viruses*. In: Manual of Clinical Microbiology, 8th ed., vol. 2, p. 1217-1226, ASM Press, Washington DC.

Hess, S.T. et al. (2002) *Biochemistry* 41, 697-705.

Lichtman, J.W., and Conchello, J.A. (2005) *Nature Methods* 2, 910-919.

Liu, B. et al. (2005) *Proc. Natl. Acad. Sci. USA* 102, 589-593.

Perelson, A.S. et al. (1996) *Science* 271, 1582-1586.

Periasamy, A. (2001) *J. Biomed. Optics* 6, 287-291.

Prinz, A. et al. (2006) *Chembiochem.* 7, 1007-1012.

Szollosi, J. et al. (2002) *J. Biotechnol.* 82, 251-266.

Wilson, T., and Hastings, J.W. (1998) *Annu. Rev. Cell Dev. Biol.* 14, 197-230).

Xu, Y. et al. (1999) *Proc. Natl. Acad. Sci. USA* 96, 151-156.

Zimmermann, T. (2005) *Adv. Biochem. Eng. Biotechnol.* 95, 245-265.

Kessler et al. (2002), Clinical and Diagnostic Laboratory Immunology, 9(6):1385-1388.

Kessler et al. (1997), Clinical and Diagnostic Virology 7:139-145.

Kessler et al. (2001), Clinical and Chemistry 47(6):1124-1126.

Berger et al. (2002), Journal of Clinical Virology, 25(S 3): S103-S107.

Jungkind et al. (1996), Journal of Clinical Microbiology, 34(11): 2778-2783.

von Muller et al. (2007), Bone Marrow Transplantation, 39(6):353-357.

Paun et al. (2005), Journal of Virological Methods, 124(1-2): 57-63.

Stieger et al. (1991), Journal of Virological Methods, 34(2): 149-160.

\* cited by examiner

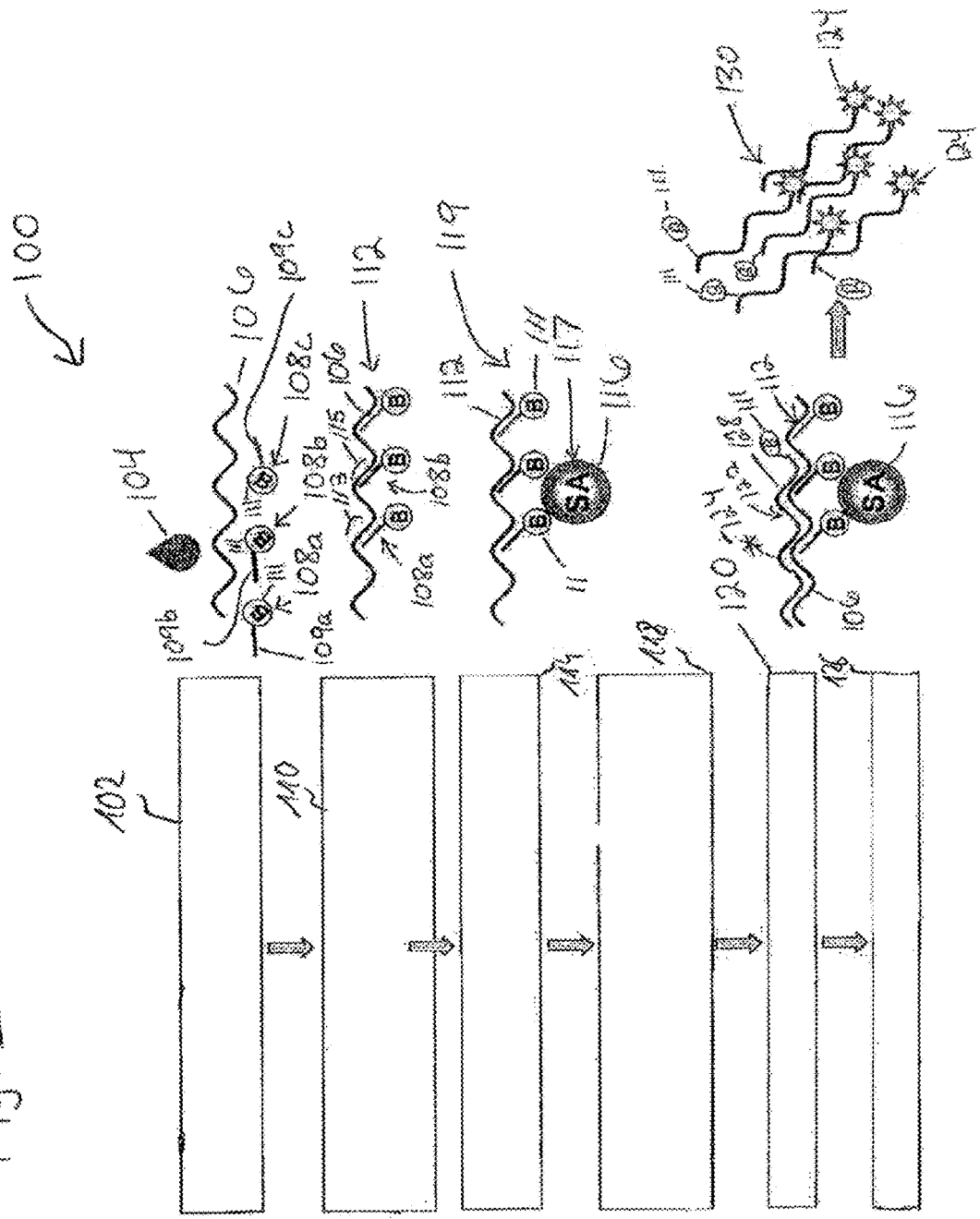

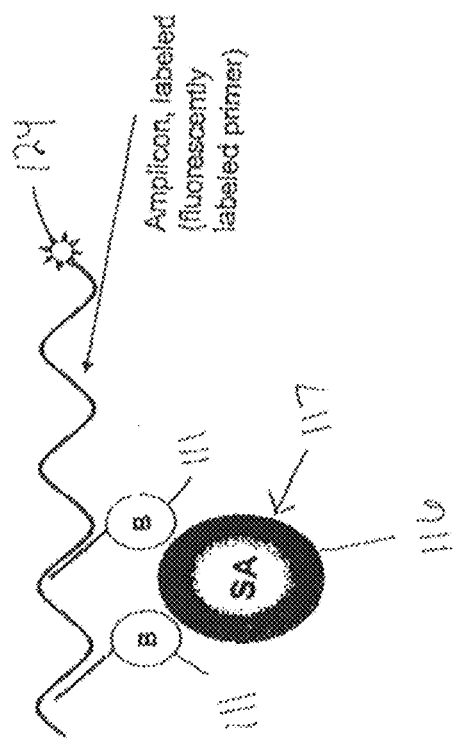

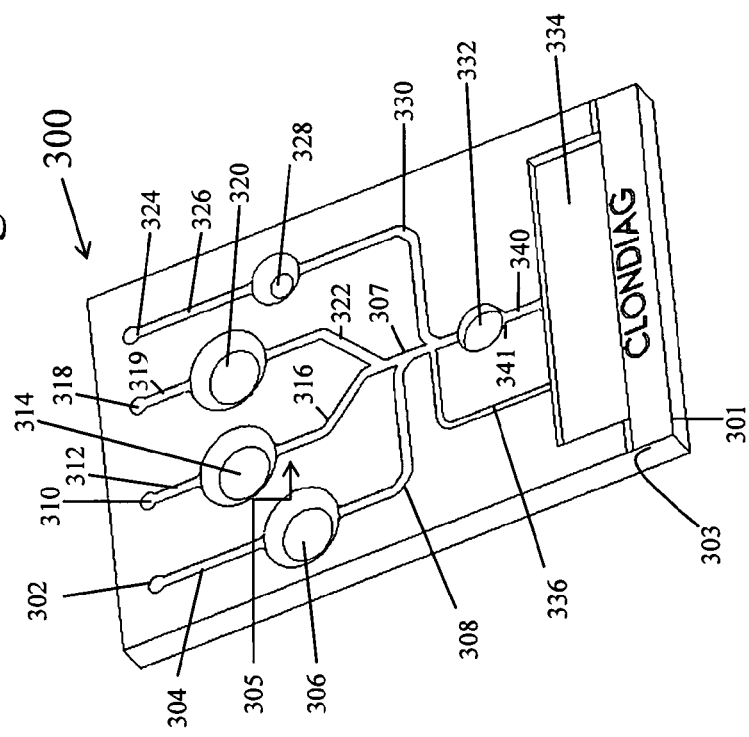

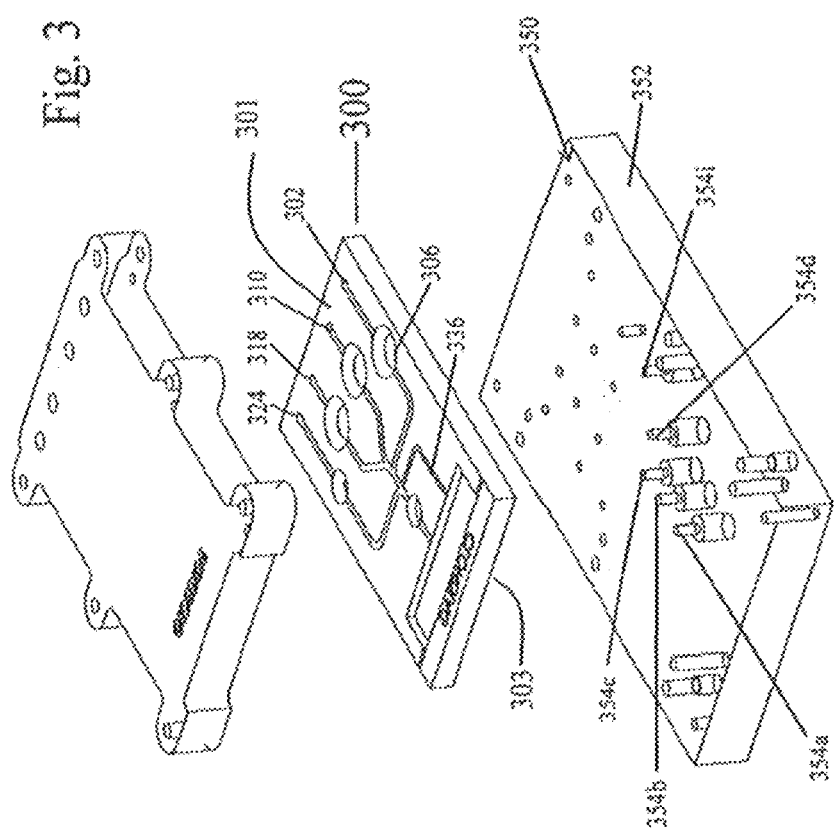

Fig. 6

2. Step - Capture of RNA complexes onto solid matrix (II)

Capture assay with streptavidin sepharose, RNA and 10 µl whole blood test amount of streptavidin sepharose

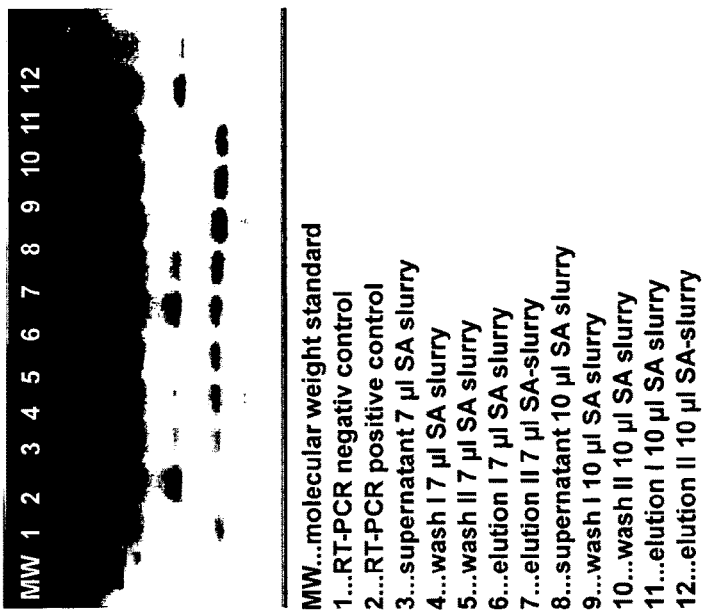

MW...molecular weight standard
1...RT-PCR negativ control
2...RT-PCR positive control
3...supernatant 7 µl SA slurry
4...wash I 7 µl SA slurry
5...wash II 7 µl SA slurry
6...elution I 7 µl SA slurry
7...elution II 7 µl SA-slurry
8...supernatant 10 µl SA slurry
9...wash I 10 µl SA slurry
10...wash II 10 µl SA slurry
11...elution I 10 µl SA slurry
12...elution II 10 µl SA-slurry

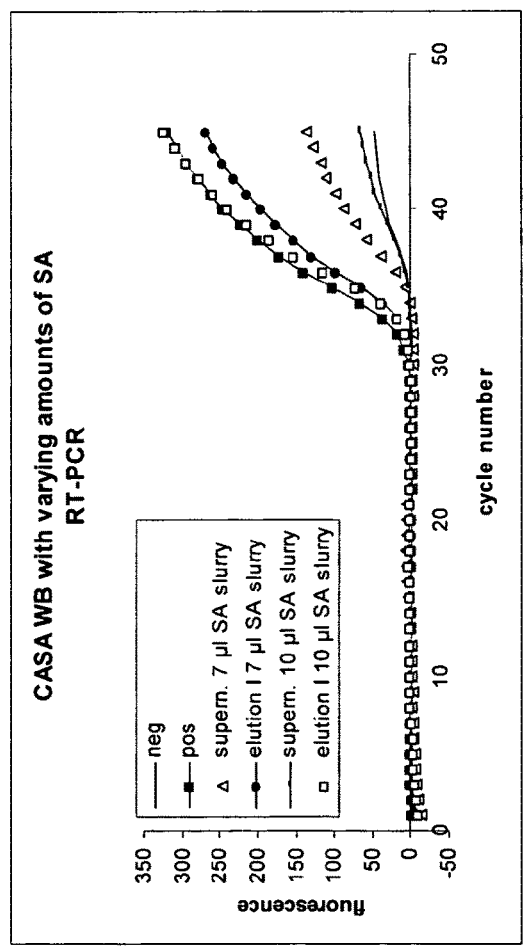

→ with 7 µl SA slurry, RNA is detected in the supernatant but 10 µl SA slurry are sufficient to capture RNA completely 3. Step - Wash Capture assay with 10 µl streptavidin sepharose, RNA and 10 µl whole blood
Test: lyophilyzed vs. fresh wash buffers → wash buffers can be lyophilized without loss of efficiency

FIG. 14

5. Step - Detection

RT-PCR, followed by detection of RT-PCR product on streptavidin sepharose one biotinyled strand in RT-PCR product Ⓑ
labeled probe ✶

RT-PCR without RNA
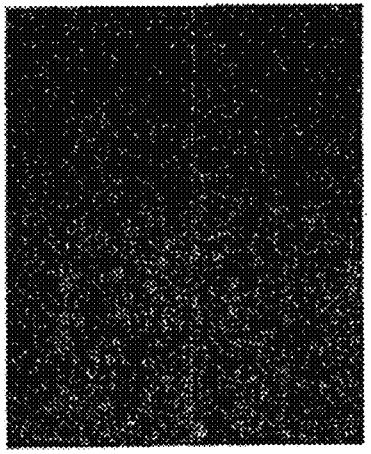

RT-PCR with RNA
130
119
134
117
111

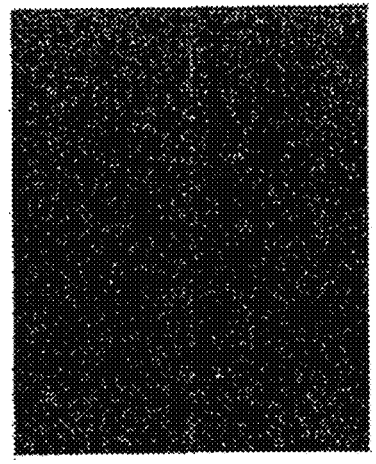

Fluorescent images of SA after incubation with/without RT-PCR product and Cy5-labeled probe (average bead diameter 34 μm, 10 sec exposition time)

→ amplified product can be concentrated and visualized on streptavidin sepharose
→ autofluorescence of streptavidin sepharose is low

Fig. 15

5. Step - Detection

RT-PCR with streptavidin sepharose after capture assay with whole blood (negative control: with blood and capture probe, but no RNA)

- HIV RNA in presence of 10 µl blood was captured onto streptavidin sepharose
- aliquot of streptavidin sepharose (SA) with purified RNA was used as template for RT-PCR
- another aliquot of streptavidin sepharose with purified RNA was elutetd and used as template for RT-PCR
- after RT-PCR samples with SA was incubated with Cy3-probe 1...RT-PCR negativ control
2...RT-PCR positive control
3...elution negative control
4...elution positive control
5...SA negative control
6...SA positive control
7...SA negative control, no taqman probe
8...SA positive control, no taqman probe
MW...molecular weight standard

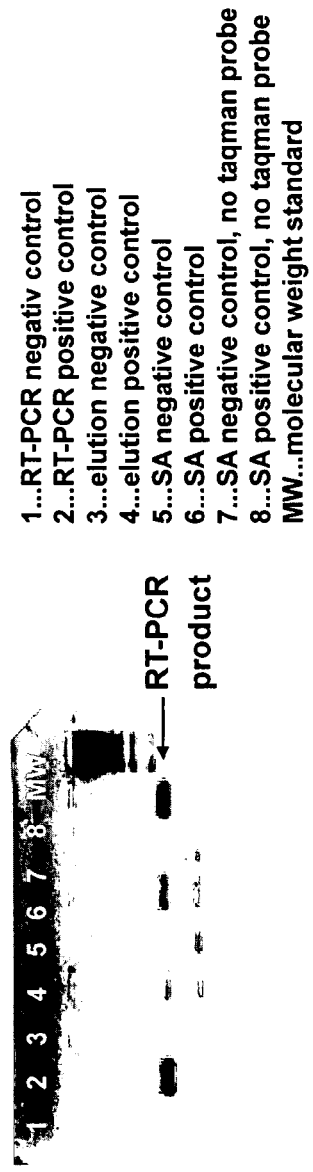

RT-PCR product fluorescent images of SA next page.....

Fig. 16
5. Step - Detection (cont.)
negative control (#7 on gel, for description see page before)
positive control (#8 on gel, for description see page before)
→ more fluorescent beads are visible in postive control, but detection needs to be optimized (non-specific binding of fluorescent probe to SA)

FIG. 24
A
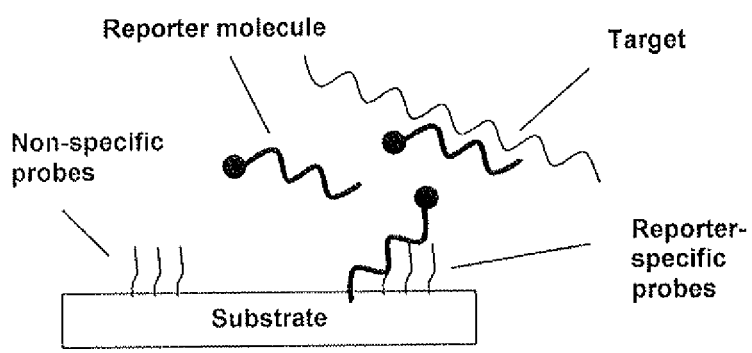
B
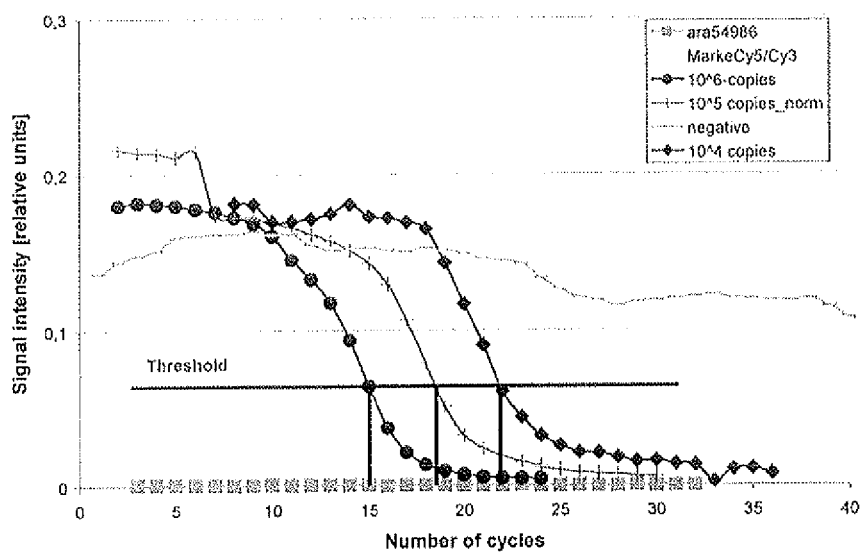
C
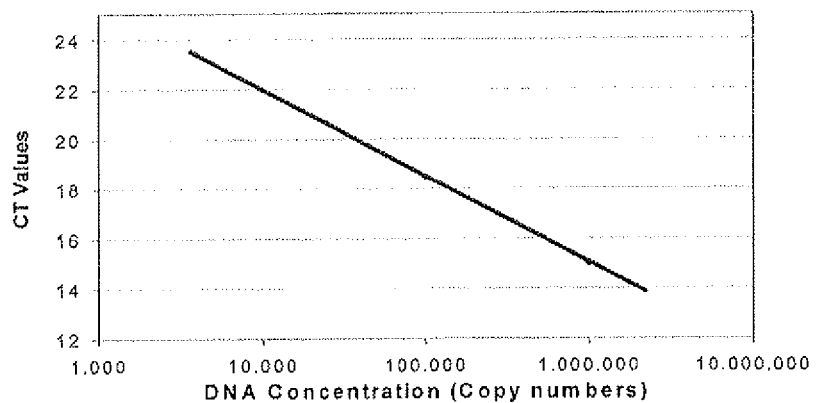

FIG. 25
A
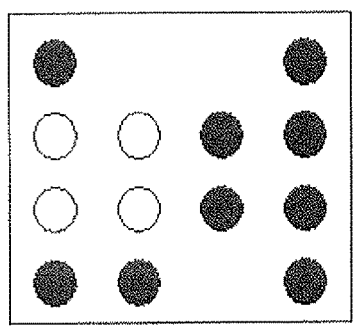
B
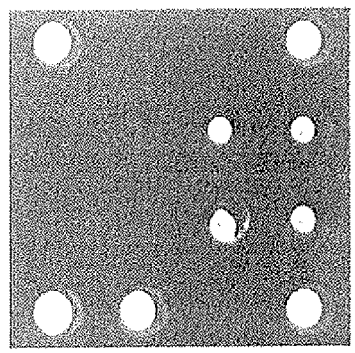
CYCLE 1
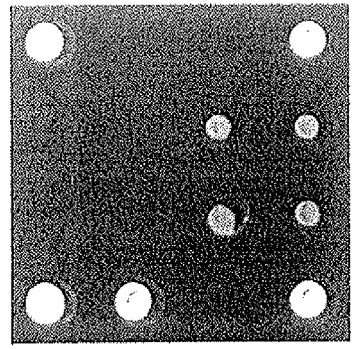
CYCLE 12
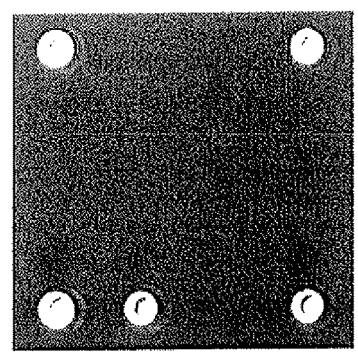
CYCLE 18
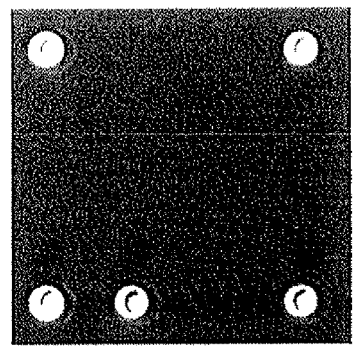
CYCLE 21

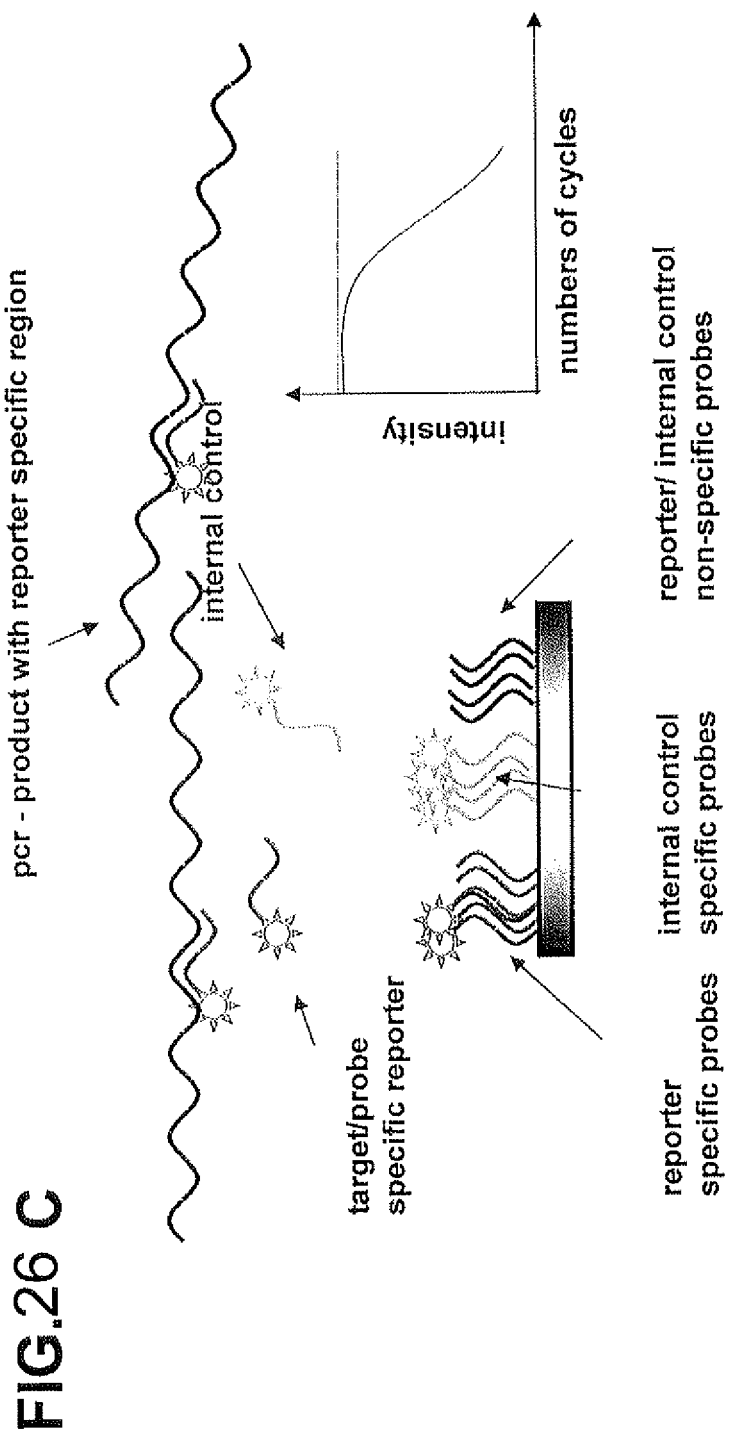

FIG. 33
A
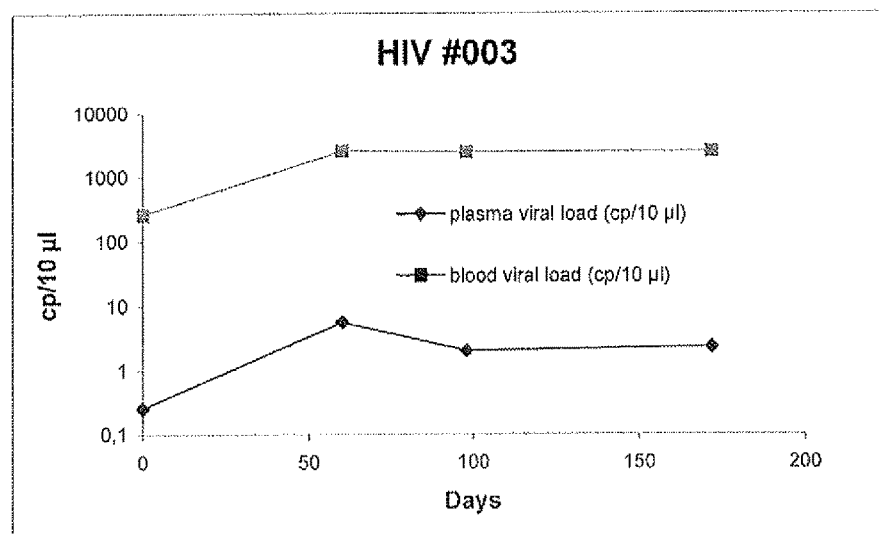
B
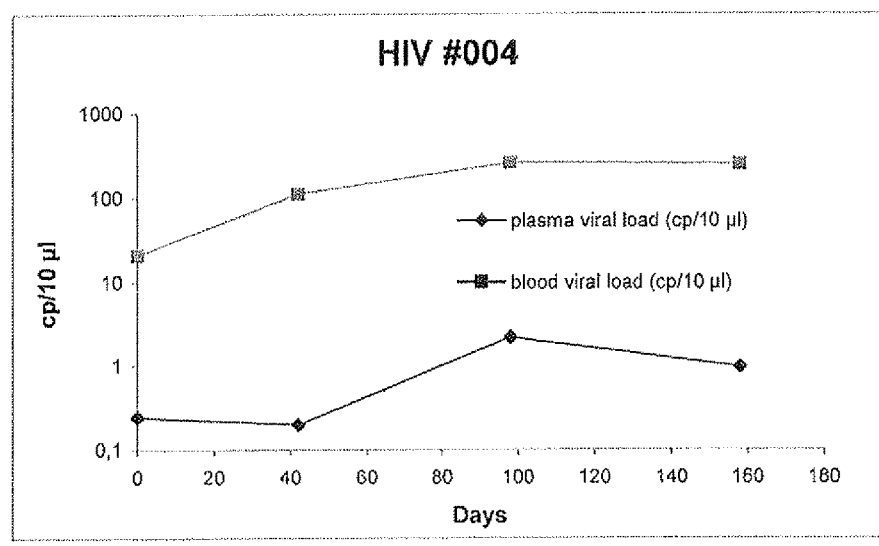

FIG. 34
A
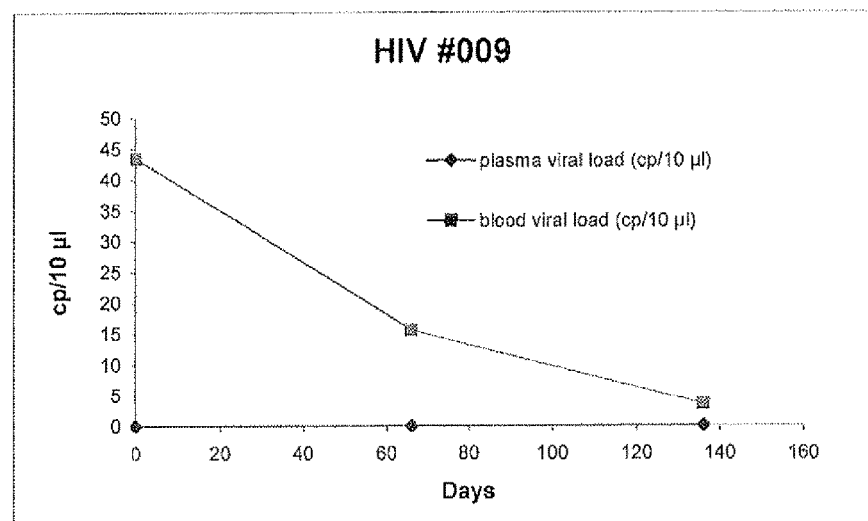
B
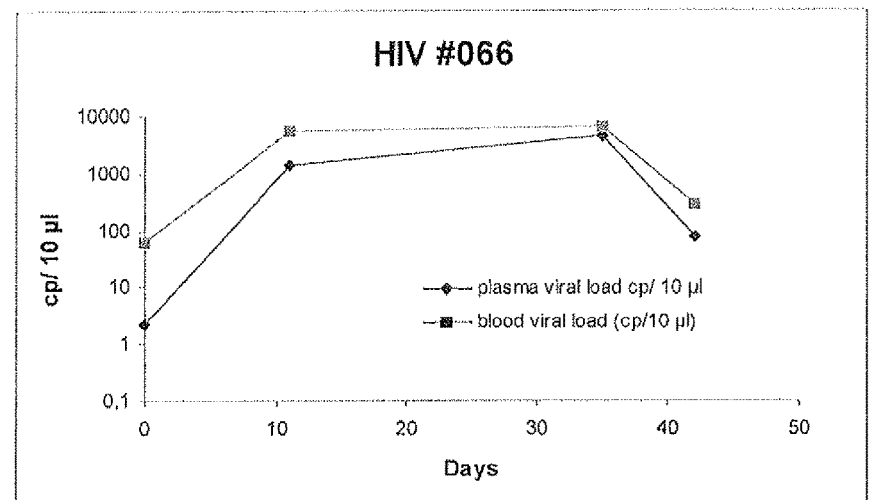

ASSAYS FOR MEASURING NUCLEIC ACIDS

CLAIM OF PRIORITY

This application claims priority under 35 USC 371 to International Application No. PCT/EP2008/059670, filed on Jul. 23, 2008, which claims priority to U.S. Provisional Application Ser. No. 60/951,358, filed Jul. 23, 2007, each of which is incorporated by reference in its entirety.

FIELD OF THE INVENTION

The present invention relates to assays, for instance assays for polynucleotides.

BACKGROUND

The presence of a pathogen in a biological sample can be determined by assaying the sample for a polynucleotide associated with the presence of the pathogen. Bacteria, mold, and viruses are examples of pathogens that can be determined based on an assay for associated polynucleotides.

EP 0 637 999 discloses devices for amplifying a preselected polynucleotide in a sample by conducting a polynucleotide polymerization reaction. The devices comprise a substrate microfabricated to define a sample inlet port and a mesoscale flow system, which extends from the inlet port. The mesoscale flow system includes a polynucleotide polymerization reaction chamber in fluid communication with the inlet port which is provided with reagents required for polymerization and amplification of a preselected polynucleotide. The devices may be utilized to implement a polymerase chain reaction (PCR) in the reaction chamber (PCR chamber). The PCR chamber is provided with the sample polynucleotide, polymerase, nucleoside triphosphates, primers and other reagents required for the polymerase chain reaction, and the device is provided with means for thermally controlling the temperature of the contents of the reaction chamber at a temperature controlled to dehybridize double-stranded polynucleotide, to anneal the primers, and to polymerize and amplify the polynucleotide.

However, it may be difficult to properly coordinate various tasks of conventional microfluidic devices.

SUMMARY

There may be a need for a device and a method enabling sample analysis in a simple manner. According to an exemplary embodiment, a device is provided, the device comprising a rigid substrate, a flexible cover element at least partially covering the substrate, a first structure formed in the substrate, adapted for accommodating liquids and adapted for releasing contents of one or more cells, spores, or viruses, the contents including the target molecules (for instance a dried buffer in the structure or chamber or well), a second structure (which may differ from the first structure) formed in the substrate, adapted for accommodating liquids and comprising at least one binding member adapted for capturing the target molecules and for determining a value indicative for the presence and/or amount of the target molecules, a microfluidic network interconnecting at least the first structure and the second structure, and an actuator member adapted for effecting a fluid flow between the first structure and the second structure by pressing the flexible cover element against the substrate to selectively close a portion of the microfluidic network.

According to another exemplary embodiment, a device is provided, the device comprising a structure adapted for accommodating liquids, wherein the structure comprises at least one binding member and is in fluid communication with a microfluidic network, and a control unit adapted for controlling a fluid flow through the micro fluidic network in such a manner that target molecules are captured at the at least one binding member, adapted for controlling an amplification of the target molecules in the structure, and adapted for controlling detection of compounds indicative for the presence and/or amount of the target molecules and captured at the at least one binding member.

According to still another exemplary embodiment, a method is provided, the method comprising accommodating liquids in a structure comprising at least one binding member and being in fluid communication with a microfluidic network, controlling a fluid flow through the microfluidic network in such a manner that target molecules are captured at the at least one binding member, amplifying the target molecules in the structure, and detecting compounds indicative for the presence and/or amount of the target molecules and captured at the at least one binding member.

According to still another exemplary embodiment, a device is provided, the device comprising a structure adapted for accommodating liquids, wherein the structure comprises a first binding member adapted for capturing a first compound and comprises a second binding member (which may differ from the first binding member) adapted for capturing a second compound (which may differ from the first compound) indicative for the presence and/or amount of the first compound.

According to an exemplary embodiment, a device may be provided in which a sample is guided, under the control of a control unit, through a micro fluidic device in such a manner as to perform a predefined analysis task. In the device, a central well/central structure (which may also be denoted as second well or second structure) may be provided which may perform several or all solid phase coupling procedures needed during the analysis. In the structure (which may be denoted as a central well), it may be possible to capture target molecules of a sample (for purification or separation purposes), to amplify target molecules (for instance by polymerase chain reaction, PCR), and to perform a (for instance optical) detection procedure which allows to derive information regarding the presence/absence or even the quantity of target molecules.

Therefore, a powerful and fully automatic biochemical analysis system may be provided, which may allow deriving, in a fast and accurate manner and without the requirement of much manpower, a biochemical or medical result. For instance, with such a device, it may be possible to detect nucleic acids associated with an HIV infection in a whole blood sample of a patient, in a qualitative or in a quantitative manner.

Next, further exemplary embodiments of the devices will be explained. However, these embodiments also apply to the method.

According to an exemplary embodiment, the compounds being detected in the central well are the target molecules. For this purpose, the central well may be provided with specific binding members (for instance binding members which differ from other binding members needed for capturing the target molecules). In other words, in such an embodiment the target molecules (e.g. nucleic acids originating from free and from cell-associated viruses such as HIV comprising RNA originating from free viruses, RNA originating from cell-associated viruses, pro-viral DNA, reverse transcribed viral DNA, i.e. the "intermediates" of viral replication, and transcripts derived from pro-viral DNA, i.e. RNA molecules obtained by transcription of the host DNA genome) may be bound to the binding members.

Alternatively, it is also possible to provide specific compounds such as reporter compounds which may have the capability to bind, for instance, to a PCR product, to RNA or to DNA. In such a scenario, the reporter compounds may be the compounds which are detected, thereby allowing to indirectly derive information regarding the presence and/or amount of target molecules in a sample.

The at least one binding member may be adapted for capturing the target molecules. For example, the at least one binding member may comprise labelled beads capable of capturing complexes including target molecules such as total viral nucleic acids.

The at least one binding member may be adapted for capturing compounds indicative for the presence and/or amount of the target molecules. Thus, not only the separate individual target molecules can be detected directly, but it is also possible to detect target molecules indirectly, for instance by detecting reporter compounds captured on a binding member.

The at least one binding member may comprise a first binding member adapted for capturing the target molecules and may comprise a second binding member (which may differ from the first binding member) adapted for capturing reporter compounds indicative for the presence and/or amount of the target molecules. Therefore, two different kinds of compounds may be provided, one specifically for capturing the target molecules after lysing, e.g. capture molecules comprising a binding portion specific to a region of a target polynucleotide and an anchor group; the other one for detection purposes, e.g. reporter compounds capable of forming complexes with the target polynucleotide, the forming of complexes with the target polynucleotide inhibiting capturing of the reporter compound by the second binding member. In other words, capturing may be functionally decoupled from detection. For example, the first binding member may be beads being configured to bind complexes comprising a capture molecule and a target molecule, e.g. by binding an anchor group of the capture molecule, whereas the second binding member may be a surface of the central well capable of capturing reporter compounds. The surface of the central well being the second binding member may comprise one or more different reporter specific capture molecules being capable of capturing a reporter compound on the surface.

The structure, that is to say the central member at which the various solid phase coupling procedures occur, may be a well. A "well" may be an indentation or a recess formed in a substrate and providing a sample chamber in which various analysis procedures may be performed. Such a well may be a cylindrical structure or pot having a volume in the order of magnitude between microliters and milliliters.

The central well or second structure may be irreversibly sealable, e.g. by sealing an inlet and, optionally, an outlet of the central well.

The microfluidic network may comprise a channel or a plurality of interconnected channels. A "channel" may denote a fluidic structure (for instance an essentially one-dimensional structure) having a length which is significantly larger than a width and a height, thereby providing a path along which liquids may be transported. A single channel may be provided, or several channels may be interconnected to form a channel system. Such a channel system may allow a liquid flow from one channel to another channel at bifurcations of such a system. One or more wells may be integrated in such a channel system.

In addition to a structure as described above, e.g. the "central" structure, the microfluidic network may comprise at least one further structure. In other words, apart from the channels and the central well, further microfluidic members may be provided, such as further channels and/or further wells. Therefore, a complex system of wells and channels may be provided.

At least one further structure (such as a lysis structure or a lysis well) may be adapted for releasing contents of one or more cells, spores, or viruses, the contents including the target molecules. Thus, such a further structure may be denoted as a lysis chamber in which biological compounds such as cells are forced to release their contents, for subsequent analysis. In other words, the further structure may comprise a structure comprising biochemical agents performing such tasks for releasing the contents, thereby providing a modified sample to be transported to the central well. To this end, the further structure such as a lysis structure may comprise a lysing reagent, for example chaotropic salts or a reagent comprising one or more detergents which disintegrate the cellular membranes and/or viral capsids. Alternatively or in addition, the further structure, e.g. the lysis well, may be adapted to heat the sample in order to destroy cellular membranes and/or viral capsids (e.g., by employing or comprising a temperature control unit and/or temperature regulating unit as described below).

The at least one further structure may also comprise capture probes capable of forming complexes with the target molecules. Therefore, it may be possible to lyse a sample in the presence of capture molecules with anchor groups.

At least one further structure (such as a well comprising PCR reagents) may comprise at least one substance promoting amplification of the target molecules. In other words, a further well may be provided which comprises biochemical agents needed for, i.e. promoting the amplification. However, although PCR agents may be included in the further structure, the actual PCR amplification procedure may be carried out at another position, namely in the central well. However, according to exemplary embodiments, as will be explained below in more detail, it may be advantageous to transport the sample from the central well through the well including the amplification substances well back to the central well again to avoid loss of sample material. Substances promoting amplification may be substances needed for PCR (such as enzyme, primer, buffer, etc.) and are described in detail below.

The at least one further structure may also be a well. Therefore, a plurality of wells connected by the microfluidic network may be provided. However, it may also be possible to perform lysing and/or to provide amplification material in other structures than wells, for instance in channels.

The device may comprise a substrate, on and/or in which the structure(s) may be formed. Therefore, fluid accommodating components of the device may be monolithically integrated in the substrate. Alternatively, structure(s) may be formed on a substrate, for instance printed or spotted. Examples for materials of a rigid substrate which may properly cooperate with a flexible cover element are polycarbonate, polypropylene, polystyrene, PET, PMMA, polyethylene, acrylic glass, PU, PEEK, PVC, glass, and the like.

Particularly, the substrate may be rigid allowing to cooperate with one or more flexible cover elements at least partially covering the substrate in a very efficient manner. Particularly, the flexible cover element may cover the rigid substrate, and an actuator may press the cover element against the substrate to selectively close channels (for performing valve functions or the like).

According to an exemplary embodiment, the substrate may have a first surface and a second surface opposing the first surface. The structure may be provided on and/or in the first surface (particularly a first main surface) of the substrate. The main surface is the principal surface of the substrate upon which the structure is configured. A further structure may be provided on and/or in the second surface (particularly a second main surface) of the substrate. A fluidic connection structure may be provided, particularly a through hole penetrating the substrate and/or a groove in a surface portion of the substrate connecting the first surface with the second surface. Such a fluidic connection structure may be arranged between the first and the second surface and may be configured to provide a fluid communication of the structure with the further structure. In such an embodiment, the substrate may be processed at two opposing main surfaces to thereby form microfluidic structures. These structures may be connected by the connection structure which may comprise channels formed along a surface of the substrate, or directly going through the substrate. Therefore, a device may be provided in which both main surface portions of the substrate may be used in a very efficient manner, since both main surfaces of such a substrate may be processed for providing liquid transport tasks. Optionally, such a substrate may be covered on one or both sides with a (particularly flexible) cover element, thereby allowing to control fluid flow through fluidic structures on both surfaces efficiently, for instance by actuators acting on flexible portions on one or both main surfaces. Thus, a central substrate may be provided having fluidic structures on both sides. Particularly, this may allow manufacturing a cartridge formed by three layers, namely the substrate and two at least partially flexible cover elements. Such a three layer structure may have a (for instance flexible) base element and a (for instance flexible) cover element sandwiching an intermediate layer (for instance being rigid) accommodating the microfluidic structures. Base element and/or cover element may cover the central substrate entirely or only partially, for instance at positions at which a cover function is desired as a basis for an actuator based control (see, for instance, FIG. 21).

In addition to the substrate, the device may comprise at least one further substrate, wherein a further structure may be provided on and/or in the further substrate. The substrate and the further substrate may be adapted to be connectable or mountable or assemblable or installable reversibly or detachably to one another in such a manner that the structure and the further structure may be brought in fluid communication in an operation state in which the substrate is connected or mounted or assembled or installed with the further substrate. According to such an embodiment, a modular construction may be provided in which a device may be formed by combining several modules which can be flexibly connected to one another. A corresponding cartridge may be formed by a modular construction set, wherein each of the modules may have the following properties and may be used in combination with other cooperatively formed modules:
- it comprises a chamber having at least two fluid connections;
- the chamber comprises a rigid component and an elastic component;
- at least one fluid connection may be closable by the motion of the elastic component, and a mixing of the content of the chamber may be effected.

The at least one binding member may be adapted such that a plurality of solid phase coupling procedures during an analysis of the target molecules occur at the at least one binding member. The term "solid phase coupling procedure" may particularly include any kind of anchoring and hybridization, etc., at a functionalization/binding member. In this context, the "binding member or support member" may include any substance, surface or functionalization being configured to bind an anchor group of capture molecules and/or a surface being configured to capture polynucleotides. Solid phase coupling procedures may include any procedure in which molecules to be analyzed or detected are specifically bound to a solid surface, that is to say are bound not in a solution but on a solid surface.

The at least one binding member may be adapted such that all solid phase coupling procedures during an analysis of the target molecules occur at the at least one binding member. In other words, in such an embodiment, no solid phase coupling procedures occur at another well than at the central well/structure. This may allow performing all solid phase coupling procedures in a single well, allowing for a miniature and high performance device. The at least one binding member may be adapted such that exactly two solid phase coupling procedures during an analysis of the target molecules occur at the at least one binding member. These two solid phase coupling procedures may relate to capturing target molecules from a multi-component sample, and to detecting compounds indicative of the presence or absence or the quantity of the target molecules. In the described embodiment, these two procedures are performed in a single well allowing to synergistically use provisions of the well for both such tasks. Combining such two tasks in one well may keep liquid flow paths short, keep the device small, and keep the analysis time short.

In some embodiments, the at least one binding member may be adapted such that exactly three solid phase coupling procedures during an analysis of the target molecules occur at the at least one binding member. These three solid phase coupling procedures may relate to capturing target molecules from a multi-component sample, capturing nucleic acids resulting from reverse transcription of target nucleic acids, and to detecting compounds indicative of the presence or absence or the quantity of the target molecules. In the described embodiment, these three procedures are performed in a single well allowing to synergistically use provisions of the well for all such tasks. Combining such three tasks in one well may keep liquid flow paths short, keep the device small, and keep the analysis time short.

Alternatively, the at least one binding member may be adapted such that exactly one solid phase coupling procedure during an analysis of the target molecules in the sample occurs at the at least one binding member. Such an embodiment may be particularly advantageous, when the entire biochemical analysis or experiment only comprises a single solid phase coupling procedure, for instance is only foreseen for sample purification, not for detection.

At least a portion of the device located adjacent to the at least one binding member may be transparent for electromagnetic radiation in a range of wavelengths between essentially 1 nm and essentially 10 µm to thereby allow for an electromagnetic radiation based detection of the compounds indicative for the presence and/or amount of the target molecules and captured at the at least one binding member. In such embodiments, particularly a portion of the substrate close to the central well may be transparent for electromagnetic radiation used for detection purposes, particularly for electromagnetic radiation in the near-infrared, optical and ultraviolet domain. By taking this measure, it may be possible to perform also the detection on the basis of electromagnetic radiation (for instance a fluorescence-based detection) in the central well. When the portion of the device located adjacent to the at least one binding member is transparent for electromagnetic radiation in a range of wavelengths between essentially 400 µm and essentially 800 µm, an optical detection of the compounds is enabled.

The device may comprise or may be connectable with a temperature manipulation unit adapted for manipulating a temperature of liquids located in the structure. Such a temperature manipulation unit may comprise a heating and/or cooling element which allows to bring a sample to a specific temperature, or to conduct a specific temperature pattern or sequence.

The temperature manipulation unit may be adapted for manipulating a temperature of liquids located in the structure in accordance with a temperature sequence for performing a polymerase chain reaction (PCR). Such a polymerase chain reaction may require temperature cycles to, for instance about 95° C., about 55° C. and about 72° C. Such a sequence of temperatures usually has to be performed for specific predefined time intervals, and has to be repeated a predefined plurality of times.

The at least one binding member may be configured to bind an anchor group of a capture molecule. Particularly, the at one least binding member may be configured to capture polynucleotides.

The at least one binding member may comprise at least one of the group consisting of capture molecules, e.g. reporter specific capture molecules, arranged on a surface of the structure (for instance immobilized in the well), capture molecules arranged on particles (for instance on beads), capture molecules arranged on a porous surface of the structure (for instance a porous glass structure), and one or more different capture molecules, e.g. reporter specific capture molecules, arranged on different locations with respect to a surface of the structure (for instance different kinds of capture molecules being immobilized in an array-like manner in the well, for instance in the context of a competitive assay). In some embodiments, the at least one binding member also may comprise capture molecules for capturing an anchor group such as biotin.

The structure may have a volume in a range between essentially 1 µl and essentially 1 ml, particularly in a range between essentially 20 µl and essentially 300 µl. For example, a well having a volume of essentially 100 µl may be provided.

The substrate may have a groove configured to receive a cannula for supplying liquids to the device. In such an embodiment, it may be very easy for a user to handle the device, since the cannula for sample supply simply has to be placed in the groove to be brought in proper accordance and cooperation with the micro fluidic channel system, thereby allowing for an easy analysis which may be performed even by users which are not specifically skilled or trained.

The substrate may have a window portion adjacent the structure and being transparent for electromagnetic radiation in a range of wavelengths between essentially 1 nm and essentially 10 µm (that is to say for near infrared, optical or ultraviolet radiation), particularly in a range of wavelengths between essentially 400 nm and essentially 800 nm (that is to say particularly for optical radiation), to thereby allow for an electromagnetic radiation based detection of a meniscus of a liquid flowing through (more precisely reaching) the structure or the microfluidic network. In such an embodiment, an optically transparent window portion of the substrate may be detected by a radiation detector. When a meniscus of a fluid pumped through the microfluidic network or the structure passes the window portion, this may abruptly change the transmission properties through the window portion in a characteristic manner, thereby generating a signal at a radiation detector indicative for the fact that the meniscus has reached a specific region in the device. This signal may be useful for triggering purposes, or as a control signal for actuators, because the cooperative motion of actuators and/or the control of temperature manipulation units can be brought in proper accordance with the present position of a sample being pumped through the device. For instance, by taking such a measure, it may be detected that a predefined volume of water or buffer has been pumped into the device, when an overflow occurs.

At least one of the group consisting of the structure and the further structure may comprise two fluid openings. Such fluid openings may be a fluid inlet and a fluid outlet.

The cover element may be a flexible cover element. Particularly in cooperation with a rigid substrate, the cover element and the substrate may form three-dimensionally sealed channels which can be properly controlled by actuators acting on the cover element. When the cover element is at least partially deformable at a specific position under the influence of an external force, it may be possible to selectively enable or disable a flow of liquids by opening or closing the structure or the microfluidic network. Beyond this, a transport of liquids along the structure is possible with such a cover element.

Particularly when an actuator member is provided and adapted for being actuated to deform the cover element, a high performance lab-on-chip may be provided which has integrated mixing, pumping and/or valve functions.

Any one of the structures may comprise one or more substances being biologically, biochemically and/or chemically active. Therefore, when such substances, which may include capture molecules, reporter-specific capture molecules, detectable markers, lysing reagents and PCR reagents, are present in the wells in dried form, particularly in lyophilized form, it is possible to provide a device which a user simply has to fill with liquids (such as water, buffers and sample) to perform a fully automatic analysis. When the necessary biochemical components are provided in the different wells, a user can simply start an experiment on the basis of a sequence stored in the control unit and may provide water or buffers to different inlet chambers. The remainder will be performed by the fully automatic device.

The channel may have a width (that is a dimension in a surface plane of the substrate and perpendicular to a fluid flow direction) in a range between essentially 50 µm and essentially 1 mm, particularly in a range between essentially 100 µm and essentially 300 µm. For example, a width of the channel may be essentially 200 µm. A height (that is a dimension in a direction perpendicular to a surface plane of the substrate and perpendicular to a fluid flow direction) of the channel may be in a range between essentially 20 µm and essentially 300 µm, particularly in a range between essentially 50 µm and essentially 200 µm. For example, a height of the channel may be essentially 100 µm. In contrast to this, a length of the channel may be much larger than the width and the height, for instance may be larger than 1 mm, particularly may be larger than 1 cm or may even be several centimeters.

The structure may comprise a material adapted as a transport medium for liquids. For example, the material may comprise at least one of the group consisting of a solid material, a gel material, a liquid material, and a combination thereof. Therefore, the structure may be a recess or may be formed by material serving as a carrier for the liquids.

The cover element may comprise a flexible membrane or a flexible sealing. Such a flexible membrane or flexible sealing may be made of materials such as latex, thereby enabling the cover element to be flexibly deformed under the influence of a mechanical force (for instance generated by an actuator member).

The device may comprise an actuator member adapted for being actuated for deforming the cover element to thereby control a fluid flow property of liquids in the structure and/or in the micro fluidic network. Such an actuator member may be under the control of the control unit and may have a plurality of cooperating pins or stencils acting on the flexible cover element to thereby selectively open or close channels, temporarily reduce the volume of a channel or well for pumping or mixing purposes, etc.

The actuator member may particularly be adapted for controlling a fluid flow property of liquids along a straight portion of a channel. When a fluid flows along a straight channel, a perpendicularly arranged actuator member may efficiently disable a fluid flow when this channel is closed at a specific portion.

The actuator member may be adapted for functioning as a valve, as a fluid mixer, and/or as a fluid pump.

More particularly, the actuator member may comprise a plurality of actuator elements adapted for being cooperatively actuated for deforming the cover element to thereby control the fluid flow property of liquids in accordance with a fluid flow scheme defined by the control unit. Therefore, when a user has selected a specific experiment or assay, which involves the transport of fluids and samples through various channels, the control unit simply controls the individual stencils of the actuator member to provide such a reversible compression of the flexible cover element, to thereby fully automatically perform the assay.

The control unit may be adapted to control the actuator member to deform the cover element in such a manner that target molecules are captured at the at least one binding member, that the target molecules are amplified in the structure, and that compounds indicative for the presence and/or amount of the target molecules and captured at the at least one binding member are detected. Thus, the control unit may be the central regulator of the device harmonizing the function of the various components.

The actuator member may comprise one or more pins configured to be reciprocated. By moving a pin in a forward direction, a channel may be closed by pressing the flexible cover element towards the substrate in this channel. When the pin is moved backwardly, the channel may be opened again to allow for a fluid flow. In some embodiments, the one or more pins may have an at least partially elastic tip.

The actuator member may further be provided to be movable in a direction perpendicular to a main surface of the substrate. By reciprocating in a direction which is perpendicular to the planar substrate, an efficient opening and closing may be made possible. Particularly, the actuator member may be provided movably to selectively close at least a part of the structure to disable a transport of liquids through the structure. In another operation mode, the actuator member may be moved to selectively open at least a part of the structure to enable a transport of liquids through the structure.

The actuator member may be adapted for reciprocating perpendicular to a main surface of the substrate for selectively enabling or disabling a fluid flow of liquids through the structure. The use of reciprocating actuators may allow for reversibly and selectively enabling or disabling fluid flows, allowing for a very flexible operation of the device and allowing for using the device multiple times (in contrast to approaches in which channels are closed irreversibly for performing a one-way valve function).

The actuator member may be adapted for reciprocating in a perpendicular direction to a main surface of the substrate for pumping liquids through the structure. Therefore, it is possible that the actuator member controls a volume or height of the structure. The actuator member may also selectively close the structure. Closing a structure may be performed in the context of a valve function, of a mixing function or of a pumping function. However, it is also possible to use such an actuator during a detection phase, since it is possible to compress the structure and/or binding members for detection purposes to increase the local concentration of target molecules to be detected and/or to remove background signals. This may allow increasing the accuracy.

A drive unit may be provided for mechanically driving the actuator member, wherein the drive unit may be controllable by the control unit. Such a drive unit may comprise a pneumatic drive mechanism, a hydraulic drive mechanism, or an electromagnetic drive mechanism.

The at least one binding member may comprise a three-dimensional medium, for instance a gel, particles, beads or a porous matrix. The three-dimensional medium may be arranged and configured to be reversibly compressible by moving the actuator member. By taking this measure, a very accurate detection may be made possible, because the local concentration of the molecules to be detected may be selectively increased by compressing the three-dimensional medium (such as beads) having attached thereto compounds or complexes indicative for the presence or the quantity of the target molecules.

The device may be adapted as a biosensor assay device, a microfluidic cartridge, or a lab-on-chip. Therefore, on a small scale, various biochemical functions may be combined to perform an entire biochemical experiment.

A temperature sensor may be provided and adapted for sensing a temperature of liquids transported through the device. The temperature sensor may be integrated in a substrate to thereby sense the temperature of the liquids flowing through the microfluidic network. Alternatively, the temperature sensor may be arranged at the actuator member, for instance at a tip of a stencil-like actuator, so that the actuator, when pressing the cover element against the substrate, may simultaneously measure the local temperature of the fluid.

The device may comprise a temperature manipulation unit adapted for manipulating a temperature of liquids, and preferably arranged at the actuator member. Such a temperature manipulation unit may also be integrated within the substrate, for example in the form of heating wires integrated in the substrate and heating sample in the well. Alternatively, such a temperature manipulation unit may be an external device such as an external electromagnetic radiation source wherein electromagnetic radiation (for instance from a laser) may be directed onto a well resulting in a heating of the fluid in the well using the electromagnetic radiation as an energy source. Further alternatively, the temperature manipulation unit may include not or not only a heating element, but also a cooling element. For such an embodiment, a Peltier cooler may be implemented with low effort.

A temperature manipulation unit may be provided and adapted for manipulating a temperature of liquids, wherein the temperature manipulation unit may comprise a first heating element and a second heating element, the structure being arranged between the first heating element and the second heating element. By providing two such heating plates, one being a continuous plate and the other one being an annular plate, heating may be performed without disabling the device to be operated with an electromagnetic radiation based detector, since a recess in the annular plate may allow electromagnetic radiation to be directed onto the central well and may allow fluorescence radiation to be detected through the recess and the second heating element.

According to an exemplary embodiment at least one of the heating/cooling elements is flexibly mounted. Flexibly mounting the heating/cooling elements may allow for an easy insertion of a structure, e.g. the second structure or central well, between the first and second heating/cooling elements. Further, flexibly mounting at least one of the heating/cooling elements may allow for flexibly adapting the flexible heating/cooling element to the surface of the structure, e.g. the second structure or central well, so that the flexible heating/cooling element is forced to contact the surface of the structure and thus also allows for an efficient thermal conductance.

According to an exemplary embodiment the flexibly mounting is a flexible mounting of the whole heating/cooling element.

According to a further exemplary embodiment the flexibly mounting is a flexibility of the heating/cooling element as such.

Further, also two heating/cooling elements may be flexibly mounted. The both heating/cooling elements may be arranged in a butterfly fashion to sandwich the probe device. In the same fashion a single heating/cooling element may be arranged with a pressing counter plate. This may avoid any scratches when inserting the probe device, in particular when the heating/cooling elements will be moved towards the surfaces of the probe device after the probe device has reached its final position.

In some embodiments, each of the heating element or cooling element, or both, is a Peltier element.

A temperature regulation unit may be provided and adapted for regulating a temperature of liquids in the structure. Such a regulation entity may include the measurement of the actual temperature and, on the basis of this measurement, the performance of a heating and/or cooling performance to thereby adjust the temperature to a desired value.

A detection unit may be provided and adapted for detecting, in the structure, compounds indicative for the presence and/or amount of the target molecules and captured at the at least one binding member. Such a detection unit may comprise an optical detection unit, particularly a fluorescence detection unit.

The substrate and the cover element may be separate components which are connected to one another. Alternatively, the substrate and the cover element may be made of different materials.

A transport unit may be provided and adapted for transporting liquids through the structure and/or the microfluidic network. Such a transport unit may comprise a pump, particularly one of the group consisting of a compressed-air pump, a hydraulic pump, a peristaltic pump, and a vacuum pump. Furthermore, the device may be adapted in such a manner, during normal use, the gravitational force promotes the flow of liquids through the device in a desired manner. Therefore, in the absence of the activity of a transport unit, liquids may directly flow in a desired direction. However, when the transport unit is switched on, the influence of the transport unit may be larger than the influence of the gravitation, thereby allowing to selectively initiate a fluid flow in a direction against the gravitational force. Therefore, the combination of gravity and a special transport unit may be highly advantageous and may allow for an energy-saving operation.

The transport unit may be adapted for transporting liquids by actuating a gas bubble in the structure and/or in the micro fluidic network. By moving a gas bubble through the device, the transport of the liquids through the device may be supported or promoted.

At least one filter, particularly at least one frit, may be arranged at the structure (that is to say at an inlet and/or at an outlet of the central well) and may be adapted for preventing the at least one binding member (for instance beads) arranged in the structure, from being washed out of the structure. Under the influence of a fluid flow, a mechanical force may act on the beads or other binding members in the structure. However, when a frit, that is to say a porous filter element which may be made of a sinter material, is provided at an inlet and/or an outlet of the structure it may be securely prevented that the beads are washed out of the central chamber. The frit may be provided with an annular shape to allow for being inserted into a correspondingly shaped annular groove in the device.

The at least one binding member may comprise a surface functionalization. The term "surface functionalization" may denote the fact that the surface is processed in such a manner as to perform a specific binding function. In such an embodiment, the binding member may be part of or coupled to or attached to the surface of the well.

The substrate and the cover element may be in direct contact to one another. Alternatively, the substrate may be free of a direct contact with the cover element. Various geometrical realizations are possible.

A portion of the substrate located adjacent to the structure may be transparent for electromagnetic radiation in a range of wavelengths between essentially 400 nm and essentially 800 nm to thereby allow for an optical detection in the structure. Therefore, visible light may be used for detection purposes. Such a detection may be performed on the basis of light absorption, light reflection, or fluorescence generation, for instance using fluorescence labels attached to molecules or complexes to be detected.

The at least one binding member may be adapted such that at least two solid phase coupling procedures during an analysis of the target molecules occur at exactly one of the at least one binding member. In other words, one and the same binding member may be used for multiple solid phase coupling procedures. For example, beads with attached groups may be used for capturing target molecules out of the sample, and may be used later for capturing compounds such as amplified and labelled target molecules as a basis for a subsequent detection.

Alternatively, the at least one binding member may be adapted such that at least two solid phase coupling procedures during an analysis of the target molecules occur at different ones of the at least one binding member. E.g., the device includes multiple binding members and at least one binding member is adapted such that at least two solid phase coupling procedures during an analysis of the target molecules occur at two or more of the at least one binding member. In such a configuration, for example, capturing molecules from a sample on the one hand, and detecting components indicative of the target molecules on the other hand are captured using two different kinds of binding members. For example, beads may be provided for capturing the target molecules out of a sample. On the other hand, capture molecules, e.g. reporter specific capture molecules immobilized in the well may be used in the context of a competitive assay for capturing the components indicative of the presence or amount of target molecules in the sample, e.g. reporter compounds.

According to another exemplary embodiment of the invention, a method is provided comprising forming complexes, each comprising a target nucleic acid and a capture molecule, wherein each capture molecule comprises a binding portion specific to a region of the target nucleic acid and an anchor group; contacting the complexes with a binding member, the binding member being configured to bind the anchor group of the capture molecule to bind the complexes to the binding member; subjecting one or more target nucleic acids to an amplification; capturing the amplified target nucleic acids with respect to the binding member; and determining a value indicative for the presence and/or amount of the captured target nucleic acids.

The one or more target nucleic acids may be single-stranded or double-stranded nucleic acids.

The method may further comprise subjecting the target nucleic acids to reverse transcription prior to subjecting one or more target nucleic acids to amplification.

The method may further comprise releasing the captured amplified target nucleic acids from the binding member and repeating the steps of subjecting one or more target nucleic acids to amplification and capturing the amplified target nucleic acid with respect to the binding member. In such an embodiment, the cycle of releasing the captured amplified target nucleic acids from the binding member and repeating the steps of subjecting one or more target nucleic acids to amplification and capturing the amplified target nucleic acids with respect to the binding member may be performed at least 10 times or at least 20 times.

A value indicative for the presence and/or amount of the captured target nucleic acids may be determined after at least one cycle, e.g. after each cycle, of releasing the captured amplified target nucleic acids from the binding member and repeating the steps of subjecting one or more target nucleic acids to amplification and capturing the amplified target nucleic acids with respect to the binding member.

The binding member may comprise one or more capture molecules capable of capturing the target nucleic acids. In such an embodiment, the target nucleic acids are captured with respect to the binding member by the one or more capture molecules.

The binding member may further comprise particles.

The step of forming complexes each comprising a target nucleic acid and a capture molecule may be performed spatially separated from the step of contacting the complexes with a binding member.

The method may further comprise labeling the target nucleic acids. The target nucleic acids may be labeled by adding or more detectable markers, e.g. prior to or during subjecting one or more target nucleic acids to amplification and/or prior to capturing the amplified target nucleic acids with respect to the binding member. The one or more detectable markers may be fluorescent markers.

Determining a value indicative for the presence and/or amount of the captured target nucleic acids may comprise time-dependent monitoring of the one or more indicative values obtained.

The method may further comprise providing the one or more target nucleic acids prior to forming complexes each comprising a target nucleic acid and a capture molecule. The step of providing one or more target nucleic acids may comprise releasing the target nucleic acids from biological material. In such an embodiment, the biological material may be selected from the group consisting of one or more prokaryotic cells, one or more eukaryotic cells, one or more erythrocytes, and one or more viral particles as well as mixtures thereof. Further, releasing the target nucleic acids from biological material may comprise contacting the biological material with a lysing reagent.

Providing the one or more target nucleic acids may comprise providing a sample comprising the one or more target nucleic acids wherein the sample may be selected from the group consisting of whole blood, plasma, serum, urine, sputum, saliva and cerebrospinal fluid.

Providing the one or more target nucleic acids may be performed spatially separated from the contacting complexes each comprising a target nucleic acid and a capture molecule, subjecting the one or more target nucleic acids to amplification, capturing the amplified target nucleic acids with respect to the binding member and determining a value indicative for the presence and/or amount of the captured target nucleic acids.

The method may further comprise separating the one or more target nucleic acids from concomitant material.

In a further embodiment, the method according this exemplary embodiment is performed in a device as described above. E.g., the method may be performed in a device, comprising a rigid substrate; a flexible cover element at least partially covering the substrate; a first structure formed in the substrate, adapted for accommodating liquids and adapted for releasing contents of one or more cells, spores, or viruses, the contents including target molecules such as target nucleic acids; a second structure formed in the substrate, adapted for accommodating liquids and comprising at least one binding member adapted for capturing the target molecules and for determining a value indicative for the presence and/or amount of the target molecules; a microfluidic network interconnecting at least the first structure and the second structure; and an actuator unit adapted for effecting a fluid flow between the first structure and the second structure by pressing the flexible cover element against the substrate to selectively close a portion of the microfluidic network. Further, the method may be performed in a device, comprising a structure adapted for accommodating liquids, wherein the structure comprises at least one binding member and is in fluid communication with a microfluidic network; and a control unit adapted for controlling a fluid flow through the microfluidic network in such a manner that target molecules such as target nucleic acids are captured at the at least one binding member, adapted for controlling an amplification of the target molecules in the structure, and adapted for controlling detection of compounds captured at the at least one binding member.

The device may comprise a first structure adapted for accommodating liquids. In such an embodiment, the complexes each comprising a target nucleic acid and a capture molecule are formed in the first structure.

Further, the device may comprise a second structure configured for detecting one or more target nucleic acids and comprising a cover element covering the second well and an actuator unit adapted for being actuated to deform the cover element. In such an embodiment, determining a value indicative for the presence and/or amount of the captured target nucleic acids may be performed in the second structure.

Further, subjecting one or more target nucleic acids to amplification and/or capturing the amplified target nucleic acids with respect to a binding member may also be performed in the second structure.

Determining a value indicative for the presence and/or amount of the captured target nucleic acids may be performed with the actuator actuated to deform the cover element. The cover element may be deformed in such a way that the volume of the second structure or central well or detection well is reduced. In such an embodiment, the volume of the second well may be re-increased after determining a value indicative for the presence and/or amount of the captured target nucleic acids.

According to another exemplary embodiment of the invention, a method is provided, comprising:
providing an amount of a reporter compound; a first binding member being configured to bind an anchor group of a capture molecule; a second binding member capable of capturing the reporter compound; an amount of a target nucleic acid capable of forming complexes with the reporter compound; the forming of complexes with a reporter compound inhibiting capturing of the reporter compound by the second binding member; and an amount of capture molecules wherein each capture molecule comprises a binding portion specific to a region of the target nucleic acids and an anchor group;
forming complexes each comprising a target nucleic acid and a capture molecule; contacting the complexes with the first binding member to bind the complexes to the first binding member;
releasing at least a subset of the amount of target nucleic acid from the first binding member;
forming complexes of a subset of the amount of a reporter compound with at least a subset of the amount of target nucleic acid;
capturing a remaining subset of the amount of reporter compound not in complex with a target nucleic acid on the second binding member; and
determining a value indicative for the presence and/or amount of reporter compound captured on the second binding member.

The reporter compound may comprise one or more detectable labels, e.g. two detectable labels. The one or more detectable labels may be fluorescent labels. Further, the reporter compounds may be oligonucleotides.

The method may further comprise determining a value indicative for the presence and/or amount of target nucleic acid based on the value indicative for the presence and/or amount of reporter compound captured on the second binding member.

The method may further comprise releasing the remaining subset of the amount of reporter compound from the second binding member after the step of determining a value indicative for the presence and/or amount of reporter compound captured on the second binding member; forming complexes of a subset of the amount of reporter compound with at least a subset of the amount of target nucleic acid; capturing a remaining subset of the amount of reporter compound not in complex with a target nucleic acid on the second binding member; and determining the value indicative for the presence and/or amount of reporter compound captured on the second binding member. In such an embodiment, the steps of releasing, forming complexes, capturing and determining may be performed N additional times, wherein N is an integer greater than or equal to 1, e.g. N≥5, N≥10 or N≥20.

Further, the step of forming complexes of a subset of the amount of reporter compound with at least a subset of the amount of target nucleic acid and the step of capturing a remaining subset of the amount of reporter compound not in complex with a target nucleic acid on the second binding member may be performed concomitantly.

The method may further comprise subjecting the target nucleic acid to amplification. In such an embodiment, amplification of the target nucleic acid may be initiated prior to the step of forming complexes of a subset of the amount of reporter compound with at least a subset of the amount of target nucleic acid.

The value indicative for the presence and/or amount of reporter compound captured on the second binding member may be determined before the steps of forming of complexes of a subset of the amount of reporter compound with at least a subset of the amount of target nucleic acid and of capturing a remaining subset of the amount of reporter compound not in complex with a target nucleic acid on the second binding member are in chemical equilibrium. Particularly, the value indicative for the presence and/or amount of reporter compound captured on the second binding member may be determined 1 s to 120 s after initiating the steps of forming complexes of a subset of the amount of reporter compound with at least a subset of the amount of target nucleic acid, and of capturing a remaining subset of the amount of reporter compound not in complex with a target nucleic acid on the second binding member.

The method may further comprise subjecting the target nucleic acids to reverse transcription prior to subjecting them to amplification.

The second binding member may comprise one or more different reporter specific capture molecules being capable of capturing a reporter compound on the second binding member. In such an embodiment, the capture molecules may be oligonucleotides. The different reporter specific capture molecules may be arranged on different locations with respect to the second binding member. Further, the reporter compounds may be captured on the second binding member by forming complexes with the reporter-specific capture molecules. At least a part of an interaction site of the reporter compound being capable of forming a complex with a target nucleic acid may also be capable of forming a complex with a reporter specific capture molecule. The reporter specific capture molecules and the target nucleic acid may compete for forming a complex with the reporter compound.

The amplification may comprise a step of denaturing double-stranded nucleic acids. Double-stranded nucleic acids may comprise complexes of reporter compounds with target nucleic acids, complexes of reporter compounds with reporter specific capture molecules, double strands of reporter compounds and double strands of target nucleic acids.

The amplification may further comprise a step of annealing primer molecules to target nucleic acids. In this embodiment, the annealing step may be performed concomitantly with the step of forming complexes of a subset of the amount of reporter compound with at least a subset of the amount of target nucleic acid and/or the step of capturing a remaining subset of the amount of reporter compound not in complex with a target nucleic acid on the second binding member.

The amplification may be a cyclic amplification, e.g. a PCR. Performing the PCR may comprise using a polymerase having exonuclease activity. The cyclic amplification may comprise at least 10 cycles or at least 20 cycles.

The value indicative for the presence and/or amount of reporter compound captured on the second binding member may be determined after at least one cycle, e.g. after each cycle, of the cyclic amplification. Further, the value indicative for the presence and/or amount of target nucleic acid may be determined each time after determining the value indicative for the presence and/or amount of reporter compound captured on the second binding member.

Determining the value indicative for the presence and/or amount of reporter compound captured on the second binding member may comprise time-dependent monitoring of the indicative value.

Further, the value indicative for the presence and/or amount of target nucleic acid may be determined based on a calibration curve correlating the value indicative for the presence and/or amount of reporter compound with a value indicative for the presence and/or amount of target nucleic acid.

The method of this exemplary embodiment may also be performed in a device as described above. E.g., the method may be performed in a device, comprising a rigid substrate; a flexible cover element at least partially covering the substrate; a first structure formed in the substrate, adapted for accommodating liquids and adapted for releasing contents of one or more cells, spores, or viruses, the contents including target nucleic acids; a second structure formed in the substrate, adapted for accommodating liquids and comprising at least one binding member adapted for capturing the target nucleic acids and for determining a value indicative for the presence and/or amount of the target nucleic acids; a microfluidic network interconnecting at least the first structure and the second structure; and an actuator unit adapted for effecting a fluid flow between the first structure and the second structure by pressing the flexible cover element against the substrate to selectively close a portion of the microfluidic network. The method may also be performed in a device, comprising a structure adapted for accommodating liquids, wherein the structure comprises at least one binding member and is in fluid communication with a microfluidic network; and a control unit adapted for controlling a fluid flow through the micro fluidic network in such a manner that target nucleic acids are captured at the at least one binding member, adapted for controlling an amplification of the target molecules in the structure, and adapted for controlling detection of compounds captured at the at least one binding member.

The device may further comprise a first structure adapted for accommodating liquids. In such an embodiment, the step of forming complexes each comprising a target nucleic acid and a capture molecule is performed in the first structure.

The device may further comprise a second structure adapted for accommodating liquids and the first and, optionally, the second binding member may be provided in the second structure. In such an embodiment, forming complexes each comprising a target nucleic acid and a capture molecule; contacting the complexes with the first binding member to bind the complexes to the first binding member; releasing at least a subset of the amount of target nucleic acid from the first binding member; forming complexes of a subset of the amount of a reporter compound with at least a subset of the amount of target nucleic acid;
capturing a remaining subset of the amount of reporter compound not in complex with a target nucleic acid on the second binding member; and determining a value indicative for the presence and/or amount of reporter compound captured on the second binding member is performed in the second structure, e.g. the central well.

Determining a value indicative for the presence and/or amount of the captured reporter compounds may be performed with the actuator actuated to deform the cover element. The cover element may be deformed in such a way that the volume of the central well or second structure or detection well is reduced. In such an embodiment, the volume of the central well may be increased again after determining a value indicative for the presence and/or amount of the captured reporter compounds.

Providing the one or more target nucleic acids may comprise providing a sample comprising the one or more target nucleic acids. The sample may be a liquid sample having a volume of 1 µl to 50 µl. Further, the sample may be a liquid whole blood sample.

The method may further comprise adding an amount of a quencher compound capable of forming complexes with the reporter compound not in complex with target molecules or reporter specific capture molecules. The quencher compound may comprise one or more moieties interfering with the generation of a detectable signal by a label (e.g., a quencher group "hijacking" the emissions that resulted from excitation of a fluorophor). E.g. the quencher groups may be capable of suppressing or inhibiting signals emitted by a detectable label of the reporter compound, e.g. a fluorescence signal. In such an embodiment, the quencher compound may be capable of forming complexes with the reporter compound not in complex with target molecules or reporter specific capture molecules such that the one or more quencher groups are in close proximity to the detectable label of the reporter compound within the complex.

The quencher compound may be an oligonucleotide. In this embodiment, the quencher oligonucleotide may comprise at least one specific sequence region which is complementary to a sequence region of a reporter oligonucleotide, thus allowing base-pairing between the quencher compound and the reporter compound.

The quencher group may include usual quenchers such as for instance Black Hole Quenchers (Biosearch Technologies), Qxl quenchers (AnaSpec) and Iowa black quenchers.

The quencher compounds may be provided in the second structure of a device as described above. In such an embodiment, the quencher compound may form a complex with a reporter compound not captured on the second binding member.

The second structure of a device as described above may be irreversibly sealed before initiating amplification of the target nucleic acids. Irreversibly sealing the second structure may be achieved by sealing (e.g. welding) an inlet and, optionally an outlet of the second structure, e.g. by heat-sealing channels and/or valves connected with the second structure.

According to another exemplary embodiment, a method is provided, comprising amplifying at least one target polynucleotide to form double-stranded amplicons, contacting the amplicons with a surface configured to selectively bind the amplicons (e.g., with an anchor group), and with the amplicons bound to the surface by an anchor group, optically determining the presence of the amplicons. The method may further comprise releasing the amplicons from the surface after the step of optically detecting, subjecting the released amplicons to at least one more amplification cycle, contacting the resulting amplicons with the surface, and with the amplicons bound to the surface by the anchor group, optically determining the presence of the amplicons. The method may further comprise performing the steps of releasing, subjecting, contacting, and optically determining a number N additional times, where N is an integer greater than or equal to 1. Particularly, $N \geq 5$, more particularly $N \geq 10$, and still more particularly $N \geq 20$.

The method may further comprise, prior to the step of amplifying, providing the target polynucleotides, forming complexes each comprising a target polynucleotide released from a pathogen and at least one capture molecule, each capture molecule comprising a binding portion specific to a region of the target polynucleotide and an anchor group, and contacting the complexes with the surface, the surface being configured to non-selectively bind the anchor group of the capture molecule to non-selectively bind the complexes and the surface. In such a method, providing the polynucleotides may comprise releasing contents of one or more cells, spores, or viruses, the contents including the target polynucleotides. The step of releasing may comprise contacting a sample comprising the one or more cells, spores, or viruses with a lysing reagent and the capture molecules. The step of contacting the sample with the lysing reagent and capture molecules may comprise contacting the sample with the lysing reagent and capture molecules in lyophilized form.

In such a method, the step of providing the target polynucleotides may include providing concomitant materials, and the method may further include separating the surface-bound complexes and the concomitant materials. In such a method, the concomitant materials may include contents of at least one cell, spore, or virus from which the polynucleotides have been released. The surface may be a surface of a particle.

According to another exemplary embodiment, a method is provided, comprising providing one or more target polynucleotides, forming complexes each comprising a target polynucleotide and at least one capture molecule, each capture molecule comprising a binding portion specific to a region of the target polynucleotide and an anchor group, and contacting the complexes with a surface, the surface being configured to non-selectively bind the anchor group of the capture molecule to non-selectively bind the complexes and the surface. In such a method, the step of providing may comprise releasing the contents of one or more cells, spores, or viruses and the contents comprises the polynucleotides. The method may further comprise separating the surface-bound complexes and other contents released from the one or more cells, spores, or viruses.

According to another exemplary embodiment, a method is provided, the method comprising forming a composition of matter comprising an amount of a reporter compound, a binding member capable of capturing the reporter compound, and an amount of a target nucleic acid capable of forming complexes with the reporter compound, the forming of complexes with the reporter compound inhibiting capturing of the reporter compound by the binding member; forming complexes of a subset of the amount of reporter compound with at least a subset of the amount of target nucleic acid; capturing a remaining subset of the amount of reporter compound not in complex with a target nucleic acid on the binding member; and determining a value indicative for the presence and/or amount of reporter compound captured on the binding member.

In other words, the method may comprise allowing a subset of the amount of reporter compound to form a complex with at least a subset of the amount of target nucleic acid, and allowing a remaining subset of the amount of reporter compound not in complex with a target nucleic acid to be captured on the binding member.

The method may be performed in a device selected from the group consisting of a biosensor assay device, a microfluidic cartridge, and a lab-on-chip.

In some embodiments, the method further comprises determining a value indicative for the presence and/or amount of target nucleic acid based on the value indicative for the presence and/or amount of reporter compound captured on the binding member. The determination of the value indicative for the presence and/or amount of reporter compound captured on the binding member may comprise time-dependent monitoring of the indicative value. In specific embodiments, the value indicative for the presence and/or amount of target nucleic acid is determined based on a calibration curve correlating the value indicative for the presence and/or amount of reporter compound with the value indicative for the presence and/or amount of target nucleic acid.

In other embodiments, the method further comprises releasing the remaining subset of the amount of reporter compound from the binding member after the steps of forming complexes of a subset of the amount of reporter compound with at least a subset of the amount of target nucleic acid, capturing a remaining subset of the amount of reporter compound not in complex with a target nucleic acid on the binding member, and determining a value indicative for the presence and/or amount of reporter compound captured on the binding member.

The steps of releasing, forming complexes, capturing, and determining a value indicative for the presence and/or amount of reporter compound and/or of target nucleic acid may be performed a number N additional times, where N is an integer greater than or equal to 1. In specific embodiments, N is ≥5, ≥10 or ≥20.

The method may further comprise, prior to the step of forming complexes: capturing at least a subset of the amount of reporter compound on the binding member; determining a value indicative for the presence and/or amount of reporter compound captured on the binding member; and releasing captured reporter compounds from the binding member.

In some embodiments, the step of forming complexes of a subset of the amount of reporter compound with at least a subset of the amount of target nucleic acid and the step of capturing a remaining subset of the amount of reporter compound not in complex with a target nucleic acid on the binding member are performed concomitantly.

In further embodiments, the method comprises subjecting the target nucleic acid to amplification. Amplification of the target nucleic acid may be initiated prior to the step of forming complexes of a subset of the amount of reporter compound with at least a subset of the amount of target nucleic acid.

The value indicative for the presence and/or amount of reporter compound captured on the binding member may be determined before the forming of complexes of a subset of the amount of reporter compound with at least a subset of the amount of target nucleic acid and the capturing of a remaining subset of the amount of reporter compound not in complex with a target nucleic acid on the binding member are in chemical equilibrium. In some embodiments, the value indicative is determined 1 s to 120 s after initiating the steps of forming complexes of a subset of the amount of reporter compound with at least a subset of the amount of target nucleic acid and of capturing a remaining subset of the amount of reporter compound not in complex with a target nucleic acid on the binding member.

The reporter compounds may comprise one or more detectable labels, e.g. two detectable labels. In specific embodiments, the one or more detectable labels are fluorescent labels. In other specific embodiments, the reporter compounds are oligonucleotides.

In other embodiments, the method further comprises subjecting the target nucleic acids to reverse transcription prior to subjecting them to amplification.

In other embodiments, the step of forming a composition of matter comprises forming a composition of matter comprising an amount of a first reporter compound, an amount of a first target nucleic acid capable of forming complexes with the first reporter compound, the forming of complexes with the first reporter compound inhibiting capturing of the first reporter compound by the binding member, an amount of a second reporter compound, and an amount of a second target nucleic acid capable of forming complexes with the second reporter compound, the forming of complexes with the second reporter compound inhibiting capturing of the second reporter compound by the binding member.

The binding member used in the method may comprise one or more different capture molecules being capable of capturing a reporter compound on the binding member. The capture molecules may also be denoted as reporter specific capture molecules. In specific embodiments, the capture molecules are oligonucleotides. The different capture molecules may also be arranged on different locations with respect to the binding member.

The reporter compounds may be captured on the binding member by forming complexes with the capture molecules. In specific embodiments, at least a part of an interaction site of the reporter compound being capable of forming a complex with a target nucleic acid is also capable of forming a complex with a capture molecule. In other specific embodiments, the capture molecules and the target nucleic acid compete for forming a complex with the reporter compound.

In other embodiments, the amplification comprises a step of denaturing double stranded nucleic acids. The double stranded nucleic acids may comprise complexes of reporter compounds with target nucleic acids, complexes of reporter compounds with capture molecules, double strands of reporter compounds, and double strands of target nucleic acids.

The amplification may also comprise a step of annealing primer molecules to target nucleic acids. The annealing step may be performed concomitantly with the step of forming complexes of a subset of the amount of reporter compound with at least a subset of the amount of target nucleic acid and/or with the step of capturing a remaining subset of the amount of reporter compound not in complex with a target nucleic acid on the binding member The amplification may be a cyclic amplification. In specific embodiments, the cyclic amplification is a PCR. The cyclic amplification may comprise at least 10 or at least 20 cycles. In other embodiments, performing the PCR comprises using a polymerase having exonuclease activity.

The value indicative for the presence and/or amount of reporter compound captured on the binding member may be determined after at least one cycle of the cyclic amplification. In specific embodiments, this value is determined after each cycle of the cyclic amplification. In other embodiments, the value indicative for the presence and/or amount of target nucleic acid is determined each time after determining the value indicative for the presence and/or amount of reporter compound captured on the binding member.

The method may further comprise adding an amount of a quencher compound capable of forming complexes with the reporter compound not in complex with target molecules or reporter specific capture molecules. The quencher compound may comprise one or more moieties interfering with the generation of a detectable signal by a label (e.g., a quencher group "hijacking" the emissions that resulted from excitation of a fluorophor). E.g. the quencher groups may be capable of suppressing or inhibiting signals emitted by a detectable label of the reporter compound, e.g. a fluorescence signal. In such an embodiment, the quencher compound may be capable of forming complexes with the reporter compound not in complex with target molecules or reporter specific capture molecules such that the one or more quencher groups are in close proximity to the detectable label of the reporter compound within the complex.

The quencher compound may be an oligonucleotide. In this embodiment, the quencher oligonucleotide may comprise at least one specific sequence region which is complementary to a sequence region of a reporter oligonucleotide, thus allowing base-pairing between the quencher compound and the reporter compound.

The quencher group may include usual quenchers such as for instance Black Hole Quenchers (Biosearch Technologies), Qxl quenchers (AnaSpec) and Iowa black quenchers.

According to another exemplary embodiment, a method is provided, the method comprising introducing a liquid whole blood sample into a device adapted for accommodating a sample in a fluid state; and determining a value indicative of the presence and/or amount of nucleic acids associated with a viral infection in the whole blood sample based on an analysis performed in the device. Particularly, the value determined may be indicative of the presence and/or amount of total nucleic acids associated with a viral infection. The volume of the whole blood sample introduced into the device may be 1 µl to 50 µl.

In some embodiments, the method further comprises determining a value indicative of the viral load in an infected patient based on the value indicative of the presence and/or amount of total nucleic acids associated with a viral infection.

In other embodiments, the fluid whole blood sample is introduced into the device directly from a patient. Particularly, the fluid whole blood sample may be obtained from a puncture at a fingertip of the patient. The method may further comprise contacting the blood obtained from the puncture at the fingertip with a capillary while the capillary remains in contact with the fingertip. In one embodiment, the method further comprises connecting the capillary to the device after contacting the capillary and the blood.

According to another exemplary embodiment, a method is provided, the method comprising providing a fluid sample having a volume of 1 µl to 50 µl; and determining a value indicative of the presence and/or amount of nucleic acids associated with a viral infection in the fluid sample. In some embodiments, the method further comprises introducing the fluid sample into a device adapted for accommodating a sample in a fluid state; and determining a value indicative of the presence and/or amount of nucleic acids associated with a viral infection in the fluid sample based on an analysis performed in the device. The value determined may be indicative of the presence and/or amount of total nucleic acids associated with a viral infection.

In some embodiments, the method further comprises determining a value indicative of the viral load in an infected patient based on the value indicative of the presence and/or amount of total nucleic acids associated with a viral infection.

In further embodiments, the fluid sample is a whole blood sample which may be an untreated whole blood sample. Furthermore, the volume of the fluid sample may be 1 µl to 10 µl.

In particular embodiments, the viral infection is an infection with HIV.

The device employed in embodiments of the methods may be adapted for detecting nucleic acids associated with a viral infection in a fluid sample. In further embodiments, the device is selected from the group consisting of a biosensor assay device, a micro-fluidic cartridge, and a lab-on-chip.

In some embodiments, the analysis performed in the device further comprises releasing nucleic acids from the sample, which may involve contacting the fluid sample with a lysing reagent.

The analysis may also comprise forming complexes, wherein each complex comprises a nucleic acid associated with a viral infection and a capture molecule, and wherein each capture molecule comprises an anchor group and a binding portion specific to a region of the nucleic acid associated with a viral infection.

In other embodiments, the analysis performed in the device further comprises contacting the complexes with a first binding member of the device, the first binding member being configured to bind the anchor group of the capture molecule and thus to bind the complexes to the first binding member. The step of forming complexes may be performed spatially separated from the step of contacting the complexes with the first binding member.

In some embodiments, the analysis performed in the device further comprises the amplification of the nucleic acids to be detected, typically by PCR. The amplified nucleic acids may be captured with respect to the first binding member.

The analysis may further comprise the provision of an amount of a reporter compound capable of forming complexes with the nucleic acid associated with a viral infection, and a second binding member capable of capturing the reporter compound, the forming of complexes with the nucleic acid inhibiting capturing of the reporter compound by the second binding member.

In some embodiments, the method also comprises forming complexes of a subset of the amount of reporter compound with at least a subset of the amount of nucleic acid associated with a viral infection; capturing a remaining subset of the amount of reporter compound not in complex with a nucleic acid associated with a viral infection on the second binding member; and determining a value indicative of the presence and/or amount of reporter compound captured on the second binding member; and, optionally, determining one or more values indicative for the amount of nucleic acids associated with a viral infection based on the value indicative of the amount of reporter compound.

Furthermore, the method may comprise subjecting the nucleic acids associated with a viral infection to amplification while allowing the reporter molecules to be released from the second binding member.

In another exemplary embodiment, the present invention is directed to the use of a method, as defined herein, for detecting HIV and/or for determining the HIV load in a patient.

In another exemplary embodiment, the present invention relates to the use of the amount of total viral nucleic acids as a diagnostic marker. In particular embodiments, the amount of total viral nucleic acids is determined by a method as described herein.

In other particular embodiments, the total viral nucleic acids used as a diagnostic marker are HIV nucleic acids. The amount of total HIV nucleic acids used as a marker may be indicative for detecting HIV, determining the HIV load in a patient, monitoring disease progression in a patient infected with HIV and/or monitoring the efficiency of antiviral treatment of a patient infected with HIV. The amount of total HIV nucleic acids may comprise nucleic acids originating from free and from cell-associated viruses, which, in turn, may comprise RNA originating from free viruses, RNA originating from cell-associated viruses, pro-viral DNA, reverse transcribed viral DNA, and transcribed pro-viral RNA.

A device may be provided which is configured to perform any one of the above described methods.

The aspects defined above and further aspects are apparent from the examples of embodiment to be described hereinafter and are explained with reference to these examples of embodiment.

BRIEF DESCRIPTION OF THE DRAWINGS

Exemplary embodiments will be described in more detail hereinafter but to which the invention is not limited. The illustration in the drawings is schematically. In different drawings, similar or identical elements are provided with the same reference signs.

FIG. 1a is a flow chart of a polynucleotide assay method according to an exemplary embodiment.

FIG. 1e shows an amplicon bound to a particle.

FIG. 2 is an assay device according to an exemplary embodiment suitable for use in the detection system of FIGS. 1b and 1c.

FIG. 3 is the assay device of FIG. 2 shown with a stencil actuator for operating the device.

FIG. 6 shows the effect of the amount of streptavidin sepharose slurry used to capture an oligonucleotide (i.e. HIV RNA) from a blood-lysis mixture, wherein the results of assays performed with 10 µl and 7 µl of streptavidin sepharose slurry reveal that binding capacity of 10 µl of slurry is sufficient to capture substantially all RNA molecules.

FIG. 14 shows fluorescent images of the detection of amplicons on strepavidin sepharose particles, wherein biotin-labelled amplicons were captured on strepavidin sepharose particles and visualized after hybridization of a fluorescently labelled probe to the captured amplicon.

FIG. 15 illustrates that the agarose gel electrophoresis shows that polynucleotides (i.e. HIV-RNA) captured on strepavidin sepharose particles can be used directly as a template for the amplification without further processing steps (i.e. elution, dilution or concentration).

FIG. 16 shows the respective fluorescent images of strepavidin sepharose particles, wherein more fluorescent strepavidin sepharose particles are detected in the positive probe as compared to the negative probe.

FIG. 17 schematically illustrates a device according to an exemplary embodiment.

FIG. 24 shows the principle (FIG. 24A) as well as the results (FIG. 24B) of an exemplary embodiment of an array-based competitive assay according to the present invention for determining the amount of HIV gag/env PCR product in a sample. FIG. 24C is a calibration curve showing the CT values plotted versus the respective DNA concentrations.

FIG. 25 illustrates different steps during the assay shown in FIG. 24. FIG. 25A is a schematic of the arrangement of the different spots on the array substrate. FIG. 25B is photographs of the array that were taken during amplification cycles 1, 12, 18 and 21, respectively.

FIG. 26B shows the PCR in the early exponential phase. FIG. 26C shows the PCR in the exponential phase. FIG. 26D shows the PCR at the plateau phase.

FIGS. 32 to 34 depict the respective plasma and whole blood viral loads of different HIV-positive patients receiving an antiviral therapy. FIG. 33A corresponds to patient #003. FIG. 33B corresponds to patient #004. FIG. 34A corresponds to patient #009. FIG. 34B corresponds to patient #066.

DETAILED DESCRIPTION

Figure 1B:
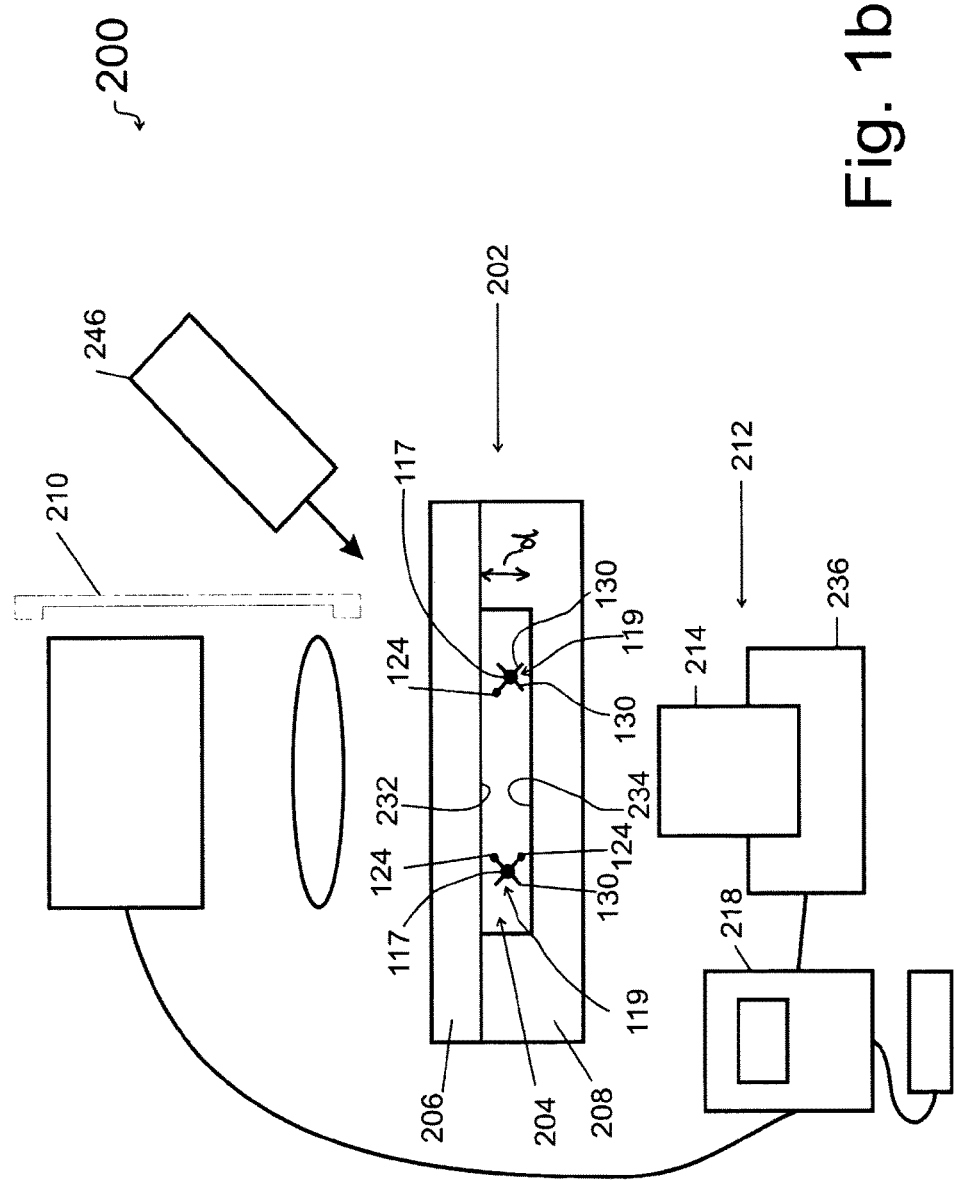
FIG. 1b is a view of a detection system useful in performing the method of FIG. 1a according to an exemplary embodiment.

Analysis of biological samples may include determining whether one or more polynucleotides (for instance, a DNA, RNA, mRNA, or rRNA) are present in the sample. For example, one may analyze a sample to determine whether a polynucleotide indicative of the presence of a particular pathogen is present.

According to an exemplary embodiment of the invention, a method for the analysis comprises forming complexes, each comprising a target nucleic acid and a capture molecule, wherein each capture molecule comprises a binding portion specific to a region of the target nucleic acid and an anchor group; contacting the complexes with a binding member, the binding member being configured to bind the anchor group of the capture molecule to bind the complexes to the binding member; subjecting one or more target nucleic acids to a amplification; capturing the amplified target nucleic acids with respect to the binding member; and determining a value indicative for the presence and/or amount of the captured target nucleic acids.

The term "target nucleic acid", as used herein, denotes any nucleic acid molecule that can be detected by using the method (i.e. target nucleic acids that are capable of forming complexes with a capture molecule; see below). Examples of such nucleic acid molecules include naturally occurring nucleic acids such as deoxyribonucleic acid (DNA) or ribonucleic acid (RNA) as well as artificially designed nucleic acids, e.g., nucleic acid analogs such as inter alia peptide nucleic acids (PNA) or locked nucleic acids (LNA), that are chemically synthesized or generated by means of recombinant gene technology (see, for example, Sambrook, J. et al. (1989) *Molecular, Cloning: A Laboratory Manual*, 2nd ed., Cold Spring Harbor Laboratory Press, Cold Spring Harbor, N.Y.). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, target nucleic acids are 10 to 10000 nucleotides in length, e.g., 20 to 2000 nucleotides, 30 to 1000 nucleotides or 50 to 500 nucleotides. As used herein, the term "nucleotide" is to be understood as referring to both ribonucleotides and deoxyribonucleotides (i.e. RNA and DNA molecules).

The target nucleic acid may be a nucleic acid associated with viral infections. A nucleic acid associated with viral infections denotes any nucleic acid molecule of viral origin (i.e. whose nucleotide sequence is identical or complementary to a corresponding sequence within the virus genome) that is present in a liquid sample to be analyzed that has been infected by one or more virus species. The viruses infecting the host, from which the liquid sample is obtained, may be any DNA virus (i.e. a virus having a DNA genome) or RNA virus (i.e. a virus having a RNA genome) (reviewed, e.g., in: Büchen-Osmond, C. (2003). *Taxonomy and Classification of Viruses*. In: Manual of Clinical Microbiology, 8th ed., vol. 2, p. 1217-1226, ASM Press, Washington D.C.). Examples of DNA viruses include inter alia the families of Papovaviridae (e.g. papillomavirus), Adenoviridae (e.g. adenovirus), and Herpesviridae (e.g. Epstein-Barr virus, cytomegalovirus). Examples of RNA viruses include inter alia the families of Picornaviridae (e.g. poliovirus, rhinovirus) Flaviviridae (e.g. hepatitis C virus), Filoviridae (e.g. Marburg virus, ebolavirus), and Retroviridae (e.g. human immunodeficiency virus (HIV)). In some embodiments of the invention, the nucleic acids to be detected are associated with infections caused by members of the Retroviridae, particularly they are associated with HIV infections. The term "HIV", as used herein, refers to both the HIV-1 and HIV-2 species and to any subtypes derived thereof.

Since many DNA viruses as well as the Retroviridae (notably, the replication of the Retroviridae generally requires reverse transcription of the RNA virus genome into DNA), can integrate their genetic information into the host cell's genome in form of a latent pro-virus, the term "nucleic acids associated with viral infections" does not only refer to nucleic acids originating from free and from cell-associated viruses but also to pro-viral DNA molecules being integrated into the host's genome, reverse transcribed viral DNA molecules (i.e. the "intermediates" of viral replication), and transcripts derived from pro-viral DNA (i.e. RNA molecules obtained by transcription of the host DNA genome).

Typically, the target nucleic acids are not subjected in isolated form to the method according to the invention but in form of a sample that is supposed to comprise one or more species of target nucleic acids. The term "one or more species", as used herein, refers to one or more different types of nucleic acids such as molecules having different nucleotide sequences and/or molecules descending from different origins (e.g., nucleic acids derived from different pathogens infecting a host cell).

The term "sample", as used herein, refers to any liquid, which is to be analyzed by using the invention, and which is supposed to comprise one or more species of target nucleic acids to be detected. Thus, a sample may comprise purified nucleic acid preparations dissolved in water or a suitable buffer (e.g. Tris/EDTA) as well as various biological samples. Examples of liquid samples that can be analyzed using the invention include inter alia organic and inorganic chemical solutions, drinking water, sewage, human and non-human body fluids such as whole blood, plasma, serum, urine, sputum, salvia or cerebrospinal fluid, cellular extracts from animals, plants or tissue cultures, prokaryotic and eukaryotic cell suspensions, phage preparations and the like.

The term "whole blood", as used herein, refers to blood with all its constituents. In other words, whole blood comprises both blood cells such as erythrocytes, leukocytes, and thrombocytes, and blood plasma in which the blood cells are suspended.

The sample may further comprise one or more additional agents such as diluents, solvents or buffers that may result from an optional purification and/or processing of the sample prior to subjecting it to the inventive method. However, in some embodiments of the invention, the sample analyzed is an untreated sample such as an untreated whole blood sample. The term "untreated", as used herein, is to be understood that after collecting the sample (e.g., by blood withdrawal from a patient) and before subjecting it to the inventive method no further sample processing (e.g., fractionation methods, drying/reconstitution, and the like) occurs.

A typical nucleic acid detection method involving such untreated samples is described below.

The volume of the fluid sample to be analyzed may be in the range of 1 µl to 50 µl, typically in the range of 1 µl to 45 µl or 1 µl to 40 µl or 1 µl to 30 µl or 1 µl to 25 µl or 1 µl to 20 µl or 1 µl to 15 µl. In particular embodiments, the volume of the fluid sample is in the range of 1 µl to 10 µl. However, in case whole blood samples are analyzed sample volumes exceeding 50 µl are within the scope of the invention as well.

The term "capture molecule", as used herein, denotes any molecule that shows a specific binding behavior and/or a characteristic reactivity, which makes it suitable for the formation of complexes with a target nucleic acid. Nucleic acids are typically used as capture molecules. Examples of nucleic acids that can be used as capture molecules include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, nucleic acid capture molecules are single-stranded oligonucleotides having a length of 10 to 150 nucleotides, e.g. of 20 to 100 nucleotides or 30 to 70 nucleotides. In specific embodiments, the capture molecules are used as primers in a PCR in order to amplify any target nucleic acid of interest being present in a given fluid sample.

In some embodiments, the capture molecules used in the invention may comprise at least one specific sequence region (i.e. the binding portion referred to above), which is complementary to a sequence region of a target nucleic acid (e.g., a nucleic acid associated with a viral infection), thus allowing base-pairing between the capture molecules and the nucleic acid to be detected. Typically, the specific binding region is at least 20 nucleotides in length, e.g. at least 30 nucleotides, or at least 40 nucleotides. Particularly, the nucleotide sequence of the binding region of the capture molecules is complementary to the corresponding nucleotide sequence of the target nucleic acid. As used herein, the term "nucleotide" is to be understood as referring to both ribonucleotides and deoxy-ribonucleotides (i.e. RNA and DNA molecules).

The capture molecules may be provided (e.g. in lyophilized or dried form) in one or more of the at least one structure adapted for accommodating liquids of the device as described above prior to the introduction of the fluid sample to be analyzed. Alternatively, the capture molecules may be introduced into the device along with the sample (i.e. concomitantly) or after the sample has already been introduced.

Within the scope of the invention one or more species of capture molecules may be employed. The term "one or more species" denotes one or more different types of capture molecules such as one or more nucleic acid molecules having different nucleotide sequences. More than one species of capture molecule concomitantly used are also referred to as "library". Such libraries comprise at least two but may also comprise many more different molecules, e.g. at least 5 different species, at least 10 different species, at least 30 different species and so forth. The libraries may also be present in form of array elements or any other spatial arrangement.

In some embodiments of the invention, the analysis performed in the device further comprises contacting the complexes comprising a target nucleic acid to be detected and a capture molecule with a binding member of the device, the binding member being configured to bind the anchor group of the capture molecule in order to bind the complexes to the binding member.

The terms "binding member" or "support member", as used herein, refers to any matrix, to which capture molecules, and thus also any complexes comprising such capture molecule, can be coupled via the anchor group of the capture molecules by covalent or non-covalent interactions. Examples of such matrices comprise inter alia the substrates of array elements or synthetic particles such as magnetic beads (e.g., paramagnetic polystyrol beads, also known as Dynabeads®) and latex beads as well as porous surfaces such as CPG and the like. Depending on the type of capture molecule, the type of anchor group, and the intended application, in each case a large variety of linkages are possible. For example, in case the anchor group of the capture molecules may be a biotin moiety, which may be coupled to an avidin or a streptavidin group being attached to the binding member. Alternatively, the capture molecules may comprise a stretch of adenosine residues (e.g. 10 adenosine residues) that will interact with a corresponding stretch of thymidine residues bound to the binding member. Specific coupling reagents including anchor groups are commercially available from different providers and well established in the art (see, for example, Sambrook, J. et al., supra; Ausubel, F. M. et al., supra, and Lottspeich, F., and Zorbas H., supra).

The binding member may be provided in one or more of the at least one structures of the device described above prior to the introduction of the fluid sample to be analyzed. Thereby, the binding member may be provided in the same one or more structures as the capture molecules or in at least one different structure. Typically, the step of forming complexes of capture molecules with target nucleic acids is performed spatially separated from the step of contacting the complexes with the binding member, i.e. in different structures or wells or reaction chambers of the device. E.g., the step of forming complexes of capture molecules with target nucleic acids is performed in the "lysis well" and the step of contacting the complexes with the binding member is performed in the "central well" referred to in FIG. 17. In such embodiments, capture molecules and the binding member are usually provided in different structures adapted for accommodating liquids. Instead of providing the binding member in the device prior to adding the sample, the binding member may be introduced into the device along with the sample (i.e. concomitantly) or after the sample has already been introduced.

In particular embodiments, the method further comprises subjecting the target nucleic acid to amplification, that is, to increase their amount present in the sample before subjecting the same to the further analysis in order to facilitate further detection. Typically, target nucleic acid amplification is achieved by means of a cyclic amplification. The cyclic amplification may comprise any number of amplification cycles that is equal or greater than two. Usually, cyclic amplification reaction comprises at least 10 or at least 20 cycles.

An exemplary cyclic amplification is a polymerase chain reaction (PCR). PCR is an established standard method in molecular biology that is described in detail, e.g., in Sambrook et al., supra; and in Ausubel, F. M. et al., supra. Typically, PCR is used for the amplification of double-stranded DNA molecules by employing a thermostable DNA polymerase. In some embodiments, the DNA polymerase used in the cyclic amplification has exonuclease activity, particularly 5'→3' exonuclease activity. Examples of such DNA polymerases include inter alia Taq DNA polymerase or Tth DNA polymerase (which are commercially available from multiple providers).

In case the target nucleic acid is a RNA molecule, the method of the invention may further comprise subjecting the target nucleic acid to reverse transcription (that is, to produce a DNA molecule from a corresponding RNA molecule) prior to subjecting them to amplification. Reverse transcription is another standard method in molecular biology and also described, e.g., in Sambrook et al., supra; and in Ausubel, F. M. et al., supra.

For this purpose, i.e. nucleic acid amplification, the device as described above may further comprise one or more temperature control units and/or temperature regulating units for controlling and/or regulating the temperature within the reaction chamber. Such a temperature control unit and/or temperature regulating unit may comprise one or more separate heating and/or cooling elements, which may directly contact one or more reaction chambers of the device. Typically, the one or more heating and/or cooling elements are made of a heat conductive material. Examples of such heat conductive materials include inter alia silicon, ceramic materials like aluminium oxide ceramics, and/or metals like high-grade steel, aluminium, copper, or brass. An exemplary detailed description of a temperature control unit and/or temperature regulating suitable for performing the present invention can also be found in the International Patent Application WO 01/02094, whose relevant contents are herewith explicitly referred to.

For example, controlling/regulating the temperature within a structure adapted for accommodating liquids may also be achieved by using a chamber body made of an electrically conductive material. The term "chamber body", as used herein, is understood to denote a solid body surrounding at least partially the at least one structure or reaction chamber of the device. The at least one structure may be at least in part an integral component of the chamber body (i.e. is made of the same material as the chamber body). Examples of electrically conductive materials include electrically conductive synthetic materials, such as polyamide with 5 to 30% carbon fibres, polycarbonate with 5 to 30% carbon fibres, polyamide with 2 to 20% stainless steel fibres, and polyphenylene sulfide with 5 to 40% carbon fibres. Furthermore, the chamber body may be designed to comprise swellings and diminutions, which allow specific heating of the reaction chamber or the corresponding surfaces.

The structure for accommodating liquids may be filled with a solution comprising the target nucleic acids to be amplified in such a manner that the pressure in the structure is increased. The pressure increase in the structure may force the flexible cover elements of the structure against the heating element and/or cooling element.

Measuring the temperature in the structure can be performed by various methods well established in the art, for example by using integrated resistance sensors, semi-conductor sensors, light waveguide sensors, polychromatic dyes or liquid crystals. Furthermore, the temperature in the reaction chamber can be determined by using an integrated temperature sensor in the chamber body, a pyrometer or an infrared sensor, or by measuring the temperature-dependent alteration of parameters such as the refraction index at the surface on which detection takes place or the pH value of the sample, for example by measuring the colour alteration of a pH-sensitive indicator.

Usually, amplification such as a PCR comprises three basic steps—denaturation, annealing of the primers, and extension of the primers—that are iteratively performed in a cyclic manner. However, the amplification may further comprise an initial denaturation step prior to the first "true" amplification cycle and/or a final extension step after completion of the final amplification cycle, respectively. In some embodiments, target nucleic acid amplification comprises (at least) a step of denaturing double-stranded nucleic acids and/or a combined step of annealing and extending the primer molecules at the target nucleic acids (i.e. a "two-step PCR").

Typically, the denaturation step involves the heating of the sample to be analyzed to a temperature of 94-95° C., typically for 0.5 s to 5 min, thus resulting in the strand-dissociation of double-stranded nucleic acid templates. Subjecting a sample to be analyzed to such denaturation step results in (i.e. allows) the simultaneous denaturation of the double stranded nucleic acids in the sample including double-stranded target nucleic acids and complexes of capture molecules with target nucleic acids (attached to the binding member), the latter resulting in the release of the target nucleic acids from the binding member.

Typically, the annealing step involves the cooling down of the sample to be analyzed to a temperature of 40-65° C., typically for 1 s to 5 min, to allow the association (i.e. the hybridization/base-pairing) of the primer molecules to the denaturated nucleic acid template strands. The reaction temperature employed depends on the chemical and/or physical properties of the primer molecules to be annealed such as their nucleotide sequence composition, melting temperature, their tendency for intra-molecular folding (e.g., the formation of double-stranded hairpin or turn structures), and the like. Within some embodiments of the present invention, subjecting a sample to be analyzed to such annealing step results in (i.e. allows) the re-association of double-stranded target molecules, and the forming of complexes of target nucleic acids with capture molecules, the latter resulting in the capturing or re-capturing of the target nucleic acids on the binding member. Thus, in some embodiments of the invention, the annealing step is performed concomitantly with the step of capturing target nucleic acids on the binding member by forming complexes with the capture molecules.

Finally, a typical extension step involves the extension of the hybridized primer molecules to produce full-length copies of the DNA template strands by a DNA polymerase. The length of the amplified DNA fragment is determined by the 5' ends of the pair of primers employed. Typically, the elongation step is performed at a temperature of 70-72° C. for 1 s to 10 min. Within some embodiments of the present invention, subjecting a sample to be analyzed to such extension step may result in the replication of the target nucleic acids to be analyzed by allowing the complexes of a primer with a target nucleic that have been formed during the annealing step to be extended to generate double-stranded amplified nucleic acid fragments optionally having incorporated a detectable marker that subsequently may be detected.

In some embodiments, e.g. for safety reasons, the central well or second structure may be irreversibly sealed prior to initiating amplification of the target nucleic acids. Irreversibly sealing the central well may be achieved by sealing an inlet and, optionally, an outlet of the central well. For instance, a channel and/or a value connected with the central well may be heat-sealed or welded. Plastics channels or valves e.g. may be heat-sealed by contacting a hot pin with the channel or valve so that the plastics are melted and the channel or valve is locked.

In specific embodiments, the method further comprises capturing the target nucleic acids that have been amplified, typically by subjecting the sample to be analyzed to PCR, with respect to the binding member (i.e. immobilizing the target nucleic acids thereon). As already described above, the target nucleic acids may be captured with respect to the binding member by forming complexes with the capture molecules which are still coupled to the binding member via the anchor group.

The method may further comprise releasing the captured amplified target nucleic acids from the binding member and repeating the steps of subjecting one or more target nucleic acids to amplification and capturing the amplified target nucleic acid with respect to the binding member. The term "releasing", as used herein, denotes the detachment or unbinding of the target nucleic acids from the binding member. This may be accomplished, for example, enzymatically via the cleavage of any covalent bonds or in cases, where the target nucleic acids are bound to the binding member by nucleic acid capture molecules via complementary base-pairing, by increasing the temperature in the structure, in which the assay is performed, thus resulting in nucleic acid strand separation (i.e. denaturation).

In such an embodiment, the cycle of releasing the captured amplified target nucleic acids from the binding member and repeating the steps of subjecting one or more target nucleic acids to amplification and capturing the amplified target nucleic acids with respect to the binding member may be performed at least 5 times, at least 10 times, at least 20 times, at least 30 times, at least 50 times or at least 100 times. The step of determining a value indicative for the presence and/or amount of the captured target nucleic acids may be performed after at least one cycle, e.g. after each cycle of releasing the captured amplified target nucleic acids from the binding member and repeating the steps of subjecting one or more target nucleic acids to amplification and capturing the amplified target nucleic acids with respect to the binding member.

Figure 18:
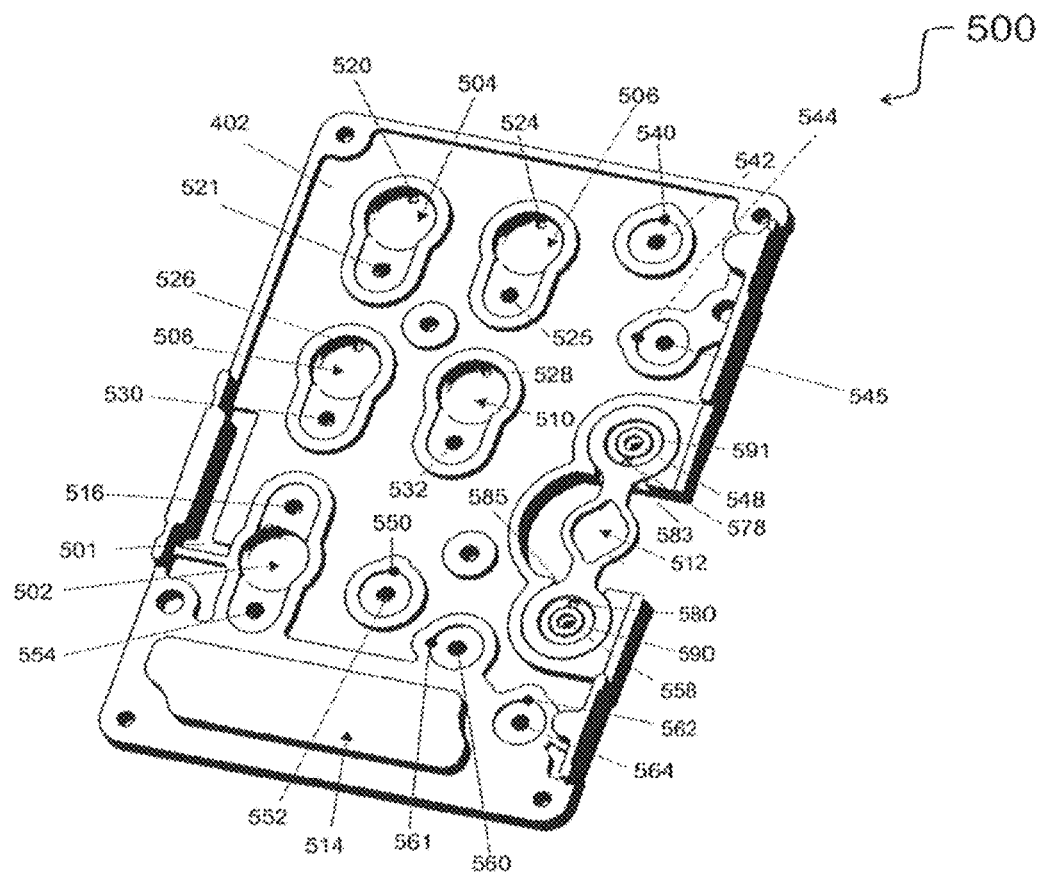
FIG. 18 illustrates a front side of a device according to another exemplary embodiment.
Figure 19:
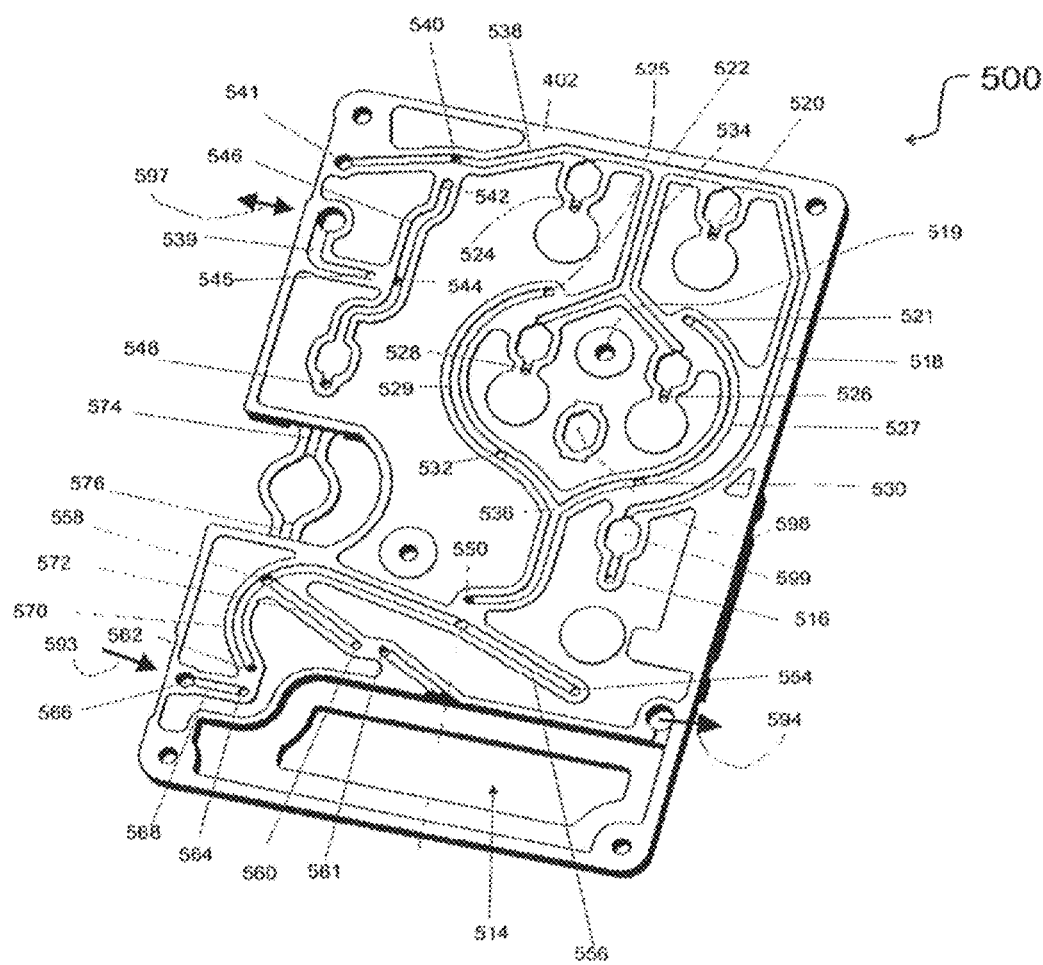
FIG. 19 illustrates a back side of the device of FIG. 18.

The step of forming complexes, each comprising a target nucleic acid and a capture molecule, wherein each capture molecule comprises a binding portion specific to a region of the target nucleic acid and an anchor group may be performed spatially separated from the step of contacting the complexes with a binding member, the binding member being configured to bind the anchor group of the capture molecule to bind the complexes to the binding member. In such an embodiment, the method is performed in a device which comprises at least two structures adapted for accommodating lipids. The at least two structures may be in fluid communication, e.g. with a microfluidic network. E.g., the method may be performed in device 500 as illustrated in FIGS. 18 and 19. The complexes each comprising a target nucleic acid and a capture molecule may be formed in the first structure 502. The complex may then be transferred to the second structure 512, in which the complexes are contacted with a binding member as described above which is configured to bind an anchor group of the capture molecule.

The term "determining a value indicative for the presence and/or amount of the captured target nucleic acids", as used herein, refers to the detection/determination of parameters such as electrical conductivity, redox potential, optical absorption, fluorescence intensity or bioluminescence that allow for qualitative and/or quantitative measurements of the target nucleic acids captured (or re-captured) on the binding member. Only one of these parameters may be determined but it is also possible to determine more than one parameter (e.g., electrical conductivity and the intensity of a fluorescence signal caused by a suitable label), either concomitantly or consecutively.

For performing the detection reaction, the target nucleic acids may be labelled with one or more detectable labels. The term "one or more detectable label", as used herein, refers to any compound or moiety that comprises one or more appropriate chemical substances or enzymes, which directly or indirectly generate a detectable compound or signal in a chemical, physical or enzymatic reaction. Such a label may thus be necessary for or will facilitate detection of the reporter compound of interest by being capable of forming interactions with said reporter compound. As used herein, the term is to be understood to include both detectable labels as such (also referred to as "markers") as well as any compounds coupled to one or more such detectable markers. Furthermore, moieties interfering with the generation of a detectable signal by a label (e.g., a quencher "hijacking" the emissions that resulted from excitation of the fluorophor, as long the quencher and the fluorophor are in close proximity to each other) may also belong to the detectable labels. The detectable labels may be incorporated or attached to the target nucleic acids, e.g., in form of modified and/or labelled ribonucleotides, deoxynucleotides or dideoxynucleotides.

Detectable markers or labels that may be used include any compound, which directly or indirectly generates a detectable compound or signal in a chemical, physical or enzymatic reaction. Labeling can be achieved by methods well known in the art (see, for example, Sambrook, J. et al., supra; and Lottspeich, F., and Zorbas H., supra). The labels can be selected inter alia from fluorescent labels, enzyme labels, colored labels, chromogenic labels, luminescent labels, radioactive labels, haptens, biotin, metal complexes, metals, and colloidal gold. All these types of labels are well established in the art. An example of a physical reaction that is mediated by such labels is the emission of fluorescence or phosphorescence upon irradiation or excitation or the emission of X-rays when using a radioactive label. Alkaline phosphatase, horseradish peroxidase, β-galactosidase, and β-lactamase are examples of enzyme labels, which catalyze the formation of chromogenic reaction products. In specific embodiments, the detectable labels are fluorescent labels. Numerous fluorescent labels are well established in the art and commercially available from different suppliers (see, for example, *The Handbook—A Guide to Fluorescent Probes and Labeling Technologies,* 10th ed. (2006), Molecular Probes, Invitrogen Corporation, Carlsbad, Calif., USA).

For detecting such labels, a detection system may be used which is suitable for determining values indicative for the presence and/or amount of reporter compound captured on a support member. The detection system may be connected to the device 500. Typically, the detection system is positioned opposite to one of the second structure 512, optionally opposite to a particular surface region where detection takes place. The selection of a suitable detection system depends on several parameters such as the type of labels used for detection or the kind of analysis performed. Various optical and non-optical detection systems are well established in the art. A general description of detection systems that can be used with the method can be found, e.g., in Lottspeich, F., and Zorbas H., supra.

Typically, the detection system is an optical detection system. In some embodiments, performing the method involves simple detection systems, which may be based on the measurement of parameters such as fluorescence, optical absorption, resonance transfer, and the like.

In further embodiments, detection systems are based on the comparison of the fluorescence intensities of spectrally excited nucleic acids labelled with fluorophores. Fluorescence is the capacity of particular molecules to emit their own light when excited by light of a particular wavelength resulting in a characteristic absorption and emission behavior. In particular, quantitative detection of fluorescence signals is performed by means of modified methods of fluorescence microscopy (for review see, e.g., Lichtman, J. W., and Conchello, J. A. (2005) *Nature Methods* 2, 910-919; Zimmermann, T. (2005) *Adv. Biochem. Eng. Biotechnol.* 95, 245-265). Thereby, the signals resulting from light absorption and light emission, respectively, are separated by one or more filters and/or dichroites and imaged on suitable detectors. Data analysis is performed by means of digital image processing. Image processing may be achieved with several software packages well known in the art (such as Mathematica Digital Image Processing, EIKONA, or Image-PRO). Another suitable software for such purposes is the Iconoclust software (Clondiag Chip Technologies GmbH, Jena, Germany).

Suitable detection systems may be based on "classical" methods for measuring a fluorescent signal such as epifluorescence or darkfield fluorescence microscopy (reviewed, e.g., in: Lakowicz, J. R. (1999) *Principles of Fluorescence Spectroscopy,* $2^{nd}$ ed., Plenum Publishing Corp., NY).

Another optical detection system that may be used is confocal fluorescence microscopy, wherein the object is illuminated in the focal plane of the lens via a point light source. Importantly, the point light source, object and point light detector are located on optically conjugated planes. Examples of such confocal systems are described in detail, for example, in Diaspro, A. (2002) *Confocal and 2-photon-* microscopy: Foundations, Applications and Advances, Wiley-Liss, Hobroken, N.J. The fluorescence-optical system is usually a fluorescence microscope without an autofocus, for example a fluorescence microscope having a fixed focus.

Further fluorescence detection methods that may also be used include inter alia total internal fluorescence microscopy (see, e.g., Axelrod, D. (1999) *Surface fluorescence microscopy with evanescent illumination*, in: Lacey, A. (ed.) *Light Microscopy in Biology*, Oxford University Press, New York, 399-423), fluorescence lifetime imaging microscopy (see, for example, Dowling, K. et al. (1999) *J. Mod. Optics* 46, 199-209), fluorescence resonance energy transfer (FRET; see, for example, Periasamy, A. (2001) *J. Biomed. Optics* 6, 287-291), bioluminescence resonance energy transfer (BRET; see, e.g., Wilson, T., and Hastings, J. W. (1998) *Annu. Rev. Cell Dev. Biol.* 14, 197-230), and fluorescence correlation spectroscopy (see, e.g., Hess, S. T. et al. (2002) *Biochemistry* 41, 697-705).

In specific embodiments, detection is performed using FRET or BRET, which are based on the respective formation of fluorescence or bioluminescence quencher pairs. The use of FRET is also described, e.g., in Liu, B. et al. (2005) *Proc. Natl. Acad. Sci. USA* 102, 589-593; and Szollosi, J. et al. (2002) *J. Biotechnol.* 82, 251-266. The use of BRET is detailed, for example, in Prinz, A. et al. (2006) *Chembiochem.* 7, 1007-1012; and Xu, Y. et al. (1999) *Proc. Natl. Acad. Sci. USA* 96, 151-156.

Determining one or more values indicative for the presence and/or amount of the captured target nucleic acids may comprise time-dependent monitoring of the one or more indicative values obtained (i.e. the repeated performing of the determination/detection step and monitoring the course of the indicative value over time).

The step of providing the target nucleic acids may comprise releasing the target nucleic acids from biological material comprised in the sample. To this end, the sample may be heated in order to destroy cellular membranes and/or viral capsids (e.g., by employing a temperature control unit and/or temperature regulating unit as described below). In some embodiments, this releasing step comprises contacting the fluid sample with a lysing reagent, for example a reagent comprising one or more detergents which disintegrate the cellular membranes and/or viral capsids. Such lysing reagents are well known in the art (see, for example, Sambrook, J. et al. (1989) *Molecular, Cloning: A Laboratory Manual*, 2nd ed., Cold Spring Harbor Laboratory Press, Cold Spring Harbor, N.Y.) and commercially available by many suppliers.

The method may further comprise separating the one or more target nucleic acids from concomitant material.

Providing the target nucleic acids may be performed spatially separated from the steps of contacting the complexes each comprising a target nucleic acid and a capture molecule with the binding member, subjecting the target nucleic acids to amplification, capturing the amplified target nucleic acids with respect to the binding member and determining a value indicative for the presence and/or amount of the captured target nucleic acids. E.g., the target nucleic acids may be provided in the same structure 502 in which the complexes each comprising a target nucleic acid and a capture molecule are formed.

In a further embodiment, the method is performed in a device as described above. For example, the device may comprise a first well 502 and the complexes each comprising a target nucleic acid and a capture molecule are formed in the first well 502. Further, the device may comprise a second well 512 and determining a value indicative for the presence and/or amount of the captured target nucleic acids may be performed in the second well 512 configured for detecting one or more target nucleic acids. The second well 512 may comprise a cover element covering the second well and an actuator unit adapted for being actuated to deform the cover element. Further, subjecting one or more target nucleic acids to amplification and/or (re-) capturing the amplified target nucleic acids with respect to the binding member may also be performed in the second well 512.

Determining a value indicative for the presence and/or amount of the captured target nucleic acids may be performed with the actuator actuated to deform the cover element. In such an embodiment, the cover element may be deformed in such a way that the volume of the detection well 512 is reduced. Further, the volume of the second well may be re-increased after determining the value indicative for the presence and/or amount of the captured target nucleic acids.

According to another exemplary embodiment of the invention, a method is provided, comprising
a) providing an amount of a reporter compound; a first binding member being configured to bind an anchor group of a capture molecule; a second binding member capable of capturing the reporter compound; an amount of a target nucleic acid capable of forming complexes with the reporter compound; the forming of complexes with a reporter compound inhibiting capturing of the reporter compound by the second binding member; an amount of capture molecules wherein each capture molecule comprises a binding portion specific to a region of the target nucleic acids and an anchor group;
b) forming complexes each comprising a target nucleic acid and a capture molecule;
c) contacting the complexes with the first binding member to bind the complexes to the first binding member;
d) releasing at least a subset of the amount of target nucleic acid from the first binding member;
e) forming complexes of a subset of the amount of a reporter compound with at least a subset of the amount of target nucleic acid;
f) capturing a remaining subset of the amount of reporter compound not in complex with a target nucleic acid on the second binding member; and
g) determining a value indicative for the presence and/or amount of reporter compound captured on the second binding member.

The term "reporter molecule" or "reporter compound", as used herein, denotes any molecule that is capable of forming complexes with one or more target nucleic acids and that can be captured on a support member, e.g. the second binding member, wherein the forming of complexes with the target nucleic acids inhibits the capturing of the reporter compound on the support member, e.g. the second binding member. Thereby, the term "capable of forming complexes", as used herein, refers to any interaction between a reporter molecules and a target nucleic acid. In other words, the term denotes the binding of the molecules to each other that may be accomplished via a common or different binding regions comprised in the reporter molecule that mediate the interaction with the target (such as via Watson-Crick base pairing between complementary nucleotide sequences). Typically, the interaction is reversible. Analogously, the term "being captured on a support member" or "being captured on the second binding member" also denotes any direct or indirect (for example, via capture molecules; see below) interaction of a reporter molecule with a given support member. This interaction is generally reversible as well.

In general, the reporter molecules may be nucleic acid molecules (i.e. RNA or DNA molecules as described above) having a length of 10 to 100 nucleotides, for example 15 to 50 nucleotides, 15 to 40 nucleotides or 20 to 30 nucleotides. Usually, the reporter molecules are single-stranded nucleic acid molecules (i.e. oligonucleotides). The reporter compound is configured such that the binding of such a reporter molecule to a target nucleic acid to be detected inhibits the capturing of the reporter molecule on the second binding member. The nucleic acid reporter molecules may comprise at least one specific binding region (herein also referred to as "interaction site") that is not only capable of interacting with the target nucleic acid (e.g., by binding to an at least partially complementary sequence region of the target nucleic acid, thus allowing, e.g., Watson-Crick base-pairing between the reporter molecule and the target nucleic acid to be detected), but also of being captured on the second binding member. Typically, the specific binding region comprised in the reporter molecule is at least 12 nucleotides in length, e.g. at least 15 nucleotides, at least 18 nucleotides or at least 22 nucleotides. In particular embodiments, the nucleotide sequence of the binding portion of the reporter molecules is complementary to the corresponding nucleotide sequence of the target nucleic acid.

One or more species of reporter molecules may be employed. The term "one or more species" denotes one or more different types of reporter molecules such as one or more nucleic acid molecules having different nucleotide sequences.

A "first binding member" as used herein may be a binding member as described above. E.g., a first binding member may refer to any solid matrix to which capture molecules, and thus also any complexes comprising such capture molecules, can be coupled via the anchor group of the capture molecules by covalent or non-covalent interactions. Examples of such matrices comprise inter alia synthetic particles such as magnetic beads (e.g., paramagnetic polystyrol beads, also known as Dynabeads®) and latex beads.

A "second binding member", as used herein, may be a binding member as described above. E.g., a second binding member refers to any solid matrix, on which the reporter molecules can be captured either directly (e.g., via an anchor group comprised in the reporter molecule) or in an indirect manner via one or more species of reporter specific capture molecules capable of capturing a reporter molecule to the second binding member by covalent or non-covalent interactions. Examples of second binding members that can be used comprise inter alia the substrates of array elements (e.g., microscope slides, wafers or ceramic materials).

The term "reporter specific capture molecule", as used herein, denotes any molecule being e.g. attached to or immobilized on the second binding member that shows a specific binding behavior and/or a characteristic reactivity, which makes it suitable for the formation of complexes with a reporter molecule (i.e. the binding to the reporter molecule). Nucleic acids are typically used as capture molecules. Examples of nucleic acids that can be used as reporter specific capture molecules include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, reporter specific capture molecules are single-stranded oligonucleotides having a length of 10 to 100 nucleotides, e.g. of 15 to 50 nucleotides or 20 to 30 nucleotides.

The reporter specific capture molecules may comprise at least one specific sequence region (i.e. the binding region), which is configured to bind a reporter molecule, for example, to interact with a complementary sequence region of a reporter molecule via base-pairing between the reporter specific capture molecules and the nucleic acid to be detected. Typically, the specific binding region is at least 12 nucleotides in length, e.g. at least 15 nucleotides, at least 18 nucleotides or at least 22 nucleotides. In particular embodiments, the nucleotide sequence of the binding region of the reporter specific capture molecules is complementary to the corresponding nucleotide sequence of the reporter molecule.

In some embodiments, at least a part of an interaction site of the reporter compound being capable of forming a complex with a target nucleic acid is also capable of forming a complex with a reporter specific capture molecule. In other words, the reporter specific capture molecules and the target nucleic acids compete for forming a complex with the reporter compound, that is, the respective binding regions comprised in the reporter specific capture molecules and the target nucleic acids recognize the same or at least similar corresponding sequence(s) of a reporter molecule. The term "similar sequences", as used herein, denotes sequences that differ only in one or more single nucleotide mismatches (i.e. non-complementary pairs of nucleotides) or by one or more single nucleotide additions, insertions or deletions (i.e. additional or lacking nucleotide residues). Thus, the respective binding regions comprised in the reporter specific capture molecules and the target nucleic acids are at least partially identical. The term "partially identical", as used herein, denotes sequences differing only in one or more single nucleotides, as described above, or sequences having overlapping binding sites, i.e. sequences sharing a common nucleotide sequence but differ in at least one other part of the sequence region. However, it is also possible that the respective binding regions comprised in the reporter specific capture molecules and the target nucleic acids recognize different, non-overlapping (e.g., adjacent) sequences of a reporter molecule but binding of either the reporter specific capture molecule or the target nucleic acid to the reporter molecule sterically interferes with the binding of the other one.

In some embodiments, the chemical equilibrium between the steps of forming of complexes of reporter compound and target nucleic acid on the one hand and capturing of reporter compound on the second binding member (e.g. by forming complexes with a reporter specific capture molecule) on the other hand may be influenced by varying the degree of similarity and/or partial identity of the sequences of the reporter specific capture molecule (with respect to the reporter compound sequences) and the reporter compound (with respect to the target nucleic acid, respectively, as described above.

For instance, the reporter specific capture molecule sequences may be selected such that the binding region with respect to the reporter compound sequence is shorter or longer than that of the binding region of the reporter compound sequence with respect to the target nucleic acid sequence. In this way, the binding affinity of the reporter compound with respect to the target nucleic acid compared to that of the reporter compound with respect to the reporter specific capture molecule may be increased or decreased.

One or more species of reporter specific capture molecules may be employed. The term "one or more species" denotes one or more different types of reporter specific capture molecules such as one or more nucleic acid molecules having different nucleotide sequences. More than one species of reporter specific capture molecule concomitantly used are also referred to as "library". Such libraries comprise at least two but may also comprise many more different molecules, e.g. at least 10 different species, at least 20 different species, at least 50 different species and so forth. The libraries may also be arranged on different locations with respect to the second binding member. For example, they may be present in form of arrays or any other spatial arrangement.

The term "array" (also referred to as "microarray"), as used herein, refers to a defined spatial arrangement (layout) of capture molecules such as reporter specific capture molecules on a binding member, e.g. the second binding member (also referred to as "substrate"), wherein the position of each molecule within the array is determined separately. Typically, the microarray comprises defined sites or predetermined regions, i.e. so-called "array elements" or "spots", which may be arranged in a particular pattern, wherein each array element typically comprises only one species of capture molecules. The arrangement of the capture molecules such as reporter specific capture molecules on the support, e.g. the second binding member can be generated by means of covalent or non-covalent interactions. However, the capture molecules may also be directly immobilized within the reaction chamber of a device used for performing the method (see below).

A "target nucleic acid" may be a target nucleic acid as described above. E.g., the target nucleic acid may be a nucleic acid associated with viral infections such as HIV.

Typically, the target nucleic acids are not subjected in isolated form to the method according to the invention but in form of a sample as described above that is supposed to comprise one or more species of target nucleic acids. The term "one or more species", as used herein, refers to one or more different types of nucleic acids such as molecules having different nucleotide sequences and/or molecules descending from different origins (e.g., nucleic acids derived from different pathogens infecting a host cell).

The term "sample", as used herein, refers to any liquid sample as described above. Examples of liquid samples that can be analyzed include inter alia human and non-human body fluids such as whole blood. In some embodiments of the invention, the sample analyzed is an untreated sample such as an untreated whole blood sample as described above. The volume of the fluid sample to be analyzed may be in the range of 1 µl to 50 µl, typically in the range of 1 µl to 45 µl or 1 µl to 40 µl or 1 µl to 30 µl or 1 µl to 25 µl or 1 µl to 20 µl or 1 µl to 15 µl. In particular embodiments, the volume of the fluid sample is in the range of 1 µl to 10 µl. However, in case whole blood samples are analyzed sample volumes exceeding 50 µl are within the scope of the invention as well.

The term "determining a value indicative for the presence and/or amount of reporter compound captured on the second binding member", as used herein, refers to the detection/determination of parameters such as electrical conductivity, redox potential, optical absorption, fluorescence intensity or bioluminescence that allow for qualitative and/or quantitative measurements of the reporter molecules captured (or re-captured) on the second binding member. Only one of these parameters may be determined but it is also possible to determine more than one parameter (e.g., electrical conductivity and the intensity of a fluorescence signal caused by a suitable label), either concomitantly or consecutively.

In some embodiments, the method further comprises determining a value indicative for the presence and/or amount of target nucleic acid based on the value indicative for the presence and/or amount of reporter compound captured on the second binding member. That is, the presence and/or amount of the one or more target nucleic acids present in a particular sample may be calculated based on the difference between the presence and/or amount of reporter compound being present prior to the forming of target nucleic acid/reporter molecule complexes and the amount of reporter compound being captured on the second binding member after said complex formation.

For performing the detection reaction, the reporter compound may comprise one or more detectable labels as described above. For instance, the reporter compound may comprise two detectable labels. In specific embodiments, the detectable labels are fluorescent labels. Numerous fluorescent labels are well established in the art and commercially available from different suppliers (see, for example, *The Handbook—A Guide to Fluorescent Probes and Labeling Technologies*, 10th ed. (2006), Molecular Probes, Invitrogen Corporation, Carlsbad, Calif., USA).

For detecting such labels, the device used for performing the method may further comprise a detection system suitable for determining values indicative for the presence and/or amount of reporter compound captured on the second binding member. E.g., a detection system suitable for determining values indicative for the presence and/or amount of target nucleic acids captured on a binding member as described above may be used.

In some embodiments, the method further comprises releasing the remaining subset of the amount of reporter compound from the second binding member after the steps of forming complexes of a subset of the amount of reporter compound with at least a subset of the amount of target nucleic acid, capturing a remaining subset of the amount of reporter compound not in complex with a target nucleic acid on the second binding member, and determining the value indicative for the presence and/or amount of reporter compound captured on the second binding member. The term "releasing", as used herein, denotes the detachment or unbinding of the reporter molecules from the second binding member. This may be accomplished, for example, enzymatically via the cleavage of any covalent bonds or in cases, where the nucleic acid reporter molecules are bound to the second binding member by reporter specific nucleic acid capture molecules via complementary base-pairing, by increasing the temperature in the structure, in which the assay is performed, thus resulting in nucleic acid strand separation (i.e. denaturation).

In further embodiments, the steps of releasing, forming complexes, capturing, and determining are repeated N additional times, where N is an integer greater than or equal to 1. In other words, the method is performed in a cyclic manner. In specific embodiments, the integer N is ≥5, ≥10 or ≥20.

Further, the step of forming complexes of a subset of the amount of reporter compound with at least a subset of the amount of target nucleic acid and the step of capturing a remaining subset of the amount of reporter compound not in complex with a target nucleic acid on the second binding member may be performed concomitantly.

In particular embodiments, the method further comprises subjecting the target nucleic acids to amplification, that is, to increase their amount present in the sample before subjecting the same to the further analysis in order to facilitate further detection. Typically, target nucleic acid amplification is achieved by means of a cyclic amplification. The cyclic amplification may comprise any number of amplification cycles that is equal or greater than two. Usually, cyclic amplification reaction comprises at least 10 or at least 20 cycles.

An exemplary cyclic amplification is a polymerase chain reaction (PCR) as described above. Typically, PCR is used for the amplification of double-stranded DNA molecules by employing a thermostable DNA polymerase. In some embodiments, the DNA polymerase used in the cyclic amplification has exonuclease activity, particularly 5'→3' exonuclease activity. Examples of such DNA polymerases include inter alia Taq DNA polymerase or Tth DNA polymerase (which are commercially available from multiple providers). By means of this 5'→3' exonuclease activity the DNA polymerase may nucleolytically attack the labelled 5'-termini of reporter molecules that are bound to the target nucleic acids resulting in a progressive degradation of such reporter molecules. As a result, the amount of reporter compound that is captured on the second binding member additionally decreases during each cycle of the amplification reaction. Optionally, the DNA polymerase employed may also exhibit 3'→5' exonuclease activity ("proofreading activity") for removing an incorrect nucleotide that has been added to the nascent DNA strand at a particular sequence position. Examples of such DNA polymerases having both exonuclease activities include inter alia Pwo DNA polymerase, and Pfu DNA polymerase (both enzymes are also commercially available from various suppliers). If the target nucleic acid is a RNA molecule, the method may further comprise subjecting the target nucleic acid to reverse transcription as described above prior to subjecting them to amplification.

Amplification of the target nucleic acid may be initiated prior to the step of forming complexes of a subset of the amount of reporter compound with at least a subset of the amount of target nucleic acid. That is, the target nucleic acid is subjected to amplification while allowing reporter compounds to form a complex with a target nucleic acid, and reporter compounds not in complex with a target nucleic acid to be re-captured on the second binding member.

For this purpose, i.e. nucleic acid amplification, a device 500 as illustrated in FIGS. 18 and 19 may be used for performing the method which may further comprise one or more temperature control units and/or temperature regulating units as described above for controlling and/or regulating the temperature within the structure or reaction chamber, e.g. the central well 502.

The structure for accommodating liquids may be filled with a solution comprising the target nucleic acids to be amplified in such a manner that the pressure in the structure is increased, whereby the pressure increase in the structure forces the one or more flexible cover elements of the structure against the heating element and/or cooling element. For instance, for performing amplification of the nucleic acid targets the structure may be filled such that the one or more flexible cover elements carry out a convex bending thus pressing the one or more cover elements against the heating element and/or cooling element and allowing for an efficient thermal conductance.

Measuring the temperature in the reaction chamber can be performed as described above.

Usually, amplification such as a PCR comprises three basic steps—denaturation, annealing of the primers, and extension of the primers—that are iteratively performed in a cyclic manner. However, the amplification may further comprise an initial denaturation step prior to the first "true" amplification cycle and/or a final extension step after completion of the final amplification cycle, respectively. In some embodiments of the method, target nucleic acid amplification comprises (at least) a step of denaturing double-stranded nucleic acids and/or a combined step of annealing and extending the primer molecules at the target nucleic acids (i.e. a "two-step PCR").

The denaturation step involves the heating of the sample to be analyzed to a temperature of 94-95° C., typically for 0.5 s to 5 min, thus resulting in the strand-dissociation of double-stranded nucleic acid templates. Subjecting a sample to be analyzed to such denaturation step may further result in (i.e. allow) the simultaneous denaturation of the double stranded nucleic acids in the sample including double-stranded target molecules, double-stranded reporter molecules, complexes of reporter compounds with target nucleic acids, and complexes of reporter compounds with reporter specific capture molecules (attached to the second binding member), the latter resulting in the release of the reporter compounds from the second binding member.

The annealing step involves the cooling down of the sample to be analyzed to a temperature of 40-65° C., typically for 1 s to 5 min, to allow the association (i.e. the hybridization/base-pairing) of the primer molecules to the denaturated nucleic acid template strands. The reaction temperature employed depends on the chemical and/or physical properties of the primer molecules to be annealed such as their nucleotide sequence composition, melting temperature, their tendency for intra-molecular folding (e.g., the formation of double-stranded hairpin or turn structures), and the like. Subjecting a sample to be analyzed to such annealing step may further result in (i.e. allow) the re-association of double-stranded target molecules, the re-association of double-stranded reporter molecules, the forming of complexes of reporter compounds with nucleic acid targets, and the forming of complexes of reporter compounds not in complex with a target nucleic acid with reporter specific capture molecules, the latter resulting in the capturing or re-capturing of the reporter compounds on the second binding member. Thus, in some embodiments, the annealing step is performed concomitantly with the step of forming complexes of a subset of the amount of reporter compound with at least a subset of the amount of target nucleic acid and/or the step of capturing a remaining subset of the amount of reporter compound not in complex with a target nucleic acid on the second binding member.

Finally, the extension step involves the extension of the hybridized primer molecules to produce full-length copies of the DNA template strands by a DNA polymerase. The length of the amplified DNA fragment is determined by the 5' ends of the pair of primers employed. Typically, the elongation step is performed at a temperature of 70-72° C. for 1 s to 10 min. Subjecting a sample to be analyzed to such extension step may further result in the replication of the target nucleic acids to be analyzed by allowing the complexes of a subset of the amount of reporter compound with at least a subset of the amount of target nucleic that have been formed during the annealing step to be extended to generate double-stranded amplified nucleic acid fragments having incorporated an optionally labelled reporter compound that subsequently may be detected.

In some embodiments, e.g. for safety reasons, the central well or second structure may be irreversibly sealed prior to initiating amplification of the target nucleic acids. Irreversibly sealing the central well may be achieved by sealing an inlet and, optionally, an outlet of the central well. For instance, a channel and/or a value connected with the central well may be heat-sealed or welded. Plastics channels or valves may be heat-sealed by contacting a hot pin with the channel or valve so that the plastics are melted and the channel or valve is locked.

For performing the detection reaction, the reporter compounds may be labelled with one or more detectable labels as described above, e.g. fluorescent labels. The detectable labels may be incorporated or attached to the reporter molecules, e.g., in form of modified and/or labelled ribonucleotides, deoxynucleotides or dideoxynucleotides. For detecting such labels, detections systems as described above, e.g. optical detection systems, may be used.

The detection/determination of a value indicative for the presence and/or amount of the target nucleic acids may be performed only once or more than once during the assay performed. In case, more than one detection step during a single assay is performed, in some embodiments the mean value of the results obtained may be calculated. The data obtained in one or more cycles of detection may be analyzed and mathematically processed using appropriate computer software known by persons skilled in the art in order to determine inter alia the presence, the length or the sequence of one or more target nucleic acids and/or to calculate its/their amount.

In some embodiments, particularly if the reporter compound is in excess of the target nucleic acid, the value indicative for the presence and/or amount of reporter compound captured on the second binding member is determined before the forming of complexes of a subset of the amount of reporter compound with at least a subset of the amount of target nucleic acid and the capturing of a remaining subset of the amount of reporter compound not in complex with a target nucleic acid on the second binding member are in chemical equilibrium. For example, the determination/detection step is performed during the annealing step of an amplification reaction. However, it is also possible to perform the determination/detection reaction after completion of the annealing step (i.e. during or after completion of the elongation step).

In a further embodiment, the value indicative for the presence and/or amount of reporter compound captured on the second binding member is determined 1 s to 120 (e.g., 1, 5, 10, 15, 20, 30, 60 or 120 s) after initiating the steps of forming complexes of a subset of the amount of reporter compound with at least a subset of the amount of target nucleic acid and of capturing a remaining subset of the amount of reporter compound not in complex with a target nucleic acid on the second binding member.

In other embodiments, the value indicative for the presence and/or amount of reporter compound captured on the second binding member is determined after at least one cycle of the cyclic amplification comprising denaturation, annealing, and elongation steps, e.g., during or after completion of the annealing step. In specific embodiments, said value is determined after each cycle of the cyclic amplification. In other specific embodiments, the value indicative for the presence and/or amount of target nucleic acid is determined each time after determining the value indicative for the presence and/or amount of reporter compound captured on the second binding member.

In some embodiments, determining the value indicative for the presence and/or amount of reporter compound captured on the second binding member comprises time-dependent monitoring of the indicative value (i.e. the repeated performing of the determination/detection step and monitoring the course of the indicative value over time).

In further embodiments, the value indicative for the presence and/or amount of target nucleic acid is determined based on a calibration curve correlating the value indicative for the presence and/or amount of reporter compound with the value indicative for the presence and/or amount of target nucleic acid.

The method may be performed in a device as described above comprising a structure adapted for accommodating liquids, wherein the structure comprises at least one binding member and is in fluid communication with a microfluidic network; and a control unit adapted for controlling a fluid flow through the microfluidic network in such a manner that target molecules are captured at the at least one binding member, adapted for controlling an amplification of the target molecules in the structure, and adapted for controlling detection of compounds captured at the at least one binding member. E.g., the method may be performed in a device comprising a rigid substrate; a flexible cover element at least partially covering the substrate; a first structure formed in the substrate, adapted for accommodating liquids and adapted for releasing contents of one or more cells, spores or viruses, the contents including target molecules; a second structure formed in the substrate, adapted for accommodating liquids and comprising at least one binding member adapted for capturing the target molecules and for determining a value indicative for the presence and/or amount of the target molecules; a micro fluidic network interconnecting at least the first structure and the second structure; and an actuator unit adapted for effecting a fluid flow between the first structure and the second structure by pressing the flexible cover element against the substrate to selectively close a portion of the microfluidic network.

E.g., a device 500 may be used which comprises a first well 502. In such an embodiment, the step of forming complexes each comprising a target nucleic acid and a capture molecule is performed in the first well.

The device 500 may comprise a second well 512. In such an embodiment, the first binding member and the second binding member are provided in the second well and the steps of contacting the complexes with the first binding member to bind the complexes to the first binding member; releasing at least a subset of the amount of target nucleic acid from the first binding member; forming complexes of a subset of the amount of a reporter compound with at least a subset of the amount of target nucleic acid; capturing a remaining subset of the amount of reporter compound not in complex with a target nucleic acid on the second binding member; and determining a value indicative for the presence and/or amount of reporter compound captured on the second binding member are performed in the second well.

Determining a value indicative for the presence and/or amount of the captured reporter compounds may be performed with the actuator actuated to deform the cover element. The cover element may be deformed in such a way that the volume of the central well or second structure or detection well is reduced. In such an embodiment, the volume of the central well may be increased again after determining a value indicative for the presence and/or amount of the captured reporter compounds.

The method may further comprise adding an amount of a quencher compound capable of forming complexes with the reporter compound not in complex with target molecules or reporter specific capture molecules. The quencher compound may comprise one or more moieties interfering with the generation of a detectable signal by a label (e.g., a quencher group "hijacking" the emissions that resulted from excitation of a fluorophor). For example, the quencher groups may be capable of suppressing or inhibiting signals emitted by a detectable label of the reporter compound, e.g. a fluorescence signal. In such an embodiment, the quencher compound may be capable of forming complexes with the reporter compound not in complex with target molecules or reporter specific capture molecules such that the one or more quencher groups are in close proximity to the detectable label of the reporter compound within the complex.

The quencher compound may be an oligonucleotide. In this embodiment, the quencher oligonucleotide may comprise at least one specific sequence region which is complementary to a sequence region of a reporter oligonucleotide, thus allowing base-pairing between the quencher compound and the reporter compound.

The quencher group may include usual quenchers such as for instance Black Hole Quenchers (Biosearch Technologies), Qxl quenchers (AnaSpec) and Iowa black quenchers.

The quencher compounds may be provided in the second structure of a device as described above. In such an embodiment, the quencher compound may form a complex with a reporter compound not captured on the second binding member.

The second structure of a device as described above may be irreversibly sealed before initiating amplification of the target nucleic acids. Irreversibly sealing the second structure may be achieved by sealing (e.g. welding) an inlet and, optionally an outlet of the second structure, e.g. by heat-sealing channels and/or valves connected with the second structure.

According to another exemplary embodiment of the invention the method comprises:
forming a composition of matter comprising:
an amount of a reporter compound,
a binding member capable of binding the reporter compound, and
an amount of a target nucleic acid capable of binding the reporter compound, the binding of the target nucleic acid to the reporter compound inhibiting binding of the reporter compound to the binding member;
binding a subset of the amount of reporter compound with at least a subset of the amount of target nucleic acid;
binding a remaining subset of the amount of reporter compound not in complex with a target nucleic acid on the binding member; and
determining a value indicative for the presence and/or amount of reporter compound bound to the binding member.

The term "target nucleic acid", as used herein, denotes any nucleic acid molecule that can be detected by using the method (i.e. target nucleic acids that are capable of forming complexes with a reporter compound; see below). Examples of such nucleic acid molecules include naturally occurring nucleic acids such as deoxyribonucleic acid (DNA) or ribonucleic acid (RNA) as well as artificially designed nucleic acids, e.g., nucleic acid analogs such as inter alia peptide nucleic acids (PNA) or locked nucleic acids (LNA), that are chemically synthesized or generated by means of recombinant gene technology (see, for example, Sambrook, J. et al. (1989) Molecular, Cloning: A Laboratory Manual, 2nd ed., Cold Spring Harbor Laboratory Press, Cold Spring Harbor, N.Y.). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, target nucleic acids are 10 to 10000 nucleotides in length, e.g., 20 to 2000 nucleotides, 30 to 1000 nucleotides or 50 to 500 nucleotides. As used herein, the term "nucleotide" is to be understood as referring to both ribonucleotides and deoxyribonucleotides (i.e. RNA and DNA molecules).

Typically, the target nucleic acids are not provided in isolated form to the method but in form of a sample that is supposed to comprise one or more species of target nucleic acids. The term "one or more species", as used herein, refers to one or more different types of nucleic acids such as molecules having different nucleotide sequences and/or molecules descending from different origins (e.g., nucleic acids derived from different pathogens infecting a host cell).

The term "sample", as used herein, refers to any liquid, which is to be analyzed by using the method, and which is supposed to comprise one or more species of target nucleic acids to be detected. Thus, the term sample comprises purified nucleic acid preparations dissolved in water or a suitable buffer (e.g. Tris/EDTA) as well as various biological samples. Examples of liquid samples that can be analyzed using the method include inter alia organic and inorganic chemical solutions, drinking water, sewage, human and non-human body fluids such as whole blood, plasma, serum, urine, sputum, salvia or cerebrospinal fluid, cellular extracts from animals, plants or tissue cultures, prokaryotic and eukaryotic cell suspensions, phage preparations and the like.

The sample may further comprise one or more additional agents such as diluents, solvents or buffers that may result from an optional purification and/or processing of the sample prior to subjecting it to the inventive method. However, in some embodiments, the sample analyzed is an untreated sample such as an untreated whole blood sample. The term "untreated", as used herein, is to be understood that after collecting the sample (e.g., by blood withdrawal from a patient) and before subjecting it to the inventive method no further sample processing (e.g., fractionation methods, drying/reconstitution, and the like) occurs.

A typical nucleic acid detection method involving such untreated samples is described below.

The term "reporter molecule" or "reporter compound", as used herein, denotes any molecule that is capable of forming complexes with one or more target nucleic acids and that can be captured on a binding member, wherein the forming of complexes with the target nucleic acids inhibits the capturing of the reporter compound on the binding member. Thereby, the term "capable of forming complexes", as used herein, refers to any interaction between a reporter molecules and a target nucleic acid. In other words, the term denotes the binding of the molecules to each other that may be accomplished via a common or different binding regions comprised in the reporter molecule that mediate the interaction with the target (such as via Watson-Crick base pairing between complementary nucleotide sequences). Typically, the interaction is reversible. Analogously, the term "being captured on a binding member" also denotes any direct or indirect (for example, via capture molecules; see below) interaction of a reporter molecule with a given binding member. This interaction is generally reversible as well.

In general, the reporter molecules may be nucleic acid molecules (i.e. RNA or DNA molecules as described above) having a length of 10 to 100 nucleotides, for example 15 to 50 nucleotides, 15 to 40 nucleotides or 20 to 30 nucleotides. Usually, the reporter molecules are single-stranded nucleic acid molecules (i.e. oligonucleotides). The reporter compound is configured such that the binding of such a reporter molecule to a target nucleic acid to be detected inhibits the capturing of the reporter molecule on the binding member. The nucleic acid reporter molecules may comprise at least one specific binding region (herein also referred to as "interaction site") that is not only capable of interacting with the target nucleic acid (e.g., by binding to an at least partially complementary sequence region of the target nucleic acid, thus allowing, e.g., Watson-Crick base-pairing between the reporter molecule and the target nucleic acid to be detected), but also of being captured on a binding member. Typically, the specific binding region comprised in the reporter molecule is at least 12 nucleotides in length, e.g. at least 15 nucleotides, at least 18 nucleotides or at least 22 nucleotides. In particular embodiments, the nucleotide sequence of the binding portion of the reporter molecules is complementary to the corresponding nucleotide sequence of the target nucleic acid.

One or more species of reporter molecules may be employed. The term "one or more species" denotes one or more different types of reporter molecules such as one or more nucleic acid molecules having different nucleotide sequences.

The term "binding member" or "support member", as used herein, refers to any solid matrix, on which the reporter molecules can be captured either directly (e.g., via an anchor group comprised in the reporter molecule) or in an indirect manner via one or more species of capture molecules capable of capturing a reporter molecule to the binding member by covalent or non-covalent interactions. Examples of binding members that can be used comprise inter alia the substrates of array elements (e.g., microscope slides, wafers or ceramic materials) or synthetic particles such as magnetic beads (e.g. paramagnetic polystyrol beads, also known as Dynabeads®) and latex beads.

The term "capture molecule", as used in this embodiment, denotes any molecule being comprised on (e.g., that attached to or immobilized on) the binding member that shows a specific binding behavior and/or a characteristic reactivity, which makes it suitable for the formation of complexes with a reporter molecule (i.e. the binding to the reporter molecule). Capture molecules as used in this embodiment may also be denoted as reporter specific capture molecules. Nucleic acids are typically used as capture molecules. Examples of nucleic acids that can be used as capture molecules have been described above in connection with target and reporter molecules, respectively. Such nucleic acids can be of any length and can be either single-stranded or double-stranded molecules. Typically, nucleic acid capture molecules are single-stranded oligonucleotides having a length of 10 to 200 nucleotides, e.g. of 15 to 100 nucleotides or 20 to 70 nucleotides.

The capture molecules may comprise at least one specific sequence region (i.e. the binding region), which is configured to bind a reporter molecule, for example, to interact with a complementary sequence region of a reporter molecule via base-pairing between the capture molecules and the nucleic acid to be detected. Typically, the specific binding region is at least 15 nucleotides in length, e.g. at least 20 nucleotides, at least 40 nucleotides or at least 50 nucleotides. In particular embodiments, the nucleotide sequence of the binding region of the capture molecules is complementary to the corresponding nucleotide sequence of the reporter molecule.

In some embodiments, at least a part of an interaction site of the reporter compound being capable of forming a complex with a target nucleic acid is also capable of forming a complex with a capture molecule. In other words, the capture molecules and the target nucleic acids compete for forming a complex with the reporter compound, that is, the respective binding regions comprised in the capture molecules and the target nucleic acids recognize the same or at least similar corresponding sequence(s) of a reporter molecule. The term "similar sequences", as used herein, denotes sequences that differ only in one or more single nucleotide mismatches (i.e. non-complementary pairs of nucleotides) or by one or more single nucleotide additions, insertions or deletions (i.e. additional or lacking nucleotide residues). Thus, the respective binding regions comprised in the capture molecules and the target nucleic acids are at least partially identical. The term "partially identical", as used herein, denotes sequences differing only in one or more single nucleotides, as described above, or sequences having overlapping binding sites, i.e. sequences sharing a common nucleotide sequence but differ in at least one other part of the sequence region. However, it is also possible that the respective binding regions comprised in the capture molecules and the target nucleic acids recognize different, non-overlapping (e.g., adjacent) sequences of a reporter molecule but binding of either the capture molecule or the target nucleic acid to the reporter molecule sterically interferes with the binding of the other one.

In some embodiments, the chemical equilibrium between the steps of forming of complexes of reporter compound and target nucleic acid on the one hand and capturing of reporter compound on the second binding member (e.g. by forming complexes with a reporter specific capture molecule) on the other hand may be influenced by varying the degree of similarity and/or partial identity of the sequences of the reporter specific capture molecule (with respect to the reporter compound sequences) and the reporter compound (with respect to the target nucleic acid, respectively, as described above.

For instance, the reporter specific capture molecule sequences may be selected such that the binding region with respect to the reporter compound sequence is shorter or longer than that of the binding region of the reporter compound sequence with respect to the target nucleic acid sequence. In this way, the binding affinity of the reporter compound with respect to the target nucleic acid compared to that of the reporter compound with respect to the reporter specific capture molecule may be increased or decreased.

One or more species of capture molecules may be employed. The term "one or more species" denotes one or more different types of capture molecules such as one or more nucleic acid molecules having different nucleotide sequences. More than one species of capture molecule concomitantly used are also referred to as "library". Such libraries comprise at least two but may also comprise many more different molecules, e.g. at least 5 different species, at least 10 different species, at least 30 different species and so forth. The libraries may also be arranged on different locations with respect to the binding member. For example, they may be present in form of arrays or any other spatial arrangement.

The term "array" (also referred to as "microarray"), as used herein, refers to a defined spatial arrangement (layout) of capture molecules on a binding member (also referred to as "substrate"), wherein the position of each molecule within the array is determined separately. Typically, the microarray comprises defined sites or predetermined regions, i.e. so-called "array elements" or "spots", which may be arranged in a particular pattern, wherein each array element typically comprises only one species of capture molecules. The arrangement of the capture molecules on the support can be generated by means of covalent or non-covalent interactions. However, the capture molecules may also be directly immobilized within the reaction chamber of a device used for performing the method (see below).

In a first step, the method may comprise forming a composition of matter including an amount of a reporter compound, a binding member, and an amount of a target nucleotide. The term "forming a composition", as used herein, denotes any combining or mixing of the components described above. This may be achieved by introducing the components either simultaneously, consecutively or separately into one or more reaction chambers of an analytical device suitable for performing the method. Alternatively, it is also possible to mix the individual components before introducing the mixture into the device.

As already described above, the method may also be performed with more than one reporter compound and more than one target nucleotide. Thus, in some embodiments, the step of forming a composition of matter comprises forming a composition of matter comprising:

an amount of a first reporter compound,
an amount of a first target nucleic acid capable of forming complexes with the first reporter compound, the forming of complexes with the first reporter compound inhibiting capturing of the first reporter compound by the binding member,
an amount of a second reporter compound, and
an amount of a second target nucleic acid capable of forming complexes with the second reporter compound, the forming of complexes with the second reporter compound inhibiting capturing of the second reporter compound by the binding member.

The term "device", as used herein, denotes any instrumentation suitable for assaying samples by means of the method. Typical devices for use in the method are described herein. Exemplary embodiments of such a device are illustrated in FIGS. 17 to 19. Further devices suitable for performing the method are described in the European patent application EP 06 122 695 and the international patent application WO 2007/051861, the relevant contents both of which are hereby explicitly referred to as well.

Typically, the devices may comprise at least one structure for accommodating liquid samples (herein also referred to as "reaction chamber" or "reaction space"). The term "reaction chamber", as used herein, denotes the space formed within the device between a base surface and a top surface (also referred to as first and second surfaces), in which at least one step of the actual analysis, e.g., the detection of the target nucleic acids, is performed. The base and top surfaces may be located opposite or substantially opposite to each other. For example, they may be arranged in parallel or substantially parallel to each other.

In some embodiments, the reaction chamber may comprise two or more sub-chambers. This can be achieved by providing the first surface and/or the second surface with one or more partitions or cavities, which serve as lateral sidewalls between the two or more sub-chambers.

In a further embodiment, a device used in the method comprises more than one reaction chamber in order to perform multiple assays of one sample in parallel or to perform different steps of an assay in a serial manner in different reaction chambers. To this end, the reaction chambers may be in fluid communication with each other. The term "in fluid communication with each other", as used herein, denotes any interconnection between the individual reaction chambers, either directly or indirectly via an additional means such as a common sample introduction passage, filling unit, processing unit or the like. However, as used herein, the term does not necessarily mean that, after introducing a sample, the reaction chambers are in permanent fluid communication with each other. It is also possible that the reaction chambers are in transient fluid communication, for example achieved by unidirectional or bidirectional valves at the connections between the reaction chambers.

The reporter molecules and/or the capture molecules may be provided (e.g. in lyophilized or dried form) in one or more of the at least one reaction chamber (or in one or more sub-chambers) of the device, in which the detection assay is performed, prior to the introduction of the sample (comprising the target nucleic acids) to be analyzed. The reporter molecules and/or the capture molecules may be provided in the same reaction chambers (or sub-chambers) or in different ones. Alternatively, the reporter molecules and/or the capture molecules may be introduced into the device along with the sample (i.e. concomitantly) or after the sample has already been introduced.

Analogously, the binding member may be provided in one or more of the at least one reaction chamber (or in one or more sub-chambers) of the device, in which the detection assay is performed, prior to the introduction of the sample (comprising the target nucleic acids) to be analyzed. The binding member may be provided in the same reaction chambers (or sub-chambers) as the reporter molecules and/or the capture molecules or in different ones. For example, it may be possible to perform the step of forming complexes of reporter molecules with the target nucleic acids spatially separated from the step of capturing the reporter molecules to the binding member, i.e. in different reaction chambers (or sub-chamber) of the device. In such embodiments, the individual components are usually not provided in the same reaction chambers. Instead of providing the binding member in the device prior to adding the sample, it may be introduced into the device along with the sample (i.e. concomitantly) or after the sample has already been introduced.

In specific embodiments, the device used in the method is a device selected from the group consisting of a bio sensor assay device, a micro-fluidic cartridge, and a lab-on-chip.

After forming the composition of matter, the method may comprise the step of forming complexes of a subset of the amount of reporter compound with at least a subset of the amount of target nucleic acid. In other words, the reporter molecules may be allowed to bind to the target nucleic acids, for example by forming double-stranded nucleic acid molecules via base pairing of complementary nucleotide sequences of the reporter compound and the target nucleic acid, respectively. The fact that a subset of the amount of reporter compound forms complexes with at least a subset of the amount of target nucleic acid present denotes that the total concentration of reporter molecules present at the beginning of the assay may exceed the total concentration of target nucleic acids present.

Subsequently, the remaining amount of reporter compound that is not in complex with a target nucleic acid may be captured (i.e. bound) on the binding member via the one or more binding regions comprised in the reporter molecule described above (either directly or by binding to capture molecules being attached to the binding member). Since the forming of complexes of the target nucleic acids with the reporter molecules inhibits the capturing of the reporter molecule on the binding member, the forming of target nucleic acid/reporter molecule complexes decreases the amount of reporter molecules that can be captured on the binding member as compared to the amount being present prior to performing the step of forming target nucleic acid/reporter molecule complexes.

In specific embodiments of the inventive method, the step of forming complexes of a subset of the amount of reporter compound with at least a subset of the amount of target nucleic acid and the step of capturing a remaining subset of the amount of reporter compound not in complex with a target nucleic acid on the binding member are performed concomitantly.

Finally, the method may comprise determining a value indicative for the presence and/or amount of reporter compound captured on the binding member. The term "determining a value indicative for the presence and/or amount of reporter compound captured on the binding member", as used herein, refers to the detection/determination of parameters such as electrical conductivity, redox potential, optical absorption, fluorescence intensity or bioluminescence that allow for qualitative and/or quantitative measurements of the reporter molecules captured (or re-captured) on the binding member. Only one of these parameters may be determined but it is also possible to determine more than one parameter (e.g., electrical conductivity and the intensity of a fluorescence signal caused by a suitable label), either concomitantly or consecutively.

In some embodiments, the method further comprises determining a value indicative for the presence and/or amount of target nucleic acid based on the value indicative for the presence and/or amount of reporter compound captured on the binding member. That is, the presence and/or amount of the one or more target nucleic acids present in a particular sample may be calculated based on the difference between the presence and/or amount of reporter compound being present prior to the forming of target nucleic acid/reporter molecule complexes and the amount of reporter compound being captured on the binding member after said complex formation.

For performing the detection reaction, the reporter compound may comprise one or more detectable labels as described above, e.g. fluorescent labels. For instance, the reporter compound may comprise two detectable labels. The detectable labels may be incorporated or attached to the reporter molecules, e.g., in form of modified and/or labelled ribonucleotides, deoxynucleotides or dideoxynucleotides.

For detecting such labels, the device used for performing the method may further comprise a detection system as described above suitable for determining values indicative for the presence and/or amount of reporter compound captured on a binding member, e.g. an optical detection system. The detection system may be connected to the reaction chamber. Typically, the detection system is positioned opposite to one of the at least one reaction chamber, optionally opposite to a particular surface region where detection takes place.

In some embodiments, the method further comprises releasing the remaining subset of the amount of reporter compound from the binding member after the steps of forming complexes of a subset of the amount of reporter compound with at least a subset of the amount of target nucleic acid, capturing a remaining subset of the amount of reporter compound not in complex with a target nucleic acid on the binding member, and determining the value indicative for the presence and/or amount of reporter compound captured on the binding member. The term "releasing", as used herein, denotes the detachment or unbinding of the reporter molecules from the binding member. This may be accomplished, for example, enzymatically via the cleavage any covalent bonds or in cases, where the nucleic acid reporter molecules are bound to the binding member by nucleic acid capture molecules via complementary base-pairing, by increasing the temperature in the reaction chamber, in which the assay is performed, thus resulting in nucleic acid strand separation (i.e. denaturation).

In further embodiments, the steps of releasing, forming complexes, capturing, and determining are repeated N additional times, where N is an integer greater than or equal to 1. In other words, the method is performed in a cyclic manner. In specific embodiments, the integer N is ≥5, ≥10 or ≥20.

In some embodiments, prior to the step of forming complexes, the method further comprises capturing at least a subset of the amount of reporter compound on the binding member; determining a value indicative for the presence and/or amount of reporter compound captured on the binding member; and releasing captured reporter compounds from the binding member. Thus, performing these additional steps enables the determination of the amount of reporter compound initially present before allowing the formation of complexes between receptor compound and target nucleic acid. Comparing the value obtained with that determined after capturing the subset of reporter compound not in complex with a target nucleic acid on the binding member provides a measure for the presence and/or amount of target nucleic acid present in a sample.

In particular embodiments, the method further comprises subjecting the target nucleic acid to amplification, that is, to increase their amount present in the sample before subjecting the same to the further analysis in order to facilitate further detection. Typically, target nucleic acid amplification is achieved by means of a cyclic amplification. The cyclic amplification may comprise any number of amplification cycles that is equal or greater than two. Usually, cyclic amplification reaction comprises at least 10 or at least 20 cycles.

An exemplary cyclic amplification is a polymerase chain reaction (PCR) as described above. Typically, PCR is used for the amplification of double-stranded DNA molecules by employing a thermostable DNA polymerase. In some embodiments, the DNA polymerase used in the cyclic amplification has exonuclease activity, particularly 5'→3' exonuclease activity. Examples of such DNA polymerases include inter alia Taq DNA polymerase or Tth DNA polymerase (which are commercially available from multiple providers). By means of this 5'→3' exonuclease activity the DNA polymerase may nucleolytically attack the labelled 5'-termini of reporter molecules that are bound to the target nucleic acids resulting in a progressive degradation of such reporter molecules. As a result, the amount of reporter compound that is captured on the binding member additionally decreases during each cycle of the amplification reaction. Optionally, the DNA polymerase employed may also exhibit 3'→5' exonuclease activity ("proofreading activity") for removing an incorrect nucleotide that has been added to the nascent DNA strand at a particular sequence position. Examples of such DNA polymerases having both exonuclease activities include inter alia Pwo DNA polymerase, and Pfu DNA polymerase (both enzymes are also commercially available from various suppliers).

If the target nucleic acid is a RNA molecule, the method may further comprise subjecting the target nucleic acid to reverse transcription as described above prior to subjecting them to amplification.

Amplification of the target nucleic acid may be initiated prior to the step of forming complexes of a subset of the amount of reporter compound with at least a subset of the amount of target nucleic acid. That is, the target nucleic acid is subjected to amplification while allowing reporter compounds to form a complex with a target nucleic acid, and reporter compounds not in complex with a target nucleic acid to be re-captured on the binding member For this purpose, i.e. nucleic acid amplification, the device used in the method may further comprise one or more temperature control units and/or temperature regulating units as described above for controlling and/or regulating the temperature within the reaction chamber.

Measuring the temperature in the reaction chamber can be performed as described above. Usually, amplification such as a PCR comprises three basic steps—denaturation, annealing of the primers, and extension of the primers—that are iteratively performed in a cyclic manner. However, the amplification may further comprise an initial denaturation step prior to the first "true" amplification cycle and/or a final extension step after completion of the final amplification cycle, respectively. In some embodiments of the inventive method, target nucleic acid amplification comprises (at least) a step of denaturing double-stranded nucleic acids and/or a combined step of annealing and extending the primer molecules at the target nucleic acids (i.e. a "two-step PCR").

The denaturation step involves the heating of the sample to be analyzed to a temperature of 94-95° C., typically for 0.5 s to 5 min, thus resulting in the strand-dissociation of double-stranded nucleic acid templates. Subjecting a sample to be analyzed to such denaturation step may further result in (i.e. allow) the simultaneous denaturation of the double stranded nucleic acids in the sample including double-stranded target molecules, double-stranded reporter molecules, complexes of reporter compounds with target nucleic acids, and complexes of reporter compounds with capture molecules (attached to the binding member), the latter resulting in the release of the reporter compounds from the binding member.

The annealing step involves the cooling down of the sample to be analyzed to a temperature of 40-65° C., typically for 1 s to 5 min, to allow the association (i.e. the hybridization/base-pairing) of the primer molecules to the denaturated nucleic acid template strands. The reaction temperature employed depends on the chemical and/or physical properties of the primer molecules to be annealed such as their nucleotide sequence composition, melting temperature, their tendency for intra-molecular folding (e.g., the formation of double-stranded hairpin or turn structures), and the like. Subjecting a sample to be analyzed to such annealing step may further result in (i.e. allow) the re-association of double-stranded target molecules, the re-association of double-stranded reporter molecules, the forming of complexes of reporter compounds with nucleic acid targets, and the forming of complexes of reporter compounds not in complex with a target nucleic acid with capture molecules, the latter resulting in the capturing or re-capturing of the reporter compounds on the binding member. Thus, in some embodiments, the annealing step is performed concomitantly with the step of forming complexes of a subset of the amount of reporter compound with at least a subset of the amount of target nucleic acid and/or the step of capturing a remaining subset of the amount of reporter compound not in complex with a target nucleic acid on the binding member.

Finally, the extension step involves the extension of the hybridized primer molecules to produce full-length copies of the DNA template strands by a DNA polymerase. The length of the amplified DNA fragment is determined by the 5' ends of the pair of primers employed. Typically, the elongation step is performed at a temperature of 70-72° C. for 1 s to 10 min. Subjecting a sample to be analyzed to such extension step may further result in the replication of the target nucleic acids to be analyzed by allowing the complexes of a subset of the amount of reporter compound with at least a subset of the amount of target nucleic that have been formed during the annealing step to be extended to generate double-stranded amplified nucleic acid fragments having incorporated an optionally labelled reporter compound that subsequently may be detected.

The detection/determination of a value indicative for the presence and/or amount of the target nucleic acids may be performed only once or more than once during the assay performed. In case, more than one detection step during a single assay is performed, the mean value of the results obtained is calculated. The data obtained in one or more cycles of detection may be analyzed and mathematically processed using appropriate computer software known by persons skilled in the art in order to determine inter alia the presence, the length or the sequence of one or more target nucleic acids and/or to calculate its/their amount.

In some embodiments, particularly if the reporter compound is in excess of the target nucleic acid, the value indicative for the presence and/or amount of reporter compound captured on the binding member is determined before the forming of complexes of a subset of the amount of reporter compound with at least a subset of the amount of target nucleic acid and the capturing of a remaining subset of the amount of reporter compound not in complex with a target nucleic acid on the binding member are in chemical equilibrium. For example, the determination/detection step is performed during the annealing step of an amplification reaction. However, it is also possible to perform the determination/detection reaction after completion of the annealing step (i.e. during or after completion of the elongation step).

In a further embodiment, the value indicative for the presence and/or amount of reporter compound captured on the binding member is determined 1 s to 120 s (e.g., 1, 5, 10, 15, 20, 30, 60 or 120 s) after initiating the steps of forming complexes of a subset of the amount of reporter compound with at least a subset of the amount of target nucleic acid and of capturing a remaining subset of the amount of reporter compound not in complex with a target nucleic acid on the binding member.

In other embodiments, the value indicative for the presence and/or amount of reporter compound captured on the binding member is determined after at least one cycle of the cyclic amplification comprising denaturation, annealing, and elongation steps, e.g., during or after completion of the annealing step. In specific embodiments, said value is determined after each cycle of the cyclic amplification. In other specific embodiments, the value indicative for the presence and/or amount of target nucleic acid is determined each time after determining the value indicative for the presence and/or amount of reporter compound captured on the binding member.

In some embodiments, determining the value indicative for the presence and/or amount of reporter compound captured on the binding member comprises time-dependent monitoring of the indicative value (i.e. the repeated performing of the determination/detection step and monitoring the course of the indicative value over time).

In further embodiments, the value indicative for the presence and/or amount of target nucleic acid is determined based on a calibration curve correlating the value indicative for the presence and/or amount of reporter compound with the value indicative for the presence and/or amount of target nucleic acid.

The method may further comprise adding an amount of a quencher compound capable of forming complexes with the reporter compound not in complex with target molecules or reporter specific capture molecules. The quencher compound may comprise one or more moieties interfering with the generation of a detectable signal by a label (e.g., a quencher group "hijacking" the emissions that resulted from excitation of a fluorophor). E.g. the quencher groups may be capable of suppressing or inhibiting signals emitted by a detectable label of the reporter compound, e.g. a fluorescence signal. In such an embodiment, the quencher compound may be capable of forming complexes with the reporter compound not in complex with target molecules or reporter specific capture molecules such that the one or more quencher groups are in close proximity to the detectable label of the reporter compound within the complex.

The quencher compound may be an oligonucleotide. In this embodiment, the quencher oligonucleotide may comprise at least one specific sequence region which is complementary to a sequence region of a reporter oligonucleotide, thus allowing base-pairing between the quencher compound and the reporter compound.

The quencher group may include usual quencher groups such as for instance Black Hole Quenchers (Biosearch Technologies), Qxl quenchers (AnaSpec) and Iowa black quenchers.

The quencher compounds may be provided in the second structure of a device as described above. In such an embodiment, the quencher compound may form a complex with a reporter compound not captured on the second binding member.

The second structure of a device as described above may be irreversibly sealed before initiating amplification of the target nucleic acids. Irreversibly sealing the second structure may be achieved by sealing (e.g. welding) an inlet and, optionally an outlet of the second structure, e.g. by heat-sealing channels and/or valves connected with the second structure.

According to another exemplary embodiment, a method is provided, the method comprising:
introducing a fluid whole blood sample into a device adapted for accommodating a sample in a fluid state; and
determining a value indicative of the presence and/or amount of nucleic acids associated with viral infections in the whole blood sample based on an analysis performed in the device.

Particularly, the value determined is indicative of the presence and/or amount of total nucleic acids associated with a viral infection.

According to another exemplary embodiment, a method is provided, the method comprising:
providing a fluid sample having a volume of 1 µl to 50 µl; and
determining a value indicative of the presence and/or amount of nucleic acids associated with viral infections in the sample based on an analysis performed in the device.

Optionally, the method may further comprise introducing the fluid sample into a device adapted for accommodating a sample in a fluid state; and determining a value indicative of the presence and/or amount of nucleic acids associated with viral infections in the whole blood sample based on an analysis performed in the device.

Particularly, the value determined is indicative of the presence and/or amount of total nucleic acids associated with a viral infection.

The term "fluid sample" or "liquid sample", as used herein, denotes a liquid which is to be analyzed by the method, and which is supposed to comprise one or more nucleic acids to be detected (i.e. nucleic acids associated with a viral infection). Typically, the fluid sample to be analyzed is a biological sample. Examples of fluid samples that can be analyzed include inter alia human and non-human body fluids such as whole blood, blood plasma, blood serum, urine, sputum, salvia or cerebrospinal fluid, cellular extracts, tissue cultures, and the like. In some embodiments, the fluid samples to be analyzed are blood samples (i.e., for example, whole blood, blood plasma, and blood serum), particularly whole blood samples.

The volume of the fluid sample to be analyzed may be in the range of 1 µl to 50 µl, typically in the range of 1 µl to 45 µl or 1 µl to 40 µl or 1 µl to 30 µl or 1 µl to 25 µl or 1 µl to 20 µl or 1 µl to 15 µl. In particular embodiments, the volume of the fluid sample is in the range of 1 µl to 10 µl. However, in case whole blood samples are analyzed sample volumes exceeding 50 µl are within the scope of the invention as well.

The term "whole blood", as used herein, refers to blood with all its constituents. In other words, whole blood comprises both blood cells such as erythrocytes, leukocytes, and thrombocytes, and blood plasma in which the blood cells are suspended.

The term "blood plasma" (or "plasma"), as used herein, denotes the blood's liquid medium and is an substantially aqueous solution containing water, blood plasma proteins, and trace amounts of other materials such as serum albumin, blood clotting factors, immunoglobulins (antibodies), hormones, carbon dioxide, various other proteins and various electrolytes (mainly sodium and chloride).

The term "blood serum" (or "serum"), as used herein, refers to plasma from which the clotting proteins have been removed.

In further embodiments, the fluid sample introduced into the device is an untreated whole blood sample. The term "untreated", as used herein, is to be understood that after collecting the sample (e.g., by blood withdrawal from a patient) and before subjecting it to the inventive method no further sample processing (e.g., fractionation methods, drying the whole blood, e.g. on filter paper, for sample storage, and reconstitution of dried blood samples by re-dissolving in water, and the like) occurs.

However, the storage of the samples per se, for example in a refrigerator or freezer, is not to be considered a processing step as defined above. Thus, the sample may be introduced into the device immediately after collection or it may be introduced into the device after storage of the sample for one or more hours to one or more days or weeks.

In addition, since whole blood samples comprise blood-clotting factors, which will cause the formation of blood clots upon prolonged storage of the samples and whose presence may thus interfere with the subsequent analysis, the addition of anti-coagulants (i.e. inhibitors of blood clotting) is also not a treatment of the sample within the meaning of the present invention. Multiple compounds acting as anti-coagulants are well known in the art. Examples of anti-coagulants include inter alia natural or synthetic (i.e. obtained by chemical synthesis and/or recombinant DNA technology) vitamin K antagonists, natural or synthetic direct thrombin inhibitors, citrate, oxalate, heparin and ethylene-diamine-tetraacetic acid (EDTA).

In other embodiments, the fluid whole blood sample is introduced into the device directly (i.e. in untreated form, as defined above) from a patient. Particularly, the fluid whole blood sample may be obtained from a puncture at a fingertip of the patient. For example, after puncturing the fingertip the leaking blood may be collected by contacting the blood with a capillary such that the blood is introduced by capillary force without external manipulation. The capillary may then be positioned relative to the assay device employed such that the blood can pass or can be actively transferred into the device. Alternatively, the punctured fingertip may be positioned immediately adjacent to one of the openings of the device, which are detailed below (e.g. by pressing the finger tip directly on such an opening) such that the blood leaking from the puncture may be introduced into the device.

The term "nucleic acids associated with viral infections", as used herein, denotes any nucleic acid molecule of viral origin (i.e. whose nucleotide sequence is identical or complementary to a corresponding sequence within the virus genome) that is present in a fluid sample to be analyzed that has been infected by one or more virus species. The viruses infecting the host, from which the fluid sample is obtained, may be any DNA virus (i.e. a virus having a DNA genome) or RNA virus (i.e. a virus having a RNA genome) (reviewed, e.g., in: Büchen-Osmond, C. (2003). *Taxonomy and Classification of Viruses*. In: Manual of Clinical Microbiology, 8th ed., vol. 2, p. 1217-1226, ASM Press, Washington D.C.). Examples of DNA viruses include inter alia the families of Papovaviridae (e.g. papillomavirus), Adenoviridae (e.g. adenovirus), and Herpesviridae (e.g. Epstein-Barr virus, cytomegalovirus). Examples of RNA viruses include inter alia the families of Picornaviridae (e.g. poliovirus, rhinovirus) Flaviviridae (e.g. hepatitis C virus), Filoviridae (e.g. Marburg virus, ebolavirus), and Retroviridae (e.g. human immunodeficiency virus (HIV)). In some embodiments, the nucleic acids to be detected are associated with infections caused by members of the Retroviridae, particularly they are associated with HIV infections. The term "HIV", as used herein, refers to both the HIV-1 and HIV-2 species and to any subtypes derived thereof.

Since many DNA viruses as well as the Retroviridae (notably, the replication of the Retroviridae generally requires reverse transcription of the RNA virus genome into DNA), can integrate their genetic information into the host cell's genome in form of a latent pro-virus, the term "nucleic acids associated with viral infections" does not only refer to nucleic acids originating from free and from cell-associated viruses but also to pro-viral DNA molecules being integrated into the host's genome, reverse transcribed viral DNA molecules (i.e. the "intermediates" of viral replication), and transcripts derived from pro-viral DNA (i.e. RNA molecules obtained by transcription of the host DNA genome).

In particular embodiments, the methods are intended to determine the amount of total viral nucleic acids in a fluid sample to be analyzed. In other words, the method may aim at the detection of all different species (i.e. both RNA and DNA molecules) and cellular subsets (i.e. spatially separated nucleic acid pools) of nucleic acids associated with a viral infection of a patient. Typically, the nucleic acids to be detected are associated with a single type of viral infection such as a HIV infection. However, it may also be possible that a patient suffers from a co-infection with different types of viruses. The method may further comprise determining the presence and/or the (total) amount of the nucleic acids associated with the respective different types of viruses either concomitantly in a single analysis or in a plurality of separate analysis (which may, however, be performed using the same fluid sample).

Thus, in case a patient has been infected with HIV, then the nucleic acids associated with the HIV infection that may be present in a whole blood sample obtained from that patient comprise RNA molecules originating from free HIV (i.e. virus particles freely circulating in the plasma), RNA molecules originating from cell-associated HIV (i.e. virus particles attached to any type of blood cells), pro-viral HIV DNA molecules being integrated into the host's genome, reverse transcribed HIV DNA molecules, and HIV transcripts derived from pro-viral DNA. However, a blood plasma sample obtained from the same patient only comprises RNA molecules originating from free HIV, since all other HIV nucleic acid species are associated with the patient's blood cells that have been removed.

The term "device", as used herein, denotes any instrumentation suitable for assaying samples by means of the methods described above provided that the device is "adapted for accommodating the samples in a fluid state", which means that the device is configured such that the fluid (i.e. liquid) state of the sample is maintained while the sample is accommodated in the device. That is, the sample is not in any way dried in the device before nucleic acid analysis takes place, such as by applying the sample on filter paper and allowing excess liquid to evaporate. Herein, such a device is also referred to as a "microfluidic device".

Typical devices for use in the method are described herein. Exemplary embodiments of such a device are illustrated in FIGS. 17 to 19. Further devices suitable for performing the method are described in the European patent application EP 06 122 695 and the international patent application WO 2007/051861, the relevant contents both of which are hereby explicitly referred to as well.

The devices used for performing the methods comprise at least one structure for accommodating liquid samples (herein also referred to as "reaction chamber" or "reaction space"). The term "reaction chamber", as used herein, denotes the space formed within the device between a base surface and a top surface (also referred to as first and second surfaces), in which at least one step of the actual analysis, e.g., the detection of the target nucleic acids, is performed. The base and top surfaces may be located opposite or substantially opposite to each other. For example, they may be arranged in parallel or substantially parallel to each other.

In some embodiments, at least a part of the at least one reaction chamber is made of a transparent material, that is, a light-permeable material, to facilitate nucleic acid detection. Examples of suitable transparent materials include inter alia glasses or glass-like materials (e.g., acrylic glass) as well as synthetic polymers (e.g., polymethylmethacrylate, acryl or polyethylene).

In other embodiments, at least a part of the at least one reaction chamber is flexible or elastically deformable. That is, at least one or more parts of the reaction chamber are made of an elastically deformable material, for example an elastic membrane (e.g., silicone rubber).

In some devices used, the at least one reaction chamber may comprise two or more sub-chambers. This can be achieved by providing the first surface and/or the second surface with one or more partitions or cavities, which serve as lateral sidewalls between the two or more sub-chambers.

In some embodiments, a device comprises more than one reaction chamber in order to perform multiple assays of one sample in parallel or to perform different steps of an assay in a serial manner in different reaction chambers (see also FIG. 17). To this end, the reaction chambers may be in fluid communication with each other. The term "in fluid communication with each other", as used herein, denotes any interconnection between the individual reaction chambers, either directly or indirectly via an additional means such as a common sample introduction passage, filling unit, processing unit or the like (also referred to as a "microfluidic network"). However, as used herein, the term does not necessarily mean that, after introducing a sample, the reaction chambers are in permanent fluid communication with each other. It is also possible that the reaction chambers are in transient fluid communication, for example achieved by unidirectional or bidirectional valves at the connections between the reaction chambers.

In the assay devices used in the method the distance between the base surface and the top surface of at least one of the at least one reaction chamber may be variable via one or more actuators (also referred to as displacers). An actuator denotes a means for allowing the vertical movement of the base surface and/or the top surface, or at least one or more parts thereof, relative to each other. Thus, the variation of the distance between said surfaces may not necessarily occur over the entire surface area but may also be locally restricted to at least one part of the surface area of either one or both of said surfaces. Typically, the distance between the base surface and/or the top surface is reduced, for example by applying pressure via the actuator(s) to at least a part of either one or both of said surfaces. An actuator may constitute an integral part of the base surface or the top surface (e.g., configured as a bulge or buckle) or may represent an independent, i.e. self-contained, entity (such as a tappet or a stencil) located outside the reaction chamber.

The variation of the distance between the top surface and the base surface via the one or more actuators may result in the displacement of at least a part of the sample within a particular reaction chamber and/or in the movement (transport) of at least a part of the sample between different reaction chambers (or sub-chambers) in which different method steps may take place. That is, by operating the actuator(s) the sample is moved within or between the at least one reaction chamber of the device. The repetitive and alternating reduction and re-increasing of the distance between said surfaces will thus also result in a corresponding forward and backward movement of the sample within the reaction chamber (i.e. the mixing of a sample).

Instead of varying the distance between the base surface and the top surface of a reaction chamber via one or more actuators transport or movement of a fluid sample in the device may inter alia be accomplished by means of a pump, in particular by employing a vacuum pump or a peristaltic pump.

A reaction chamber of a device used herein may further comprise one or more microarrays (herein also referred to as "arrays" or "array elements") being disposed on the base surface and/or the top surface of the at least one reaction chamber. As used herein, a "microarray" denotes a defined spatial arrangement (layout) of capture molecules (e.g., one or more species of probe molecules or a substance library; cf. also below) on a support member (also referred to as "substrate" or "binding member"), wherein the position of each molecule within the microarray is determined separately. Typically, the microarray comprises defined sites or predetermined regions, i.e. so-called array elements or spots, which may be arranged in a particular pattern, wherein each array element typically comprises only one species of capture molecules. The arrangement of the capture molecules on the support can be generated by means of covalent or non-covalent interactions. Suitable substrates for microarrays include inter alia microscope slides, wafers or ceramic materials. However, the capture molecules may also be directly immobilized on the base surface and/or the top surface.

A reaction chamber of a device used in the method may further comprise one or more openings, which may be lockable and/or sealable, and which may be used for the direct introduction of a sample to be analyzed as well as any additional reagents, detection agents or the like that may optionally also be required for performing the method. Alternatively, such openings may also be used for the attachment of any additional (supplementary) modules of the device that have not been designed as integral parts of the device, such as inter alia filling units, processing units, temperature control units, specific detection units, and waste containers.

In specific embodiments, the device is a device selected from the group consisting of a biosensor assay device, a micro-fluidic cartridge, and a lab-on-chip.

In some embodiments, the device is adapted for detecting nucleic acids in a fluid (i.e. liquid) sample. In other words, the device further comprises a detection system as described above, e.g. an optical detection system, that may be connected to the reaction chamber. Typically, the detection system is positioned opposite to one of the at least one reaction chamber, optionally opposite to a particular surface region where detection takes place. The selection of a suitable detection system depends on several parameters such as the type of labels used for detection or the kind of analysis performed. In some embodiments, performing the method involves simple detection systems, which may be based on the measurement of parameters such as fluorescence, optical absorption, resonance transfer, and the like.

Typically, the devices and systems are self-contained. That is, they do not necessarily require removal and/or replacement of the sample and/or any other reagents in the reaction chamber while performing an assay. Thus, such devices may only comprise a sample inlet port but no outlet port.

The fluid sample to be analyzed may be introduced directly into the device via one or more openings of the at least one reaction chamber, which may be lockable and/or sealable. The sample may be transferred, optionally along with additional reagents (such as buffers or other diluents, dyes, labels, assay reagents or enzymes for performing the detection analysis), into the reaction chamber by using a suitable pressure-generating means, for example, a pipette, a syringe or an automated unit, which may be, for example, a functional unit of a processing apparatus. Alternatively, the sample may also be introduced into the reaction chamber by capillary force without any external manipulation, for example by placing the sample immediately adjacent to one of the openings being present in any of the surfaces defining the reaction chamber.

The method may be performed without the requirement to remove and/or replace the sample and/or any other reagents in the reaction chamber while performing the method. However, some applications may require the introduction of additional reagents into the reaction chamber such as one or more agents comprising any labels in order to allow further detection of the nucleic acids of interest. Such additional solutions may also be directly introduced into the reaction chamber, as described above, either before introducing the sample or concomitantly with the sample or after the sample has been introduced into the reaction chamber. In some embodiments, the additional reagents are provided within the device before adding the sample, particularly in lyophilized or dry form such as powders, granules or pellets.

Alternatively, introducing the sample to be analyzed, and optionally of further reagents, may also be possible in an indirect manner by means of one or more filling units which may be an integral part of the device or it may be designed as a separate part that can be attached to the reaction chamber for filling the same and detached after use. Any container that is capable of holding a liquid sample to be analyzed and that can be (reversibly) connected to the reaction chamber may be used as filling unit. For example, the filling unit may a capillary suitable for taking of a blood sample.

The device may comprise an integrated or a detachable separate waste container, which serves for taking up surplus media from the reaction chamber. Optionally, the waste container comprises a further gaseous, liquid, or solid filler medium such as inter alia cellulose, filter materials, and silica gels, which binds the surplus substances reversibly or irreversibly. Furthermore, the waste container may comprise one or more air vents or may be provided with a vacuum in its interior for improving the transfer of surplus material to the waste container.

After the sample, and optionally any additional reagents, have been introduced into the reaction chamber or have been transferred from the one or more filling units into the reaction chamber, the sample may optionally be incubated in the reaction chamber for a given period of time to allow proper diffusion throughout the reaction space. Typically, the incubation period is in the range of 1 s to 30 min, e.g. in the range of 10 s to 15 min, or in the range of 30 s to 10 min.

In some embodiments, the analysis performed in the device further comprises releasing the nucleic acids from the fluid sample to be analyzed. To this end, the sample may be heated in order to destroy cellular membranes and/or viral capsids (e.g., by employing a temperature control unit and/or temperature regulating unit as described below). In some embodiments, this releasing step comprises contacting the fluid sample with a lysing reagent as described above.

In further embodiments, the analysis performed in the device further comprises amplifying the nucleic acids associated with viral infections, that is, to increase their amount present in the sample before subjecting the same to the further analysis in order to facilitate further detection. Typically, nucleic acid amplification is achieved by means of a polymerase chain reaction (PCR) as described above.

Inter alia for this purpose, i.e. nucleic acid amplification, the device used in the method may further comprises a temperature control unit and/or temperature regulating unit as described above for controlling and/or regulating the temperature within the reaction chamber.

Measuring the temperature in a reaction chamber can be performed as described above.

In some embodiments, the analysis performed in the device further comprises forming complexes, each complex comprising a nucleic acid associated with a viral infection and a capture molecule, wherein the capture molecule comprises a binding portion specific to a region of the nucleic acid associated with a viral infection and an anchor group.

The term "capture molecule", as used in this embodiment, denotes any molecule that shows a specific binding behavior and/or a characteristic reactivity, which makes it suitable for the formation of complexes with a nucleic acid to be detected. Nucleic acids are typically used as capture molecules. Examples of nucleic acids that can be used as capture molecules include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, nucleic acid capture molecules are single-stranded oligonucleotides having a length of 10 to 150 nucleotides, e.g. of 20 to 100 nucleotides, 25 to 80 nucleotides or 30 to 70 nucleotides. In specific embodiments, the capture molecules are used as primers in a PCR in order to amplify any target nucleic acid of interest being present in a given fluid sample.

In some embodiments, the capture molecules comprise at least one specific sequence region (i.e. the binding portion referred to above), which is complementary to a sequence region of a nucleic acid associated with a viral infection (i.e. the target nucleic acid), thus allowing base-pairing between the capture molecules and the nucleic acid to be detected. Typically, the specific binding region is at least 12 nucleotides in length, e.g. at least 15 nucleotides, at least 18 nucleotides or at least 22 nucleotides. Particularly, the nucleotide sequence of the binding region of the capture molecules is complementary to the corresponding nucleotide sequence of the target nucleic acid. As used herein, the term "nucleotide" is to be understood as referring to both ribonucleotides and deoxy-ribonucleotides (i.e. RNA and DNA molecules).

The capture molecules may be provided (e.g. in lyophilized or dry form) in one or more of the at least one reaction chamber of the device prior to the introduction of the fluid sample to be analyzed. Alternatively, the capture molecules may be introduced into the device along with the sample (i.e. concomitantly) or after the sample has already been introduced.

One or more species of capture molecules may be employed. The term "one or more species" denotes one or more different types of capture molecules such as one or more nucleic acid molecules having different nucleotide sequences. More than one species of capture molecule concomitantly used are also referred to as "library". Such libraries comprise at least two but may also comprise many more different molecules, e.g. at least 5 different species, at least 10 different species, at least 30 different species, and so forth. The libraries may also be present in form of array elements or any other spatial arrangement.

In other embodiments, the analysis performed in the device further comprises contacting the complexes comprising a nucleic acid to be detected and a capture molecule with a first binding member of the device, the first binding member being configured to bind the anchor group of the capture molecule in order to bind the complexes to the first binding member.

The term "first binding member", as used in herein, refers to any solid matrix, to which the capture molecules, and thus also any complexes comprising such capture molecule, can be coupled via the anchor group of the capture molecules by covalent or non-covalent interactions. Examples of such matrices comprise inter alia the substrates of array elements (cf. above) or synthetic particles such as magnetic beads (e.g., paramagnetic polystyrol beads, also known as Dynabeads®) and latex beads. Depending on the type of capture molecule, the type of anchor group, and the intended application, in each case a large variety of linkages are possible. For example, the anchor group of the capture molecules may be a biotin moiety, which may be coupled to an avidin or a streptavidin group being attached to the binding member. Alternatively, the capture molecules may comprise a stretch of adenosine residues (e.g. 10 adenosine residue) that will interact with a corresponding stretch of thymidine residues bound to the binding member. Specific coupling reagents are commercially available from different providers and well established in the art (see, for example, Sambrook, J. et al., supra; Ausubel, F. M. et al., supra, and Lottspeich, F., and Zorbas H., supra).

The first binding member may be provided in one or more of the at least one reaction chamber of the device prior to the introduction of the fluid sample to be analyzed. Thereby, the binding member may be provided in the same one or more reaction chambers as the capture molecules or in at least one different reaction chamber. Typically, the step of forming complexes of capture molecules with nucleic acids associated with a viral infection is performed spatially separated from the step of contacting the complexes with the first binding member, i.e. in different reaction chambers of the device (e.g. the "lysis well" and the "central well" referred to in FIG. 17). In such embodiments, the capture molecules and the first binding member are usually provided in different reaction chambers. Instead of providing the first binding member in the device prior to adding the sample, the first binding member may be introduced into the device along with the sample (i.e. concomitantly) or after the sample has already been introduced.

In specific embodiments, the method further comprises capturing the target nucleic acids that have been amplified, typically by subjecting the sample to be analyzed to PCR, with respect to the first binding member (i.e. immobilizing the target nucleic acids thereon).

In other specific embodiments, the analysis performed in the device further comprises providing reporter molecules comprising an interaction site capable of forming a complex with a nucleic acid associated with a viral infection and capable of being captured on a second binding member of the device.

The term "reporter molecule" or "reporter compound", as used herein, denotes any molecule that is capable of interacting with both a target nucleic acid to be detected and a second binding member. Thereby, the interaction occurs via a common or different binding regions comprised in the reporter molecule. In general, the reporter molecules are nucleic acid molecules (i.e. RNA or DNA molecules as described above) having a length of 10 to 100 nucleotides, for example 15 to 50 nucleotides, or 20 to 30 nucleotides. Usually, the reporter molecules are single-stranded nucleic acid molecules (i.e. oligonucleotides). In some embodiments, the nucleic acid reporter molecules comprise a single binding region that is not only capable of interacting with the target nucleic acid but also of being captured on a second binding member. Typically, the interactions are reversible. The step of capturing on the second binding member may be achieved by means of an anchor group comprised in the reporter molecules, as has been described above for the capture molecules. In general, the specific binding region comprised in the reporter molecule is at least 12 nucleotides in length, e.g. at least 15 nucleotides, at least 18 nucleotides or at least 22 nucleotides. Particularly, the nucleotide sequence of the binding portion of the reporter molecules is complementary to the corresponding nucleotide sequence of the target nucleic acid.

The reporter molecules may be provided (e.g. in lyophilized/dry form) in one or more of the at least one reaction chamber of the device used in the invention prior to the introduction of the fluid sample to be analyzed. Thereby, the reporter molecules may be provided in the same one or more reaction chambers as the capture molecules and/or the first binding member or in at least one different reaction chamber. Alternatively, however, the reporter molecules may also be introduced into the device along with the sample (i.e. concomitantly) or after the sample has already been introduced.

In some embodiments, the reporter molecules and reporter specific capture molecules as described above compete for binding to a nucleic acid associated with a viral infection, that is, the respective binding regions comprised in the reporter specific capture molecules and the reporter molecules recognize the same or at least similar corresponding sequence(s) of the target nucleic acid. The term "similar sequences", as used herein, denotes sequences that differ only in one or more single nucleotide mismatches (i.e. non-complementary pairs of nucleotides) or by one or more single nucleotide additions, insertions or deletions (i.e. additional or lacking nucleotide residues). In other words, the respective binding regions comprised in the reporter specific capture molecules and the reporter molecules are at least partial identical. The term "partial identical", as used herein, denotes sequences differing only in one or more single nucleotides, as described above, or sequences having overlapping binding sites, that is sequences sharing a common nucleotide sequence but differ in at least one other part of the sequence region. However, it is also possible that the respective binding regions comprised in the competing capture molecules and the target nucleic acids recognize different, non-overlapping (e.g., adjacent) sequences of a reporter molecule but binding of either the capture molecule or the target nucleic acid to the reporter molecule sterically interferes with the binding of the other one. Typical reporter molecules for use in the present invention as well as a typical competitive assay for the detection of nucleic acids associated with viral infections are described herein.

The term "second binding member", as used herein, may refer to the same type of solid matrix as the first binding member (i.e. the first and second binding member may be identical) or to a different type of solid matrix. The second binding member may be provided in one or more of the at least one reaction chamber of the device used in the invention prior to the introduction of the fluid sample to be analyzed. Thereby, the second binding member may be provided in the same one or more reaction chambers as the capture molecules and/or the first binding member and/or the reporter molecules or in at least one different reaction chamber. Instead of providing the second binding member in the device prior to adding the sample, the second binding member may be introduced into the device along with the sample (i.e. concomitantly) or after the sample has already been introduced.

In some embodiments, the assay performed in the device further comprises:
   allowing reporter molecules to be released from the second binding member, released reporter molecules to form a complex with a nucleic acid associated with a viral infection, and reporter molecules not in complex with a nucleic acid associated with a viral infection to be re-captured on the second binding member;
   determining one or more values indicative for the amount of reporter molecules which are captured on the second binding member; and/or determining one or more values indicative for the amount of nucleic acids associated with a viral infection based on the values indicative for the amount of reporter molecules.

The step of releasing the reporter molecules from the second binding member may be accomplished by increasing the temperature in the one or more reaction chambers of the device, in which the second binding member is provided. The variation of the temperature may be achieved by employing one or more temperature control and/or temperature regulating unit as described above. Such a temperature increase may, for example, occur during the denaturation step of a PCR performed in the device. The forming of complexes between reporter molecules and a target nucleic acid and/or the re-capturing of reporter molecules not in complex with a target nucleic acid on the second binding member can be accomplished by decreasing the temperature in the respective one or more reaction chambers, for example during the annealing and/or elongation step(s) of a PCR. Experimental setups and temperature profiles for performing PCR amplifications are well established in the art. Thus, in some embodiments, the nucleic acids associated with a viral infection are further subjected to amplification, while allowing reporter molecules to be released from the second binding member, released reporter molecules to form a complex with a nucleic acid associated with a viral infection, and reporter molecules not in complex with a nucleic acid associated with a viral infection to be re-captured on the second binding member.

In some embodiments, the method further comprises introducing one or more agents each comprising one or more detectable moieties into the reaction chamber of the device before performing the actual detection reaction. That is, the agents comprising one or more detectable moieties may be introduced into the reaction chamber before introducing the sample (i.e. they may be provided in one or more reaction chambers), concomitantly with the sample, or after the sample has been introduced either directly or via a filling unit, as described above.

The term "agent comprising one or more detectable moieties", as used herein, refers to any compound that comprises one or more appropriate chemical substances or enzymes (i.e. one or more "moieties"), which directly or indirectly generate a detectable compound or signal in a chemical, physical or enzymatic reaction. Such an agent may thus be necessary for or will facilitate detection of the target nucleic acids and/or reporter compounds of interest by being capable of forming interactions with said target nucleic acids and/or reporter compounds. As used herein, the term is to be understood to include both detectable markers as such (also referred to as "labels") as well as any compounds coupled to one or more such detectable markers. Furthermore, moieties interfering with the generation of a detectable signal by a label (e.g., a quencher "hijacking" the emissions that resulted from excitation of the fluorophor, as long the quencher and the fluorophor are in close proximity to each other) also belong to the detectable labels. The detectable markers may also be part of or being coupled to the capture molecules and/or the target nucleic acids and/or the reporter molecules, for example in form of modified and/or labelled ribonucleotides, deoxynucleotides or dideoxynucleotides.

Detectable markers or labels that may be used are described above and include fluorescent labels.

The term "determining a value indicative for the presence and/or amount of nucleic acids associated with viral infections", as used herein, refers to the detection/determination of parameters such as electrical conductivity, redox potential, optical absorption, fluorescence intensity or bioluminescence that allow for qualitative and/or quantitative measurements of the target nucleic acids present in a given fluid sample. Only a single of these parameters may be determined but it is also possible to determine more than one parameter (e.g., electrical conductivity and the intensity of a fluorescence signal caused by a suitable label), either concomitantly or consecutively.

In some embodiments, the method further comprises the determination of one or more values indicative for the viral load in a patient based on the value indicative of the presence and/or amount of total nucleic acids associated with a viral infection. The term "viral load", as used herein, refers to the amount of viruses present in a given volume of blood (usually calculated as the copy number of viruses present per ml of blood). The virus copy number may be determined inter alia based on the total concentration of viral nucleic acids present in a given sample by employing appropriate computer software packages well known in the art (see above).

The detection reaction may be performed in a particular reaction chamber of the device used (also referred to as "detection chamber") or in a particular segment of a reaction chamber referred to as "detection zone" (e.g. an area located between those one or more parts of the base surface and/or the top surface of the reaction chamber that are made of a transparent material). For quantitative measurements, a device comprising a detection chamber and/or a detection zone having known volumes, respectively, may be employed.

The detection/determination of a value indicative for the presence and/or amount of the target nucleic acids may be performed only once or more than once during the assay performed. In case of more than one detection steps during a single assay the mean value of the results obtained is calculated. The data obtained in one or more cycles of detection may be analyzed and mathematically processed using appropriate computer software known by persons skilled in the art in order to determine inter alia the presence, the length or the sequence of one or more target nucleic acids and/or to calculate its/their amount.

According to another exemplary embodiment, the present invention relates to the use of a method, as defined herein, for detecting HIV in a given fluid sample, particularly in a whole blood sample (i.e. for determining the mere presence of the virus) as well as to the use for determining the HIV load in a patient (i.e. for determining the amount of virus present).

According to another exemplary embodiment, the present invention relates to the use of the amount of total viral nucleic acids, e.g. as determined by a method as defined herein, as a diagnostic marker. In particular embodiments, the total viral nucleic acids used as a diagnostic marker are HIV nucleic acids.

It has been found that sample fractionation or other processing steps may cause false-negative assay results because all those polynucleotides being present in the "discarded" portions of the sample will thus be distracted from further analysis. This is of particular importance not only in applications where the reliable detection of rare polynucleotides (i.e. nucleic acids present only in a very low copy number) is required, for example in order to prove the onset of a pathogenic condition at an early stage, but also in any uses aiming at the accurate quantitative determination of one or more polynucleotides present in a sample, e.g., for using this data as a marker for assessing disease state and/or progression.

For example, upon infecting their host viruses may immediately undergo replication resulting in an ongoing virus release and thus virus propagation and spreading. Additionally or alternatively, at least some types of viruses may run through a latency (i.e. quiescent) state before reproduction, e.g. in form of a provirus integrated into the host cell's genome. Thus, for determining whether a patient is infected by a particular virus the method may comprise not only detection of the nucleic acids originating from actively replicated virus particles but also of the pro-viral nucleic acids as intimate parts of the target cells themselves. Furthermore, viruses may occur as free particles or bound to the surface of host cells used as "transport vehicles". One clinically important example of a virus that may concomitantly occur in an infected patient as a free particle and/or as a particle attached to host cells and/or as a provirus is human immunodeficiency virus (HIV).

As already indicated above, the life cycles of viruses can be highly diverse. Typically, upon infection viruses replicate in the host cells from which the progeny is released after assembly of new viral particles. However, instead of immediately replicating upon infecting a host some viruses integrate their genetic information into the host cell's genome in form of a latent pro-virus. Furthermore, viruses may spread within the host solely in form of free viral particles circulating, e.g., in the bloodstream. Other viruses do not only occur as free viral particles but also in form of cell-associated viruses that remain attached, for example to blood cells, using them as transport vehicles. Notably, such diverse virus pools may also exhibit different life-spans (in vivo half-lives) in the host, that is, they may be detectable for different periods of time (cf. also FIG. 35). For example, in case of HIV infections it has been shown that free viruses circulating in the blood plasma have a life-span of 0.3 days (i.e. an in vivo half-life of 0.24 days) in average, whereas infected cells (e.g., leukocytes harboring a HIV provirus) have a mean life-span of 2.2 days (i.e. an in vivo half-life of 1.6 days) (see, for example, Perelson, A. S. et al. (1996) *Science* 271, 1582-1586).

Therefore, using a measure that includes all the different states of a viral life cycle and detects all different (spatially restricted) viral pools that may occur in a given host with high sensitivity is suitable to reliably detect a particular virus in an affected patient and/or to accurately determine the viral load. This may be of particular importance in patients having only a rather low viral load (e.g., less than 5000 viral copies/ml blood plasma or less than 2000 viral copies/ml blood plasma), where even minor changes in virus copy numbers may be indicative, e.g., for the onset of a re-infection or the incident efficacy of an antiviral therapy.

It has been found that the amount of total viral nucleic acids, particularly the amount of total viral nucleic acids in an untreated sample obtained from a patient, represents such a measure which may thus represent a superior clinical marker for diagnosing a viral infection.

For example, in case a patient has been infected with HIV, then the nucleic acids associated with the HIV infection that may be present in a whole blood sample obtained from that patient comprise RNA molecules originating from free HIV (i.e. virus particles freely circulating in the plasma), RNA molecules originating from cell-associated HIV (i.e. virus particles attached to any type of blood cells), pro-viral HIV DNA molecules being integrated into the host's genome, reverse transcribed HIV DNA molecules, and HIV transcripts derived from pro-viral DNA. However, a blood plasma sample obtained from the same patient only comprises RNA molecules originating from free HIV, since all other HIV nucleic acid species are associated with the patient's blood cells that have been removed. Therefore, it is evident that the amount of total HIV nucleic acids originating from a whole blood sample represents a more authentic diagnostic marker for HIV than the amount of total HIV nucleic acids originating from a blood plasma sample (cf. also FIG. 35)

The amount of total HIV nucleic acids used as a marker may be indicative for detecting HIV, determining the HIV load in a patient, monitoring disease progression in a patient infected with HIV and/or monitoring the efficiency of antiviral treatment of a patient infected with HIV. The amount of total HIV nucleic acids may comprise nucleic acids originating from free and from cell-associated viruses, which, in turn, may comprise RNA originating from free viruses, RNA originating from cell-associated viruses, pro-viral DNA, reverse transcribed viral DNA, and transcribed pro-viral RNA.

Referring to FIG. 1a, a method 100 for determination of molecular targets includes a lysing step 102 (for lysing a sample, for instance whole blood, in the presence of capture molecules with anchor groups), a complex formation step 110 (for forming a complex of HIV nucleic acids and capture probes with anchor groups, for instance hybridization), a capture step 114 (for capturing complexes onto a solid matrix, via anchor groups), a wash step 118 (for removing all unbound material, for instance nucleic acids, proteins, low molecular weight contaminants etc.), an amplification step 120 (for amplifying and labelling captured nucleic acids) and a detection step 126 (for detecting amplicons). According to method 100, polynucleotides are released from one or more target pathogens of a sample. Released polynucleotides that are associated with the target pathogens are captured at a surface. The captured polynucleotides are separated from concomitant materials (for instance, amplification inhibitors) of the sample. The separated captured polynucleotides are amplified to form amplicons. The presence of the polynucleotides is determined by detecting the amplicons. Because the amplified polynucleotides are associated with the target pathogens, the presence and/or identity of the one or more target pathogens can be determined (for instance, qualitatively and/or quantitatively). In an exemplary embodiment, method 100 includes determination of viral load based on a determination of one or more viruses present in a blood sample. Next, various steps of method 100 will be discussed.

In lysing step 102, polynucleotides 106 are released from pathogens present in a blood sample 104. Polynucleotides can be released from target pathogens as desired (for instance, thermally, chemically, mechanically, or by combination thereof). In an exemplary embodiment, polynucleotides are released by combining sample 104 with a lysing liquid that includes materials that lyse pathogens in the sample. Examples of liquids capable of lysing pathogens are found in Boom R., Sol C. J., Salimans M. M., Jansen C. L., Wertheim-van Dillen P. M., van der Noordaa J., Rapid And Simple Method For Purification Of Nucleic Acids, J. Clin. Microbiol. 1990 March; 28(3):495-503, which is incorporated herein by reference.

An exemplary lysing liquid includes one or more of a denaturant (for instance, guanidine thiocyanate (GuSCN) (for instance, about 4.57 M)), a pH buffer (for instance, Tris-HCl, (for instance, pH 6.4, 45 mM), a chelator (for instance, EDTA 20 mM), and a detergent (for instance, Triton X-100 1.2% (w/v) and/or saponin (for instance, 0.2%)), a salt (for instance, $MgCl_2$ (for instance, 75 mM) and/or $ZnCl_2$ (for instance, 1 mM)).

Lysing step 102 typically includes forming a mixture comprising released polynucleotides 106, concomitants of sample 104 (for instance, cellular components, amplification inhibitors, proteins, and other materials), and capture molecules 108i. Each capture molecule 108i includes a polynucleotide binding portion 109i and a biotin anchor group 111. Each polynucleotide binding portion 109i is a polynucleotide sequence complementary to (for instance, specific for) a different region of polynucleotide 106. For example, capture molecule 108a includes a binding portion 109a complementary to a target region 113 of polynucleotide 106 and capture molecule 108b includes a binding portion 109b complementary to a different target region 115 of polynucleotide 106. Typically, at least one (for instance, two or more, three or more, four or more) different capture molecules are used for each polynucleotide to be determined.

In some embodiments, polynucleotides 106 are released from target pathogens in the presence of capture molecules 108i. This can be accomplished by, for example, essentially simultaneously combining sample 104 with the capture molecules 108i and lysing liquid components. Sample 104 may be combined with the capture molecules 108i and components of the lysing liquid may be combined with the capture molecules 108i and lysing liquid components a liquid state or in a dried (for instance, lyophilized) state.

In alternative embodiments, polynucleotides are released from pathogens of sample 104 and the resulting mixture is combined with capture molecules 108i. For example, sample 104 and the lysing liquid components excluding capture molecules 108i may be combined and allowed to incubate for a period of time prior to combining the incubated mixture with capture molecules 108i.

In an exemplary embodiment, polynucleotides 106 are HIV-RNA and binding portions 109i of capture molecules 108i are complementary to regions thereof.

Turning to complex formation step 110, one or more capture molecules 108i combine with (for instance, hybridize with) polynucleotide 106 to form a complex 112. Complex formation step 110 can be performed by, for example, allowing released polynucleotides 106 to incubate for a period of time in the presence of capture molecules 108i sufficient to form complexes 112. In some embodiments, the incubation period is at least about 60 seconds (for instance, at least about 120 seconds, at least about 360 seconds). In some embodiments, the incubation period is about 600 seconds or less (for instance, about 480 seconds or less, about 420 seconds or less). In an exemplary embodiment, the incubation period is about 5 minutes.

For each polynucleotide to be determined, the total concentration of capture molecules 108i is typically sufficient to capture most (for instance, at least 60%, at least 75%, at least 90%, essentially all) of the polynucleotide in complexes 112. In some embodiments, the concentration of each of one or more (for instance, most or all) of capture molecules 108i is at least about 0.1 µM (for instance, at least about 0.25 µM, at least about 0.5 µM). The concentration in of each of one or more (for instance, most or all) of capture molecules is typically about 2 µM or less (for instance, about 1.5 µM or less, about 1 µM or less). In an exemplary embodiment, the concentration of each of one or more (for instance, most or all) of capture molecules is about 0.625 µM.

Turning to capture step 114, complexes 112 and capture particles 117 are combined to form capture complexes 119. Each capture complex 119 includes one or more complexes 112 and a capture particle 117. Complexes 112 are typically bound non-selectively to particle 117. Each capture particle 117 includes a streptavidin capture surface 116. Capture particles 117 capture each complex 112 by interaction between one or more biotin anchor groups 111 of capture molecules 108i and streptavidin capture surface 116. Exemplary capture particles 117 include streptavidin sepharose beads (Amersham) having a diameter of about 34 µm pre-washed with $diH_2O$ to remove ethanol. Approximately 10000 to 20000 beads are used per assays, corresponding to a binding capacity of about 3 nmol of biotin per 10 µl of whole blood.

Typically, capture step 114 is initiated after incubating sample 104 with polynucleotides 106 and capture molecules 108i for a time sufficient to form complexes 112. For example, sample 104 can be incubated in the presence of the lysing liquid and capture molecules 108i prior to combining the resulting mixture with capture particles 117.

Typically, the total concentration of capture molecules 108i and particles 117 is sufficient to quantitatively capture each of one or more selected polynucleotides 106 associated with each of one or more target pathogens in sample 104. Thus, for each polynucleotide 106 to be determined, substantially all (for instance, at least 75%, at least 90%, at least 95%, at least 97.5%, or essentially all) of the polynucleotide is captured by capture molecules 108i and particles 117.

Turning to wash step 118, capture complexes 119 are separated from concomitant material (for instance, nucleic acids, proteins, cellular components, lysing reagents, and the like) not captured by particles 117. In some embodiments, capture complexes 119 are filtered using a filter with pores small enough to prevent passage of complexes 119 but large enough to permit passage of material not captured by particles 117.

Capture complexes 119 can be washed with a wash liquid to enhance separation of concomitant material. In some embodiments, at two or more different wash liquids are used. In some embodiments, a first wash liquid contains a detergent to remove low molecular weight substances, proteins and other cellular components adhering to the particles via hydrophobic interaction and a second wash liquid removes the detergent which might otherwise interfere with the subsequent amplification process. An exemplary first wash liquid includes 0.15 M LiCl, 0.1% SDS (since SDS is a PCR inhibitor, it may be removed prior to a PCR procedure), 10 mM Tris-HCl pH 8.0, and 1 mM EDTA). An exemplary second wash liquid includes 0.15 M LiCl, 10 mM Tris-HCl pH 8.0, 1 mM EDTA. Suitable wash liquids are described in, for example, U.S. patent publication number 20040215011A1.

Turning to amplification step 120, polynucleotides 106 are amplified using probes 122. Typically, the amplification is a PCR amplification. In an exemplary embodiment, polynucleotides 106 are RNA and the amplification is RT-PCR. In some embodiments, the pathogen is HIV.

Figure 1C:
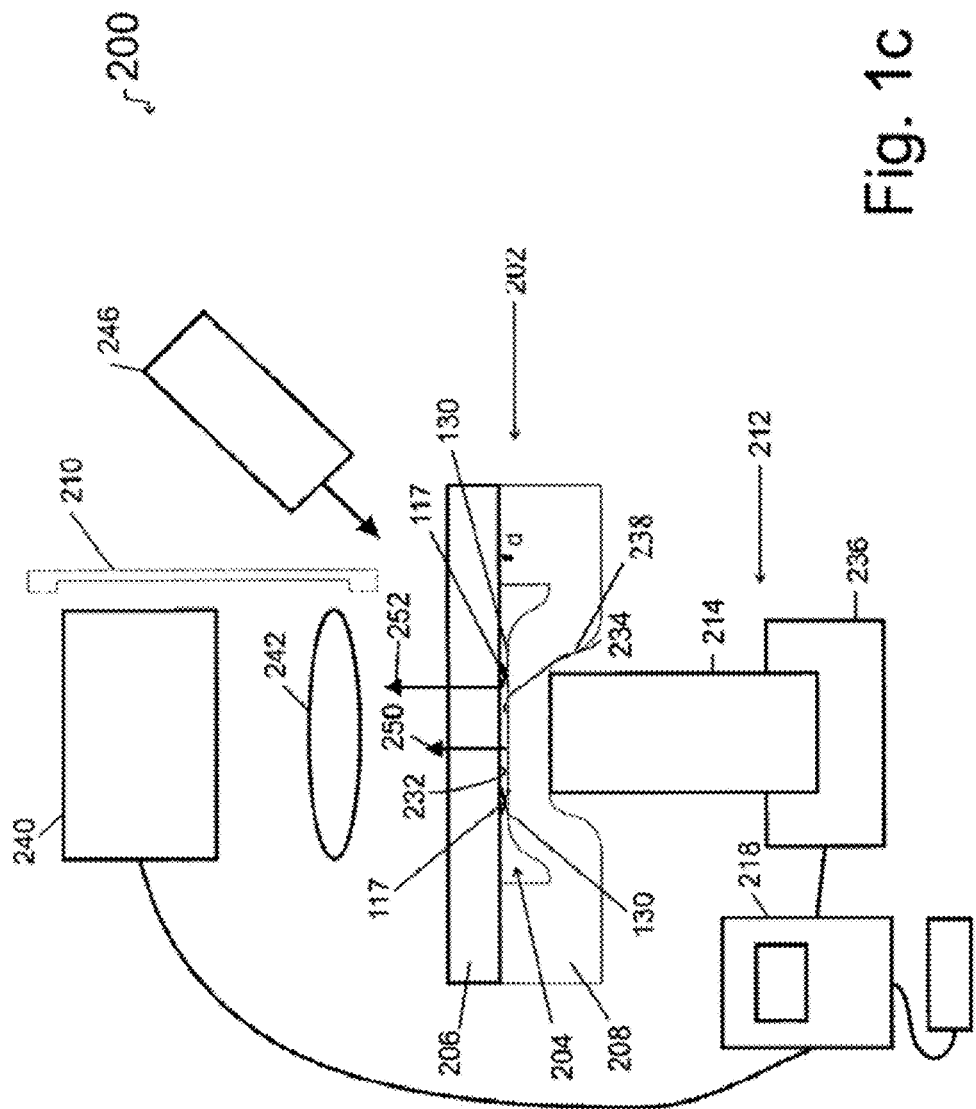
FIG. 1c is a view of the detection system of FIG. 1b, with the detection system being shown in an actuated state for performing a detection step of the method of FIG. 1a according to an exemplary embodiment.
Figure 1D:
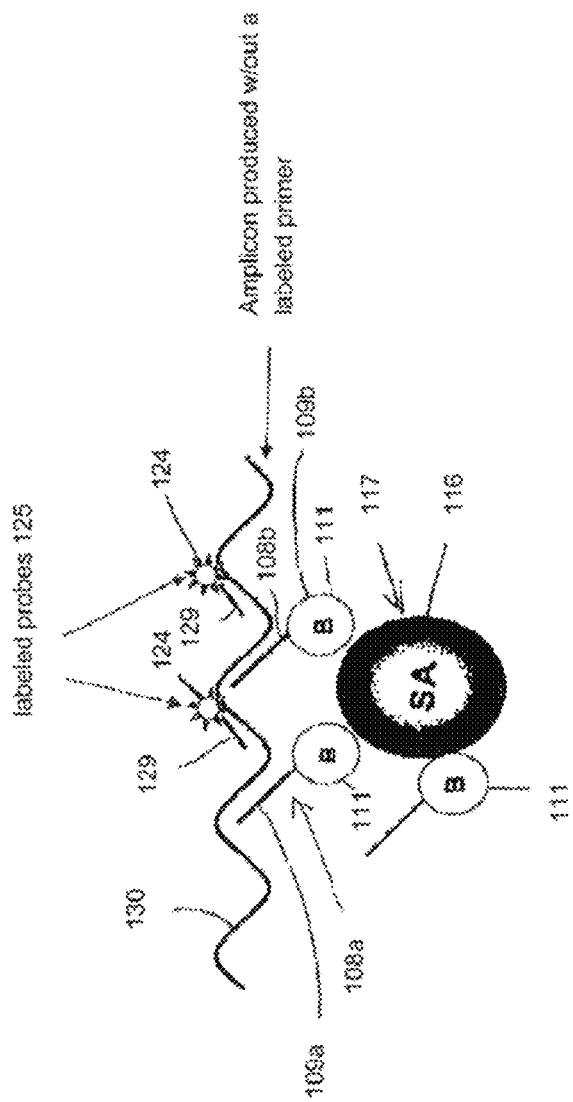
FIG. 1d shows an amplicon bound to a particle.

Referring to FIG. 1d, in some embodiments, amplification step 120 produces amplicons 130. Under hybridizing conditions (for instance, temperatures), amplicons 130 are captured by the immobilized capture probe molecules 108a, 108b and 108c at streptavidin surface 116 of particles 117. Amplicons are labelled with a fluorescent a labelling agent 125 comprising an optical label 124 (for instance, a fluorescent label) and a polynucleotide portion 129 complementary to a region of the amplicon 130.

Referring to FIG. 1e, in an alternative embodiment, each probe 122 includes an optical label 124 (for instance, a fluorescent label). Other probes 108*j* include a polynucleotides portion 109*j* complementary to a region of amplicon 130 and also carries a biotin anchor group 111. Probe molecules 108*j* are captured to the streptavidin surface 116 of particles 117. Amplification step 124 produces directly labelled amplicons 130, each including a label 124. Amplicons 130 are captured by the immobilized probe molecules 108*j* onto the streptavidin surface 116 of particles 117. Binding portions 109*j* of probes 108*j* may be the same as, or different from, probes 108*i* used in capture step 114. Probes 108*j* and/or beads 117 can be combined with polynucleotides 106 along with other components used to perform amplification step 120.

In detection step 126, amplicons 130 are detected (for instance, by fluorescent detection of labels 124. Detection step 126 can be performed with amplicons 130. captured at streptavidin surface 116 of particles 117. Detection step 126 can be performed without first combining amplicons with a liquid free of probes 122. For example, detection step 126 can be performed with captured amplicons 130 present between first and second surfaces after reducing a distance the surfaces. An embodiment of this method for performing detection step 126 is discussed next with respect to FIG. 1*b* and FIG. 1*c*.

Referring to FIG. 1*b* and FIG. 1*c*, a system 200 for performing at least detection step 126 of method 100 includes a microfluidic cartridge 202, a detection system 210, a stencil actuator 212, and a processor 218, in communication with detection system 210 and actuator 212.

Cartridge 202 includes a first substrate 206 and a second substrate 208, which together define a detection chamber 204. First substrate 206 is typically optically transmissive (for instance, clear) with respect to a wavelength of light useful for exciting and detecting fluorescence from labels 124 of amplicons 130. First substrate 206 can be formed of, for example, a polymer, glass, or silica. Second substrate 208 is formed of a pliable or flexible material (for instance, an elastomeric polymer). First substrate 206 is generally less flexible than second substrate 208.

Actuator 212 includes a stencil 214 and a stencil driver 236 configured to drive stencil toward and away from second substrate 208. Stencil driver 236 can be actuated by, for example, compressed air, electromagnets, piezo electric or another suitable actuation. As seen in FIG. 1*c*, when actuated toward a wall 238 of second substrate 208, stencil 214 reduces a distance "d" between inner wall 232 of first substrate 206 and inner wall 234 of second substrate 208. In the reduced distance state of FIG. 1*c*, at least some capture particles 117 with captured amplicons 130 remain between surfaces 232, 234. In contrast, much of the liquid surrounding particles 117 is displaced from between surfaces 232, 234.

Detection system 210 is configured to detect the presence of amplicons 130 with cartridge 202 in the reduced distance state of FIG. 1*c*. Detection system 210 includes a light source 246 (for instance, a laser), an imaging detector 240, and an optical system 242. In use, light source 246 illuminates material present between inner surfaces 232, 234 of substrates 206, 208. Fluorescence 250 emitted from labels 124 from amplicons 130 is detected. The detected fluorescence 250 is indicative of the presence of amplicons 130. Processor 218 receives a signal from detection system 210 indicative of the detected fluorescence. Processor 218 can determine the presence of amplicons 130 and, therefore, the presence of the corresponding pathogens in sample 104.

In general, liquid remaining between inner surfaces 232, 234 emits background fluorescence 252 not associated with the presence of amplicons 130. The intensity of background fluorescence 252 is generally proportional to the amount of liquid remaining between inner surfaces 232,234. The intensity of label fluorescence 250 from labels 124 of amplicons 130, however, is spatially localized in the vicinity of particles 117. Imaging detector 240 receives and detects both label fluorescence 250 and background fluorescence 252. However, because of the displacement of liquid from between inner surfaces 232,234 in the reduced distance state of FIG. 1*c*, the signal-to-noise of label fluorescence 252 relative to background fluorescence 250 is higher than in the un-reduced state of FIG. 1*b*.

An exemplary embodiment of method 100 can be performed as follows. Between about 5 and 10 µl of capillary blood (for instance finger tip, earlap) is obtained from an individual. The blood sample is combined with about 90 µl of a lysis buffer including lysing components and capture molecules 108*i*. The resulting mixture is incubated with agitation for about 5 min at 21° C. The incubated mixture is combined with an amount of particles 117 equivalent to about 10 µl of slurry, corresponding to a binding capacity of 3 nmol biotin, i.e. particles are purchased as a slurry of particles in 20% ethanol). The mixture with particles is incubated with agitation for about 5 min at 21° C. After incubation, supernatant is removed by the stencil actuator system 350 for operating cartridge 300. The particles are washed with a first wash buffer (for instance, 3 times with 50 µl volume each time) and then with a second wash buffer (for instance, 3 times with 50 µl each time). After washing, the supernatant is removed. The washed particles are combined with an amplification medium and subjected to qRT-PCR amplification for detection (for instance, quantization) of captured polynucleotides 106.

Referring to FIG. 14, fluorescence from amplicons 130 is detected (for instance, using the reduced distance mode of an instrument such as that shown in FIG. 1*b* and FIG. 1*c*). Amplicons 130 can be detected after each of multiple different heating and cooling cycles of the amplification. In this way, the build up of amplicon concentration can be followed in time. Amplicons are typically detected while bound to particles 117.

While method 100 has been described as including a step of releasing polynucleotides from pathogens, method 100 can include other steps for providing polynucleotides. In some embodiments, polynucleotides are released from non-pathogenic cells (for instance, plant, human, animal, or the like). In some embodiments, the polynucleotides are products of a gene expression analysis. In some embodiments, polynucleotides are provided without requiring a releasing step and/or as polynucleotides already released from a cell or other biological sample. Next, an embodiment of an assay system and a microfluidic cartridge will be discussed typically capable of performing most (for instance all) steps of method 100.

Referring to FIG. 2, a microfluidic cartridge 300 includes a first substrate 301, a second substrate 303 and a micro fluidic network 305. First and second substrates 301,303 may have properties similar to those described for substrates 206,208 of cartridge 202.

Microfluidic network 305 is configured to receive a sample and various reagent materials, permit operations to be performed on these materials (for instance, mixing, transport, and incubation), and to facilitate detection of amplicons indicative of the presence of one or more target pathogens.

Microfluidic network 305 includes a sample inlet 302 connected by a channel 304 to a lysis chamber 306, which is connected by a channel 308 and a junction 307 to a detection chamber 332; a first liquid inlet 310 is connected by a channel 312 to a first reagent chamber 314, which is connected by a channel 316 to junction 307; a second liquid inlet 318 is connected by a channel 319 to a second reagent chamber 320, which is connected by a channel 322 to junction 307; and a third liquid inlet 324 is connected by a channel 326 to an amplification-labelling reagent chamber 328, which is connected by a channel 330 to junction 307. Junction 307 is connected to a waste chamber 334 via a waste channel 336. Detection chamber 332 is connected to waste chamber 334 via a waste channel 340, which includes a filter sized to prevent passage of particles but to permit passage of un-capture material as describe in wash step 118 of method 100.

Typically, reagent chambers 306, 314, 320, 328 include lyophilized reagents (for instance, as pellets) used to perform steps as described for method 100. In use, a liquid (for instance, water, buffer, aqueous solvent, or other liquid) is introduced to the inlet corresponding to a chamber. The liquid solubilises the lyophilized reagents to form a liquid. In an exemplary embodiment, lysis chamber 306 includes lyophilized reagents to facilitate lysing of target pathogens and capture molecules corresponding to polynucleotides of pathogens. Typically, lyophilized reagents of chamber 306 are solubilised by the sample (for instance, a whole blood sample) alone or in combination with added liquid. In an exemplary embodiment, chamber 314 includes lyophilized reagents to form a wash liquid (for instance, a first wash liquid (buffer)) when combined with a liquid introduced to inlet 310. In an exemplary embodiment, chamber 320 includes lyophilized reagents to form a wash liquid (for instance, a second wash liquid (buffer)) when combined with a liquid introduced to inlet 318. In an exemplary embodiment, chamber 328 includes lyophilized reagents to form an amplification mixture (for instance, a second wash liquid (buffer)) when combined with a liquid introduced to inlet 324.

Prior to use of device 300, particles 117 are typically disposed within network 305 downstream of chamber 306. For example, particles 117 may be disposed within detection chamber 332 prior to use. Particles 117 can be washed with liquids from chambers 306,314,320,328 by appropriate actuation of stencils as discussed next.

Referring to FIG. 3, micro fluidic cartridge 300 is shown in combination with a stencil actuator system 350 for operating cartridge 300. Actuator system 350 includes an actuator base 352 and multiple stencils 354i. Each stencil 354i is actuated by a corresponding stencil driver similar to stencil driver 236. In use, cartridge 300 is positioned with flexible substrate 303 facing actuator base 352 and stencils 354i. Each stencil 354i corresponds spatially to a different location of microfluidic network 305. For example, stencil 354d corresponds to waste channel 336. When actuated, stencil 354d compresses substrate 303 overlying channel 336 thereby obstructing channel 336 and preventing the passage of fluid there along.

Thus, the flexible property of the second substrate 303 or cover element ensures that it can be deformed in a reversible manner when a stencil 354i exerts a mechanical force onto a dedicated portion of the flexible second substrate 303. In other words, if a reversible valve action is desired, the deformation of the second substrate 303 is reversible to that extent that when the force applied by the stencil 354i is removed, the second substrate 303 returns towards its original position such that fluid can again pass along a corresponding channel 336.

In contrast to this, the rigid property of the first substrate 301 refers to the fact that the material of the first substrate 301 is configured in such a manner that, upon exertion of a force by a stencil 354i onto the first substrate 301, no deformation of the first substrate 301 occurs which could have an influence on the valve function. Consequently, the second substrate 303 provides for flexibility, whereas the first substrate 301 provides for stability.

Other stencils correspond similarly to other channels of network 305. Stencils 354a, 354c respectively correspond to waste channel 340 and junction 307. Actuation of stencils 354a, 354c seals detection chamber 332 allowing multiple heating and cooling cycles to be performed without significant loss of liquid therein. Filter 341 permits particles 116 within chamber 332 to be washed with liquids from chambers 306,314,320,328 without loss of the particles. Still other stencils respectively correspond to chambers 306, 314, 320, 328, and 332. Repetitive actuation of these stencils can be used to agitate material (for instance, liquid) within the chambers to facilitate mixing (for instance, of samples and reagents). Sequential actuation of stencils along a channel can be used to move liquids along the channel. Contents of a chamber can be emptied by, for example, actuation of respective stencils operating upstream, downstream, and upon the chamber.

In one embodiment, the substrate is sufficiently reversible in that upon repeated stencil actuations and removals (e.g. at least ten, or at least fifty), the substrate returns toward its original position so that the portion of a micro fluidic network underlying a particular stencil can be repeatedly obstructed and reopened.

Cartridge 300 can be operated as follows. An amount (for instance, between about 5-10 µl) of sample (for instance, whole blood) and an optional amount (for instance, between about 5 and 50 µl) of liquid (for instance, water) is introduced to chamber 306 network 305 via inlet 302. An amount of liquid (for instance, between about 20 and 200 µl) is introduced to chambers 314,320,328 via corresponding inlets. The respectively introduced sample and optional liquid resolublises lyophilized reagents present in chambers 306,314,320,328. Stencils corresponding to each chamber are actuated to agitate the liquid reagent mixture therein to facilitate mixing. Within lysis chamber 306, the lysis buffer releases polynucleotides 106 from pathogens (for instance, as in lysing step 102). The released polynucleotides combine with capture molecules 108i to form complexes 112 (for instance, as in complex formation step 110).

The lysing mixture of chamber 306 is moved to the detection chamber 332 and combined with particles 116 and incubated to form capture complexes 119 (for instance, as in capture step 114). The mixture within chamber 332 can be agitated for instance using a stencil. At the end of the capture step 114 incubation, liquid/supernatant is removed from detection chamber 332 to waste chamber 334 with the stencil actuator system 350 for operating cartridge 300.

After removal of liquid/supernatant from waste chamber 332, wash liquid from chambers 314,320 is moved through chamber 332 to separate concomitants from complexes 119 (for instance, as in wash step 118). Chamber 332 can be agitated via stencil 354b during washing.

After separating concomitants from complexes 119 within chamber 332, amplification reagents from chamber 328 are moved to detection chamber 332 and the resulting contents are subjected to multiple PCR cycles (for instance, as in amplification step 120).

After each of one or more amplification cycles, stencil 354b is actuated to reduce a distance between opposed inner surfaces of detection chamber 332. Complexes 119, if present, remain trapped between the inner surfaces whereas other contents are relatively displaced as discussed with respect to device 200 in FIG. 1c. Detection is typically performed using a fluorescence detection system (for instance, as described for device 200). Detection is typically performed with amplicons 130 of complexes 112 in the hybridized state and bound to particles 117 as complexes 119 (for instance, as in detection step 126). After each cycle, the population of amplicons 130 increases. The fluorescence intensity resulting from capture complexes 119 increases accordingly. The fluorescence intensity increase with cycle number can be monitored to determine the threshold cycle at which the amplicons 130 can by quantitized. Because polynucleotides 106 are captured quantitatively (for instance, as in capture step 114), the quantitative detection of amplicons 130 permits the amount of polynucleotides 106 present in the sample to be determined quantitatively. Thus, for example, where the pathogen is a virus (for instance, HIV), the viral load within the sample (for instance, whole blood) can be determined.

Cartridge 300 may further include an array including multiple immobilized polynucleotides each corresponding to a polynucleotide sequence of a different pathogen subtype. After detection step 126, hybridization of amplicons 130 is performed to determine the pathogen subtype. In an exemplary embodiment, the array includes polynucleotides configured to determine a subtype of HIV.

While operation of cartridge 300 has been described as including the addition of liquid reagents, liquid reagents may be stored on the cartridge as in blister packs and released during use.

Other examples of systems suitable for optically determining the presence of label 124 are described in each of the following applications: the U.S. continuation of International Patent Application PCT/EP2005/004923, filed on May 6, 2005, which designates the United States and claims priority to German Patent Application DE 10 2004 022 263, filed May 6, 2004, the U.S. continuation having serial no. U.S. Ser. No. 11/593,021 and being filed Nov. 6, 2006.

Next, referring to FIG. 4 to FIG. 16, various steps during an analysis procedure according to an exemplary embodiment will be explained.

Figure 4:
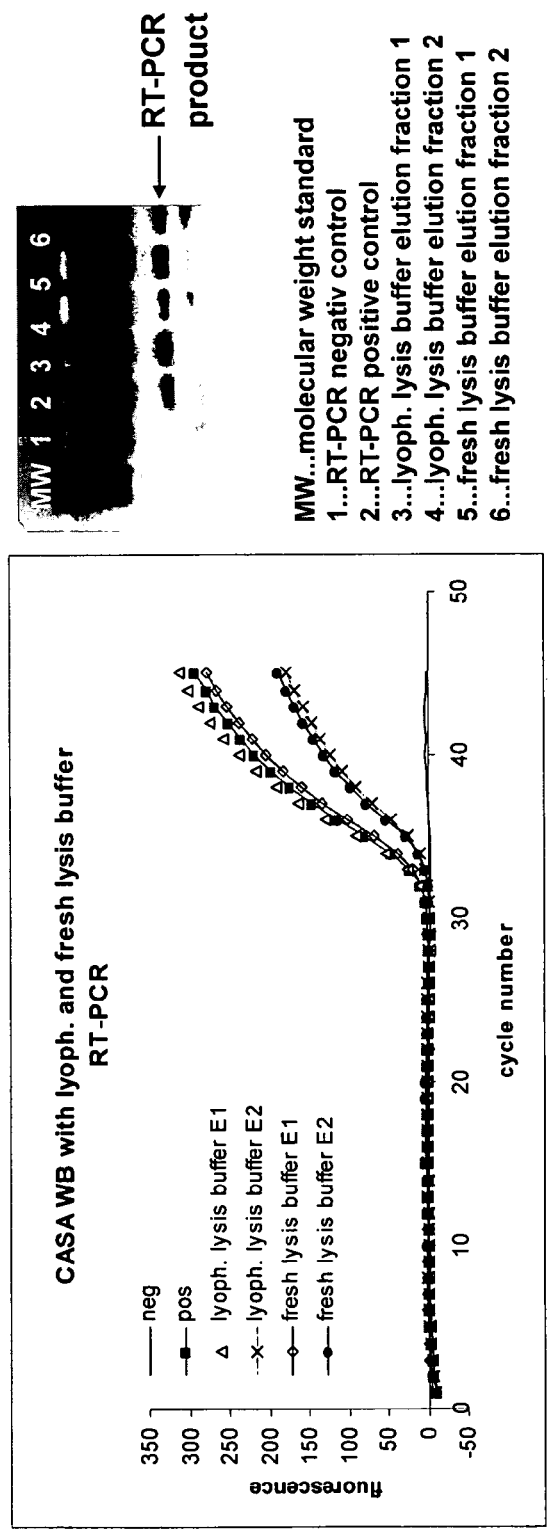
FIG. 4 shows the results (RT-PCR product curves and gel electrophoresis) of assays performed with either fresh or lyophilized lysis buffer, wherein the lysis buffer can be stored as lyophilized pellet without loss of function.
Figure 5:
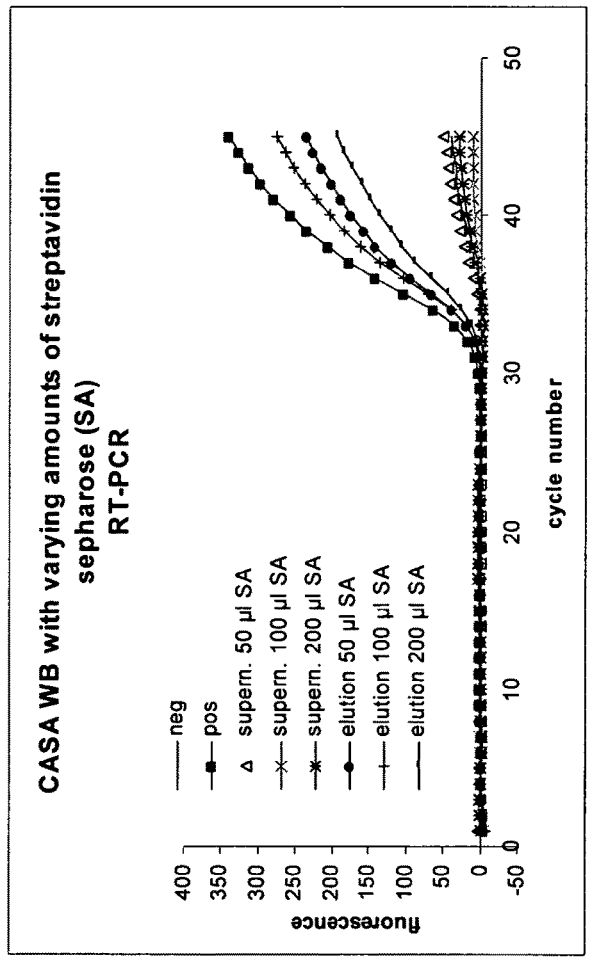
FIG. 5 shows the effect of the amount of streptavidin sepharose slurry used to capture an oligonucleotide (i.e. HIV RNA) from a blood-lysis mixture, wherein the results of assays performed with 200 µl, 100 µl or 50 µl of streptavidin sepharose slurry reveal that binding capacity of 50 µl of slurry is sufficient to capture substantially all RNA molecules.
Figure 7:
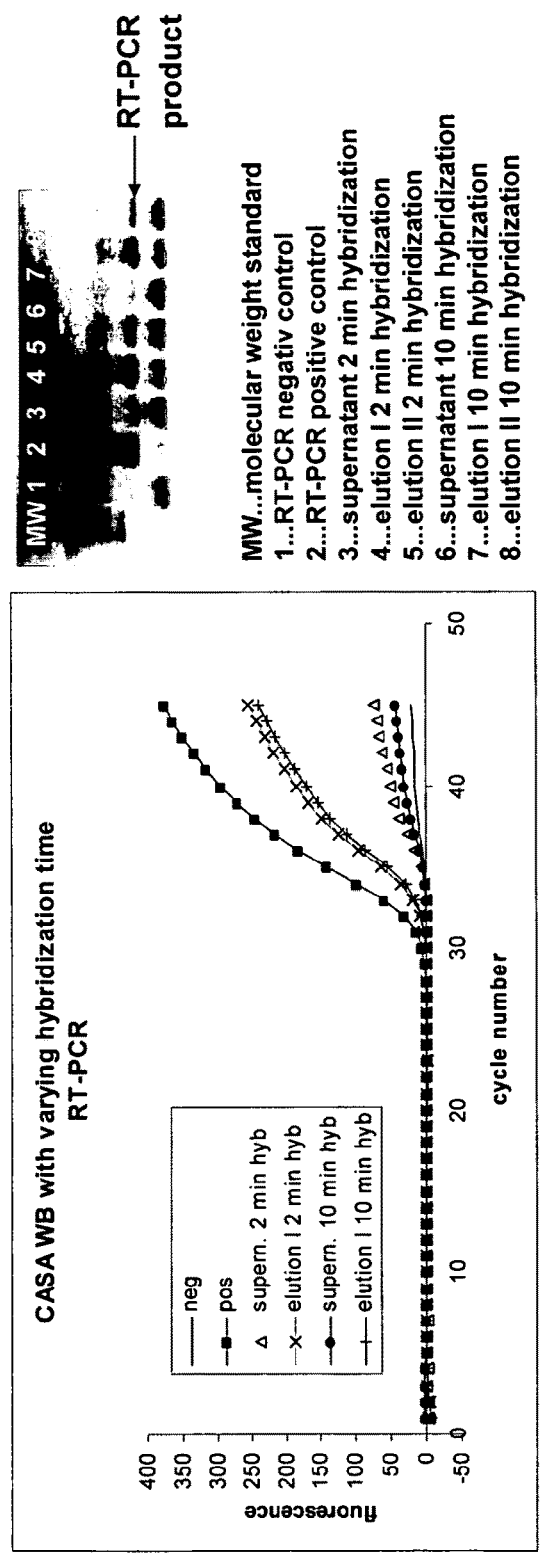
FIG. 7 shows the effect of the incubation time for the complex formation (i.e. hybridization) between the polynucleotide to be analysed and the capture probes, wherein a substantial amount of polynucleotide is not recovered after 2 min of incubation time, while after 10 min of incubation no RNA can be detected in the supernatant.
Figure 8:
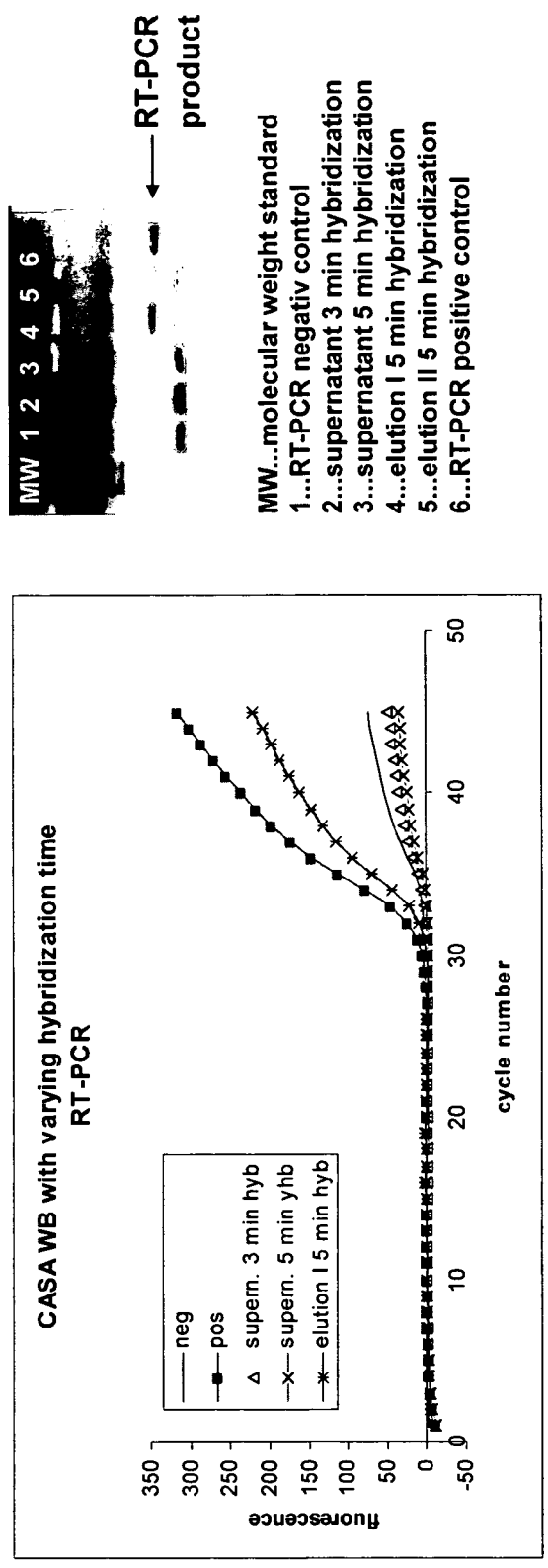
FIG. 8 shows the effect of the incubation time for the complex formation (i.e. hybridization) between the polynucleotide to be analysed and the capture probes.
Figure 9:
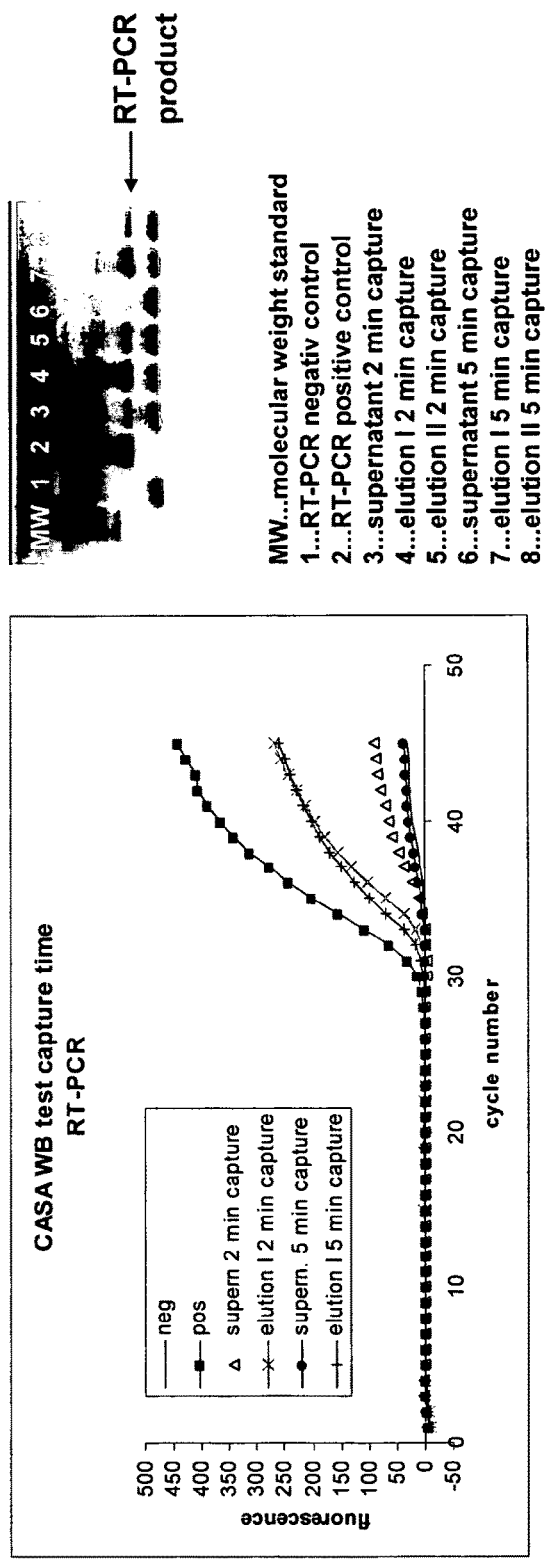
FIG. 9 shows the effect of the incubation time for the capture step (i.e. binding of the biotin anchor groups of the complexes to the streptavidin sepharose particles), wherein it is shown that 5 minutes of incubation time are sufficient to capture all polynucleotide molecules (i.e. no RNA molecules are detected in the supernatant).
Figure 10:
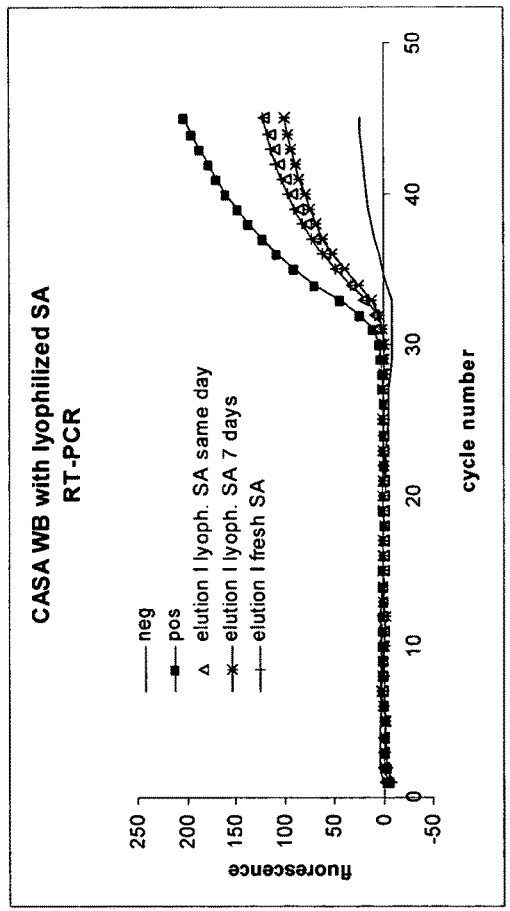
FIG. 10 show the results (RT-PCR product curves) of assays performed with either fresh or lyophilized strepavidin sepharose particles after storage of several hours or seven days, wherein the strepavidin sepharose particles can be lyophilized and reconstituted without loss of function.

FIG. 4 illustrates a lysis.

FIG. 5 to FIG. 10 illustrate capturing of RNA complexes onto a solid matrix.

Figure 11:
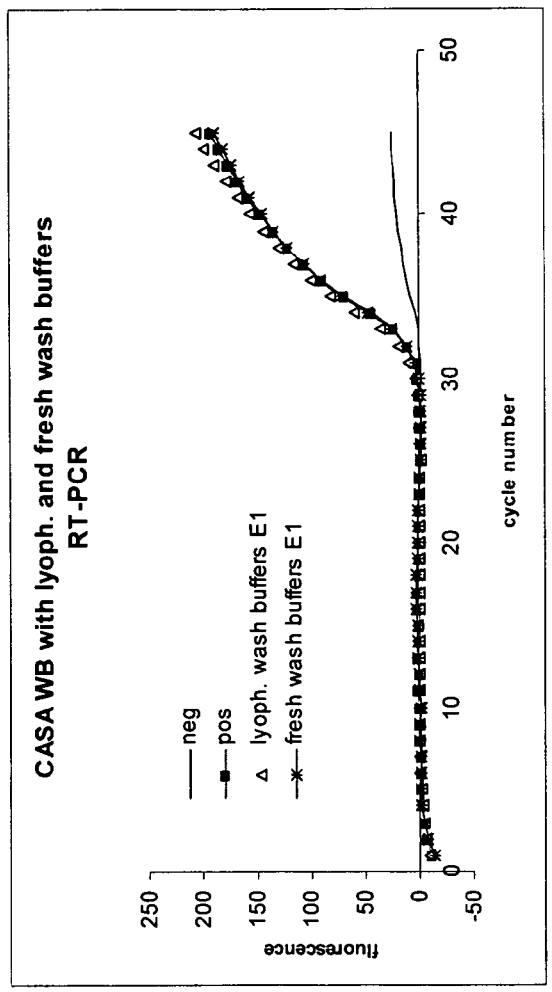
FIG. 11 show the results (RT-PCR product curves) of assays performed with either fresh or lyophilized wash buffers, wherein the wash buffers can be lyophilized and reconstituted without loss of function.

FIG. 11 illustrates washing.

Figure 12:
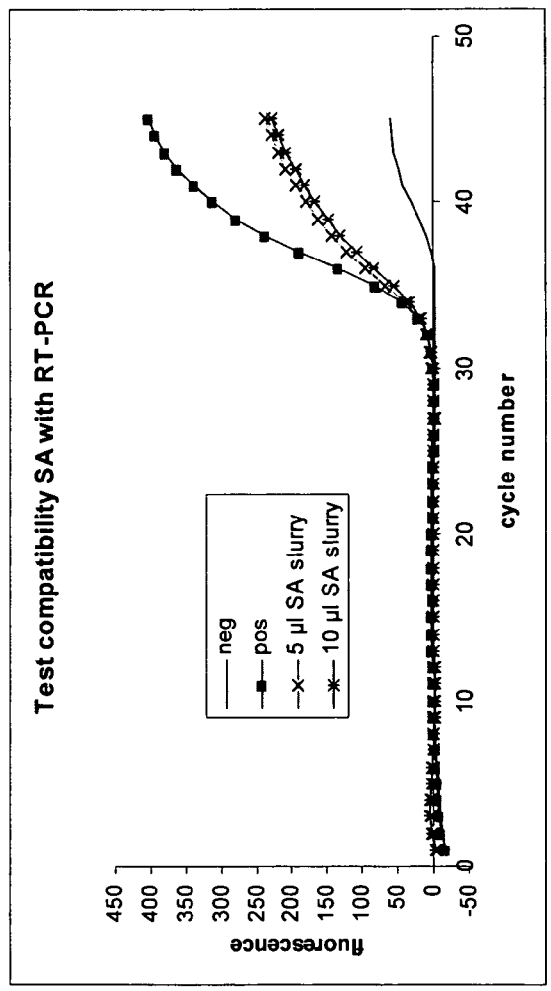
FIG. 12 show the results (RT-PCR product curves and agarose gel electrophoresis) of tests performed to show the compatibility of the strepavidin sepharose particles with RT-PCR, wherein 10 µl of strepavidin sepharose particle slurry can be applied to a RT-PCR amplification without loss of amplification efficiency.
Figure 13:
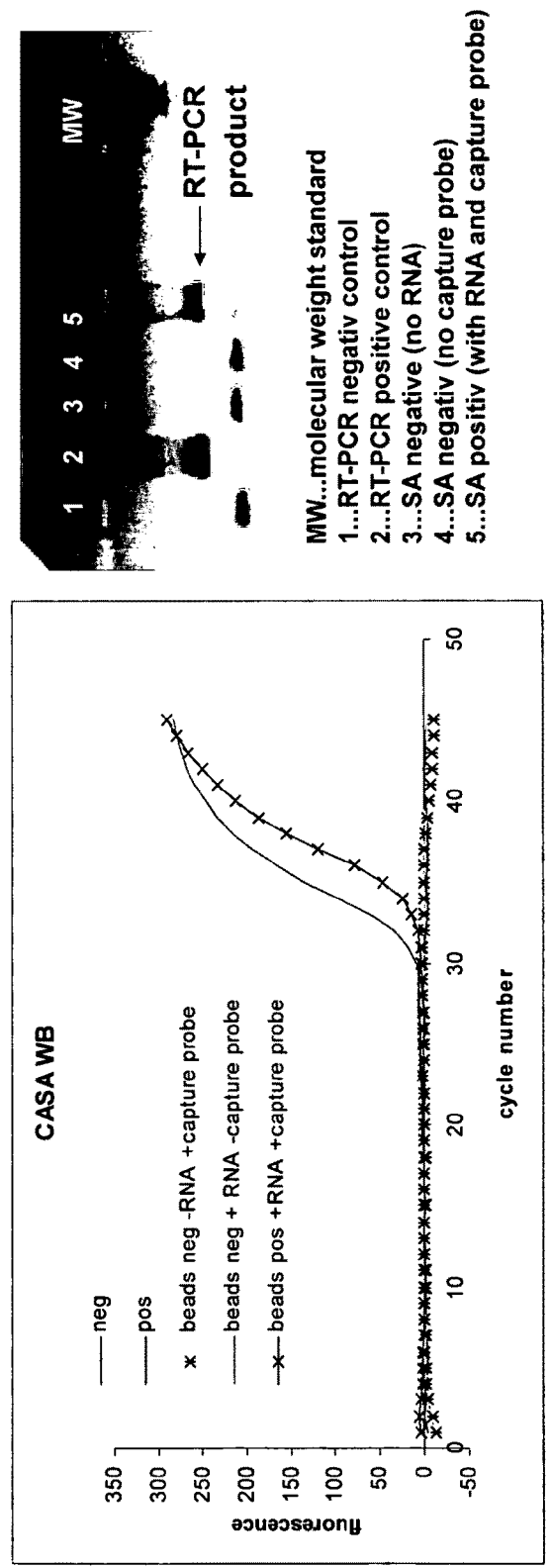
FIG. 13 shows the specificity of the assay according to an exemplary embodiment, wherein the results (RT-PCR product curves and agarose gel electrophoresis) show that neither the HIV-RNA binds non-specifically (i.e. in the absence of capture probes) to the strepavidin sepharose particles nor does any RNA of human blood cells which is also released during the lysis step is captured/amplified.

FIG. 12 and FIG. 13 illustrate amplification.

FIG. 14 to FIG. 16 illustrate detection.

Figure 17A:
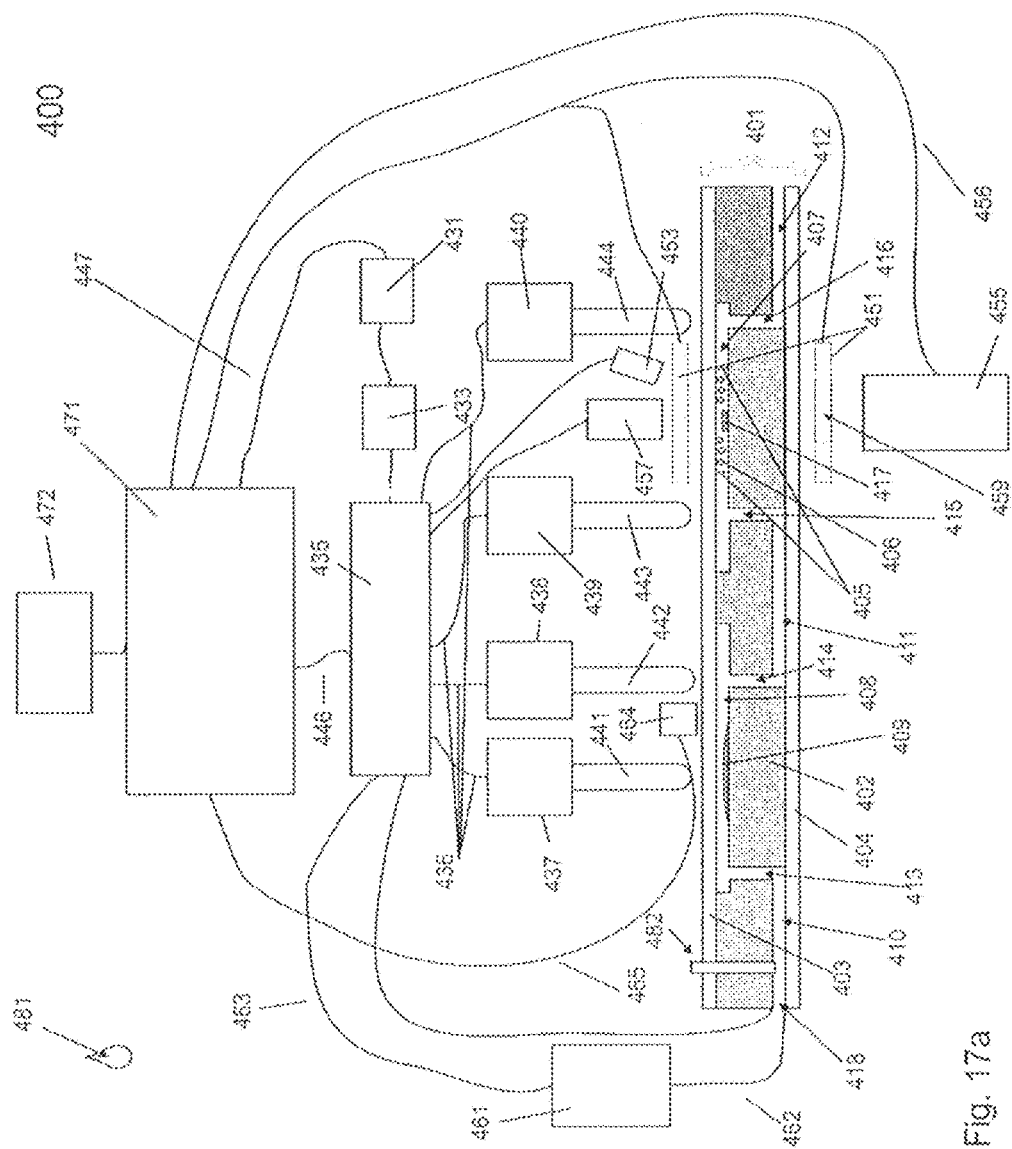
FIG. 17a illustrates the device performing at least the steps of capturing the targets from a sample, amplification of the target and detection of one or more values indicative of the presence of the target in the sample.

FIG. 17a. illustrates an exemplary system 400 for performing at least the steps of capturing targets from a sample, amplification of the target and detection of one or more values indicative of the presence of the target in the sample.

Figure 17B:
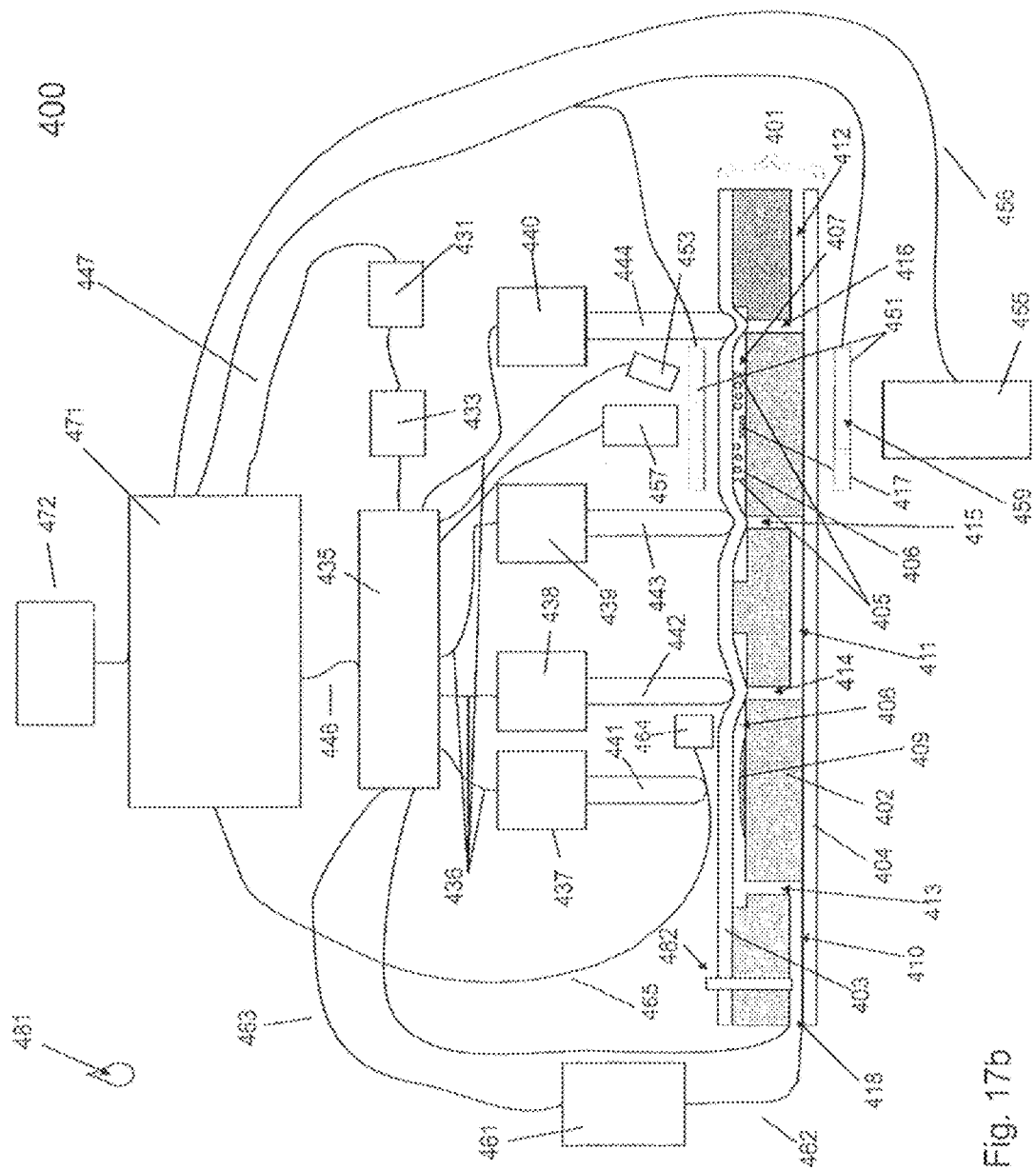
FIG. 17b illustrates the device performing at least the steps of capturing the targets from a sample, amplification of the target and detection of one or more values indicative of the presence of the target in the sample in operated state.

FIG. 17b. illustrates an exemplary system 400 for performing at least the steps of capturing targets from a sample, amplification of the target and detection of one or more values indicative of the presence of the target in the sample in operated state.

Figure 17C:
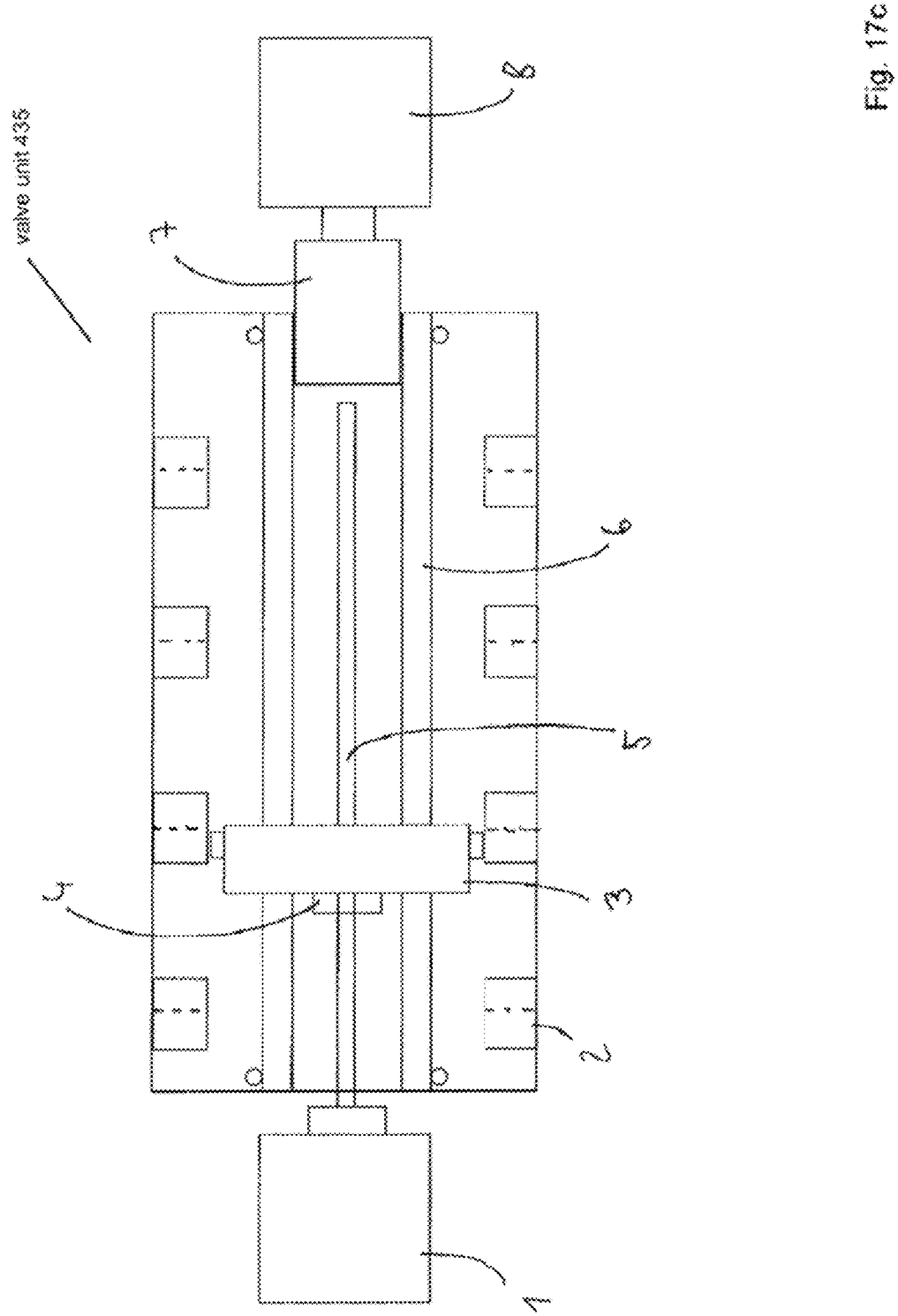
FIG. 17c illustrates the valve unit 435 depicted in FIGS. 17a and 17b.

FIG. 17c illustrates an exemplary embodiment for valve unit 435 depicted in FIGS. 17a and 17b.

Figure 17D:
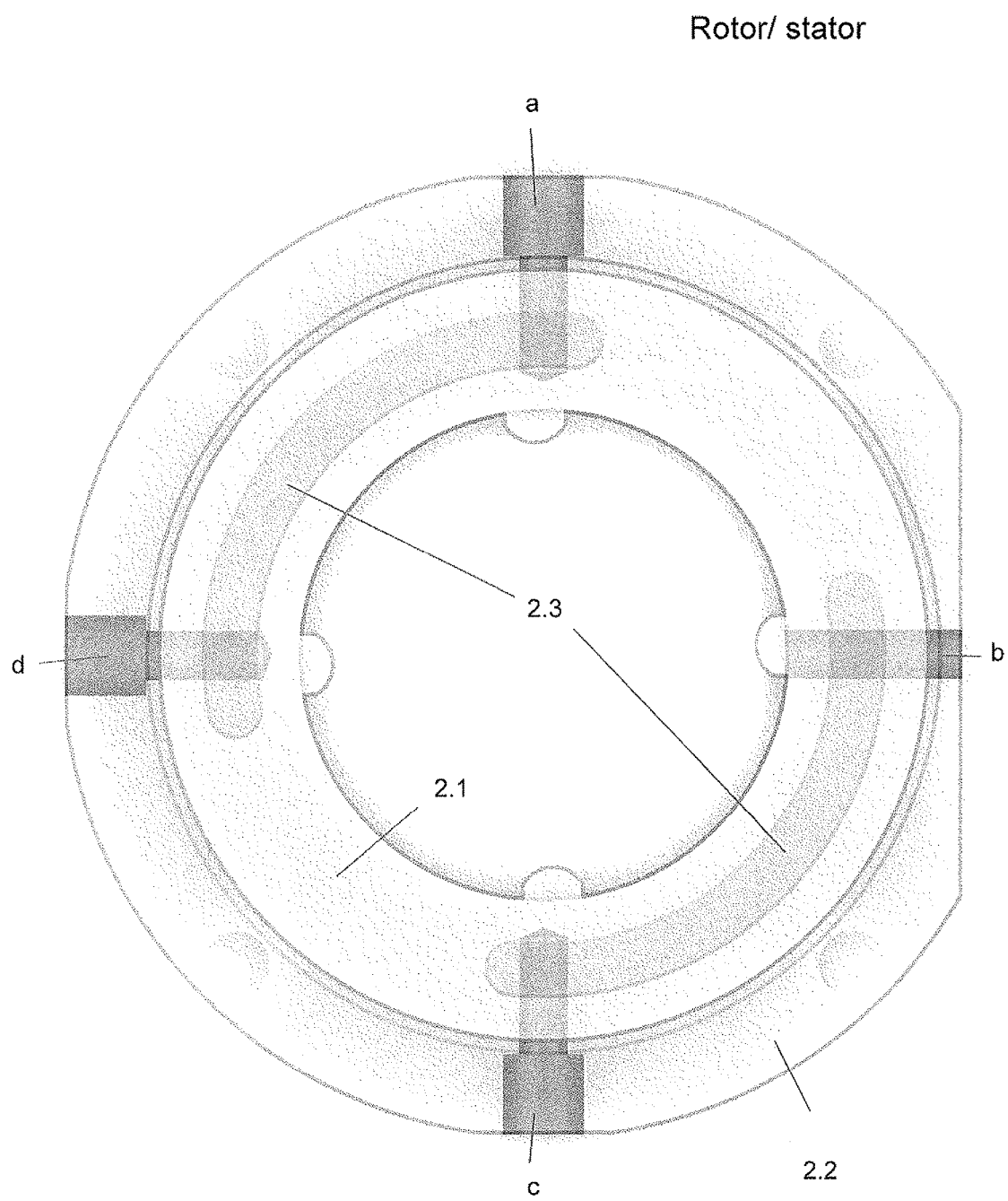
FIG. 17d illustrates the valve 2 depicted in FIG. 17c.

FIG. 17d illustrates an exemplary embodiment for valve 2 depicted in FIG. 17c.

Referring to FIGS. 17a and b, the exemplary system 400 comprises a microfluidic cartridge 401, a detection system 455, a system for heating and/or cooling at least a part of the cartridge 451, actuator members 441-444 and actuators 437-440, a valve unit 435, a compressor 431, a liquid reservoir 461 and a processor 471.

Cartridge 401 comprises a substrate 402 and a first cover element 403 which together define a first and a second well 408 and 407. The first cover element 403 is at least partially flexible to allow the cover element to be reversibly pressed towards substrate 402. The cartridge further comprises a second cover element which defines together with substrate 402 channels 410, 411, 412. In some embodiments, the second cover element is also at least partially flexible. Channels and wells are interconnected by holes 413, 414, 415, 416 to form a microfluidic network.

In various embodiments, the substrate 402 may be any physical body made of any suitable material, such as plastics, glass, metal or a semiconductor. It may be any essentially planar (i.e. two-dimensional) or non-planar (i.e. three-dimensional) surface. An example for such a three-dimensional object is a physical body having a cavity or well comprising a reaction chamber (in which a biological, chemical or biochemical reaction may occur) comprising fluidic paths (like channels).

The first well 408 which may also be denoted as a lysis well is adapted for accommodating fluids and for releasing contents of cells, spores, or viruses, the contents including target molecules to be analyzed by the system 400. E.g., the first well 408 is adapted for releasing contents of cells, spores, or viruses by comprising lysing reagents 409 as described above. The lysing reagents 409 may be provided in dried form.

A second well 407 which also may be denoted as a central well is adapted for accommodating fluids and comprises particles 406 as first binding members, the particles adapted for capturing target in complex with capture molecules and, optionally, a second binding member 417 adapted for capturing reporter molecules. The second well 407 further comprises filter elements 405 to prevent passage of particles 406 but to permit passage of gases, liquids and substances solved in the liquids.

Wells 407 and 408 are interconnected by channel 411 via through holes 415 and 414.

More generally, the first and second wells 408, 407 can be any structure, i.e. any physical entity which can serve as a carrier for receiving samples or substances. Particularly, such structures may include recesses such as grooves, wells or channels, or may also cover a material in which substances may be accommodated and through which the substances may be moved, such as gels.

In various embodiments, binding members comprise a component which is configured to bind molecules having a specific configuration. Such binding members may or may not be molecules immobilized on a surface. A binding capability may also result directly from a surface configuration (for instance a porous surface structure). It is also possible that binding members are provided as or on three-dimensional elements such as beads or a porous support. The surface of such a three-dimensional element or further molecules attached to the surface of the three-dimensional element, e.g. particles, may then serve as binding members. Different binding members being sensitive to different molecules may also be arranged (for instance in a matrix-like manner) on a surface of a structure. Examples for binding members are described above with respect to the various methods disclosed herein.

Volumes of the lysis well 408 and of the central well 407 may be 100 µl.

In an exemplary embodiment, the width of the channels 410-412 is 200 μm, and a height of the channels 410-412 is 100 μm.

In various embodiments, such a microfluidic network may comprise one or more channels and/or wells, which may be interconnected to one another. For example, the various channels of such a microfluidic network may be bifurcated or branched to thereby allow for a transport of liquids through the micro fluidic network along predefined paths (not shown).

The system 400 also comprises an actuator system comprising actuator members 441, 442, 443, 444 driven by pneumatic actuators 437, 438, 439, 440, a valve unit 435, a compressor 431 and a reservoir for compressed air 433.

Compressor 431 may constantly adjust a defined pressure in the reservoir for compressed air 433.

Each of the actuator members 441, 442, 443, 444 is actuated by a corresponding actuator. In use, cartridge 401 is positioned with the at least partially flexible cover element 403 facing the actuators and actuator members. Each actuator member corresponds spatially to a different location of microfluidic network of cartridge 401. For example, actuator member 442 corresponds to hole 414 leading to well 407 via channel 411 and hole 415. When actuated, actuator member 442 compresses the at least partially flexible cover 403 overlying hole 414 thereby obstructing hole 414 and preventing the passage of fluid there along. Other actuator members correspond similarly to other structures. E.g., actuator members 443 and 444 respectively correspond to holes 415 and 416. Actuation of actuator members 415, 416 seals second well 407 allowing e.g. multiple heating and cooling cycles to be performed without significant loss of liquid therein.

For exemplary actuation of actuator member 442 the control unit sends a signal to the valve unit. The valve unit opens the pneumatic connection 436 to actuator 438 thereby applying a pressure to the actuator 438. Thus, actuator member 442 moves out and compresses the at least partially flexible cover 403 overlying hole 414. To release the actuator member, the control unit sends a respective signal to the valve unit. The valve unit closes the pneumatic connection leading to actuator 438 thereby moving back the actuator member 442 and releasing the at least partially flexible cover 403 overlying hole 414.

The actuator member may be adapted to elastically deform the first flexible cover 403 to perform various tasks. E.g., as described above actuator member 442 is adapted to compress the at least partially flexible cover 403 overlying hole 414 thereby obstructing hole 414 and preventing the passage of fluid there along while actuator member 441 is adapted to move a liquid within well 408 by repeatedly pressing and releasing the first flexible cover overlying well 408.

In one embodiment, an actuator member may be an element which is able to be moved to selectively open or close individual ones of the structures of the microfluidic network by mechanical forces. For example, such an actuator member may be a pin or a stencil which may be pressed against a flexible cover element to press the latter onto a surface of the substrate, thereby selectively opening or closing the channels.

In some embodiments, the tip of the actuator member 441, 442, 443, 444 is made of an elastic material such as silicone, gum or the like. The diameter of the actuator members 442, 443 and 444 maybe 1.5 times the diameter of holes 414, 415 and 416. A typical diameter for holes 414, 415 and 416 is 0.5 mm.

As described above, a pneumatic valve unit 435 is provided which is coupled to the actuators 437-440. The valve unit 435 receives drives signals from a control unit 471. Thus, the control unit 471 controls the operation of the actuator members 441-444.

The control unit 471 such as a microprocessor is provided and adapted for controlling an analysis of a fluidic sample in such a manner that target molecules of the fluidic samples are captured at the binding members 406. The control unit 471 further controls an amplification of the target molecules in the central well 407.

Moreover, the control unit 471 controls a detection of compounds indicative for the presence and/or amount of the target molecules and captured at the binding members 417. All solid phase coupling procedures during an analysis of the target molecules occur at the binding members 406 in the central well 407. Particularly, no solid phase coupling procedures occur in the lysis well 408.

In an embodiment, a control unit may be an electronic component which is capable of controlling the function of one or more other components of the device, and which may particularly coordinate the function of the individual components. In the control unit, a code or an algorithm may be stored or may be user-defined in software, in hardware, or in hybrid form (i.e. comprising software and hardware components), in a manner to be capable of performing a specific analysis, experiment or assay. Particularly, such a control unit may include a processor having processing capability (optionally having also storage capability) and being configured to perform a specific experimental protocol. Particularly, such a control unit may be a microprocessor or a CPU (central processing unit).

The temperature of fluids in the central well 407 can be manipulated by a temperature manipulation unit comprising an pneumatic cooler 453, a temperature sensor (not shown) and a heating and/or cooling plate 451 arranged in vicinity of an upper surface of the substrate 402 and a second annular heating and/or cooling plate 451 having a central recess 459 to allow for an optical detection of molecules in the central well 407. In some embodiments, the heating and/or cooling plates comprise a temperature sensor for adjusting the temperature of the heating plates and/or of the second well. The control unit 471 may control the temperature distribution of the plates 451 to thereby manipulate the temperature of liquids in the central structure 407 (for instance in accordance with a temperature sequence for performing a polymerase chain reaction, to amplify target molecules during the analysis).

Particularly, the temperature manipulation unit 451 has the capability to raise the temperature of the liquids located in the central well 407 up to 95° C.

The heating/cooling elements or plates 451 may be flexibly mounted. The flexible mounting may be a flexible mounting of the whole heating/cooling element. A frame supporting the heating/cooling element 451 may be for example hinged to a carrier structure, so that the hinge allows the flexible position of the whole heating/cooling element 451.

Alternatively or in addition, the flexibly mounting may also be a flexibility of the heating/cooling element 451 as such. This can for example be achieved by a flexible layer, which layer comprises the heating/cooling source/drain. Any kind of actuator may be provided behind the flexible layer to actuate the heating/cooling element layer. Such an actuator may for example be an inflatable air pillow. However, the flexible layer may also be provided with a resilient member on the back side allowing a flexible matching when being pressed against the structure.

Thus, by flexibly mounting at least one of the heating/cooling elements, an efficient thermo transition can be carried out, since the flexible heating/cooling element 451 can be flexibly adapted to the structure or the probe device.

The heating/cooling element 451 may be a combined flexible whole heating/cooling element 451 and flexible as such heating/cooling element 451.

As a matter of fact, also two heating/cooling elements 451 may be flexibly mounted. The both heating/cooling elements may be arranged in a butterfly fashion to sandwich the probe device. In the same fashion a single heating/cooling element 451 may be arranged with a pressing counter plate. This may avoid any scratches when inserting the probe device, in particular when the heating/cooling elements 451 will be moved towards the surfaces of the probe device after the probe device has reached its final position.

Between the substrate 402 and the cover element 404, a fluid interface 418 is provided allowing inserting liquids such as water or buffers or gases such as air into the microfluidic system via channel 410 and hole 413. Another interface 482 may be provided which allows inserting a sample 481 into the micro fluidic system.

In some embodiments, the substrate 402 is, at least partially, optically transparent to thereby allow for an optical radiation based detection of the components in the central well 407, as will be explained in the following.

A detector system 455 comprising an optical light source (not shown) such as a laser diode is adapted for generating an electromagnetic radiation beam impinging through the recess 459 in the second heating element 451 into the central chamber 407. In the presence of fluorescence markers in this chamber 407, a secondary electromagnetic light beam is generated which may propagate through the recess 459 in the second heating element 451 and may be detected by a detector (not shown) in the detector system 455 such as a photodiode. A detection signal of the detector system 455 indicative for the concentration of the target molecules may be provided to the control unit 471 for further processing via control unit interface 456. Thus, as can be taken from FIG. 17, the control unit 471 also coordinates the function of the detector system 455.

In some embodiments, during detection a detection actuator 457 compresses the central well to reduce the distance between the flexible cover elements 403 and 404 or between the flexible cover elements 403 and 404 and the substrate 402 thereby removing liquid comprising material which has not bound to one of the binding members 406 or 417 from the detection zone.

A liquid supply 461 is provided for pumping liquids such as water or buffers through the microfluidic network formed by the wells 408, 407, by the through holes 413, 414, 415, 416 and by the channels 410, 411, 412.

The transport of liquids through the device 400 may also be performed by sucking the liquid by a negative pressure (not shown).

An optical sensor 464 may provided to control the fluid level in chamber 408 as exemplary explained in the following. If well 408 is to be filled with liquid from liquid supply 461 the control unit 471 sends an according signal to valve unit 435 via interface 446. The valve unit opens a valve to apply pressure on liquid supply 461 via pneumatic connection 463 thereby pressing liquid from the liquid supply 461 into well 408 via liquid connection 462, channel 410 and hole 413.

When optical sensor 464 detects a signal indicative for the presence of the liquid in well 408, the sensor sends a signal to the control unit 471 via interface 465. The control unit 471 then sends a signal to valve unit 435. The valve unit closes the valve thereby stopping the pressure on liquid supply 461 thereby stopping the movement of the liquid out of well 408.

Other optical sensors may be provided to control the liquid levels in other structures such as channels (410, 411, 412, sensors not shown) or wells (407, sensors not shown).

In various embodiments, the sample 481 may comprise any solid, liquid or gaseous substance, or a combination thereof. For instance, the substance may be a liquid or suspension, furthermore particularly a biological substance (such as blood, particularly whole blood). Such a substance may comprise proteins, polypeptides, nucleic acids, lipids, carbohydrates, viruses, bacteria, etc. In embodiments, a sample is a composition of matter possibly comprising a target.

As can be taken from FIG. 17, the control unit 471 also controls the pump 431 via interface 447. A reservoir 433 for compressed air may be provided so as to harmonize the pumping procedure with the performance of the actuators 437-440, of the pneumatic cooler 453 and with the detection actuator 457.

The system 400 further comprises a user interface unit 472 which may also be denoted as an input/output device. Via the user interface unit 472, a user may define an experiment run by the system 400. In other words, the user interface 472 may enable a user to program the system 400 so as to perform a specific assay. Such a user interface 472 may comprise a graphical user interface (GUI) having a display unit such as an LCD, a plasma device, or a cathode ray tube. Furthermore, input elements can be provided at the user interface 472 such as a keypad, joystick, buttons, a trackball or even a microphone of a voice recognition system. The user interface 472 is connected to the control unit via a data connection.

Referring to FIGS. 17*c* and *d*, in some embodiments the valve unit 435 consists of a number (n) of single valves (2). Each valve is made of a rotor (2.1) comprising channels (2.3) and a stator (2.2) both consecutive mounted and fixed with 4 springs to apply a constant pressure. Each valve has 4 holes (a, b, c, d), a is connected with the ventilation, b) is connected to the compressor, c) is connected with the pneumatic actuator and d) is connected to the ventilation site of the actuator The carrier (3) connected to a ball screw (4) that is placed inside the tube. A slot within the tube (6) enables the carrier to move. Rotation movement of the driving shaft (5) will result in a movement of the ball screw and the connected carrier in x-direction. That enables a movement of the carrier to the position of each valve (2). The carrier will lock into the rotor (2.1).

A 90° movement of the tube (6) will result in a 90° movement of the carrier (3) and rotor (2.1). The rotor and the pockets in the rotor disc will open or close the valve connections. (a,b and c,d; d,a and b,c).

In the following, referring to FIG. 18 and FIG. 19, a device 500 according to another exemplary embodiment will be explained.

FIG. 18 shows a front view and FIG. 19 shows a back view of the device 500.

The device 500 comprises a groove 501, formed in a substrate 402, for inserting a cannula (not shown) via which a sample may be supplied to the device 500. A lysis chamber 502 is provided in which materials needed for lysing may be stored in a dried form. A central well 512 serves for performing all solid phase coupling procedures required for operating the device 500. Additional wells 504, 506, 508, and 510 are provided in which various further substances are provided in dried form and which may serve for washing procedures, a PCR procedure, etc. A waste chamber 514 is provided as a well in which liquids can be transported which are no longer needed for the analysis.

Although not shown in FIG. 18 and FIG. 19, a liquid absorbent material may be provided in the waste chamber 514 which can absorb fluids entering the waste chamber 514. By taking this measure, undesired back flow of liquids from the waste chamber 514 into other portions of the device 500 may be securely prevented to thereby avoid any contamination. For instance, swellable polymers (which may also be used in diapers) may be employed for such a purpose.

As can be taken particularly from FIG. 18, a plurality of fluid connection ports 520, 524, 521, 525, 540, 542, 544, 545, 548, 578, 580, 558, 562, 564, 560, 561, 552, 550, 516, 554, 530, 528, 532 and 526 are provided connecting various ones of channels, which will be explained in the following.

As can be taken from FIG. 19, additional fluid connection ports 541, 560, 566, 519, are shown. Furthermore, a plurality of channels 538, 522, 518, 527, 529, 536 572, 574, 576, 539, 562, 570, 546, 556, 568 and 534 are foreseen to connect the various fluid connection ports 520, 524, 521, 525, 540, 542, 544, 545, 548, 578, 580, 558, 562, 564, 560, 561, 552, 550, 516, 554, 530, 528, 532, 526, 541, 560, 566, 519 and wells 502, 504, 506, 508, 510 and 512. Beyond this, a fluid inlet port 593 is shown via which fluids such as water may be injected into the device 500. Via a fluid outlet port 594, fluid (such as air removed for reducing a pressure) may be removed from the device 500. A further fluid inlet/outlet port 597 is shown as well.

A first window portion 598 accessible by a light barrier and a second window portion 599 accessible by a light barrier are shown which may serve to detect optically when a meniscus of a fluid column within the device 500 passes transparent window portions 598, 599 related to the light barriers. When one of the light barriers detects that one of the chambers corresponding to the window portions 598, 599 is full with a liquid or overflows, this may be detected optically and may serve to generate a control signal for controlling a control unit (not shown in FIG. 18 and FIG. 19) to control the operation of the device 500 correspondingly.

When a first portion of a cannula is inserted into the groove 501, a second portion of the cannula may be inserted into a patient to take a blood sample from the patient and to directly inject the whole blood sample into the device 500.

Although not shown in FIG. 18 and FIG. 19, any one of the fluid connection ports 520, 524, 521, 525, 540, 542, 544, 545, 548, 578, 580, 558, 562, 564, 560, 561, 552, 550, 516, 554, 530, 528, 532, 526, 541, 560, 566, 519 may be covered by a flexible member which may be compressed by an actuator pin (not shown in FIG. 18 and FIG. 19) so that the pins may serve for selectively opening or closing any individual one of the fluid connection ports 520, 524, 521, 525, 540, 542, 544, 545, 548, 578, 580, 558, 562, 564, 560, 561, 552, 550, 516, 554, 530, 528, 532, 526, 541, 560, 566, 519, thus fulfilling a valve function.

Although not shown in FIG. 18 and FIG. 19, any one of the wells 502, 504, 506, 508, 510 and 512 may be covered by a flexible member which may be compressed by an actuator pin (not shown in FIG. 18 and FIG. 19) so that the pins may serve for selectively pressing on the wells 502, 504, 506, 508, 510 and 512, thus serving as mixers or pumps.

As can be taken from FIG. 18, a component 587 forming the central well 512 is a moulded plastic member which can be inserted into grooves 585, 583 of the substrate 402. This plastic member 587 may be patterned or structured from both sides so that components 590, 591, 578, 548, 580, 558, etc. are formed.

In the following, an assay performed in the device 500, particularly based on the central well 512, will be explained which may allow to perform a determination of HIV load in a fast manner, for instance in less than one hour.

Within the central chamber 512, beads may be provided. These beads may be configured to capture target molecules (for instance HIV RNA) from a previously lysed sample. E.g., the beads may be configured to bind an anchor group of a capture molecule to bind complexes comprising a target polynucleotide and the capture molecule, wherein the capture molecule comprises a binding portion specific to a region of the target polynucleotide and the anchor group.

Reference numeral 541 denotes a connection to pressurized air (see arrow in FIG. 19) so that pressurized air may pass through elements 538, 518, 516 and will enter the well 502. Thus, it is possible to pump the well 502 empty using pressurized air. In case that a blood sample supplied via the groove 501 should be diluted with water, such water may be supplied via fluid inlet port 593.

In one embodiment, a whole blood sample (or any other sample) may be transported in the well 502, for instance for lysing. Blood may be soaked into the device 500 by first compressing the chamber, applying the blood to a capillary, the capillary in contact with the lysing chamber 502, then releasing the lysing chamber 502 thereby soaking the blood into the device 500.

For this purpose, the corresponding lysing agents as described above are provided in dried form in the lysis well 502. The lysis well may further comprise the capture molecules each comprising an anchor group and a binding portion specific to a region of the target polynucleotide. The sample which now may comprise complexes each comprising a target polynucleotide and a capture molecule may then be transported via components 554, 556 (via pressurized air) to the component 558. In this scenario, component 552 is closed by a corresponding actuator. Via components 558, 580, the sample may be transported into the central well 512. For this purpose, grooves 591, 590 of the central well 512 may be equipped with filters such as frits (not shown in FIG. 18 and FIG. 19) preventing beads in the central well 502 from being removed from this well 502 under the influence of the streaming force of the fluids. Thus, via the filter or frit in the grooves 591, 590, the lysed sample may be transported via component 576 into the central well 512.

In the central well 512, a first binding member such as beads or a surface functionalization may be provided so that targets or complexes comprising a target polynucleotide and a capture molecule may bind on solid capture structures in the central chamber 512. An incubation may be performed so that the beads properly mix with the sample material.

An air stream presses the liquid (i.e. non-captured components of the lysed sample) from the central well 512 via components 558, 560, 561 into the waste 514. Thus, many of the sample components which have not been captured by the beads in the central well 512 are transported into the waste chamber 514. Thus, only targets remain in the central well 512, and the remainder of the whole blood sample is now in the waste 514. Thus, the central well 512 now houses the beads together with complexes comprising capture probes and targets.

Subsequently, the central well 512 may be washed, wherein components for a wash buffer provided in a solid manner in a wash well 504 are used to produce a wash buffer. Such a washing procedure may be advantageous since, after the capturing procedure, some impurities may still be present in the chamber 502, particularly when a whole blood sample is used or the sample is supplied via a cannula inserted into the groove 501.

The wash liquid may be pumped, under the influence of air pressure, via components 541, 540, 542, 546, 548, 578, 591, 574, 512.

As already indicated above, a wash buffer is prepared in the wash well 504. In the wash well 504, salts for such a wash buffer may be present in dried form. For preparing the wash buffer, water may be transported from component 566 via components 564, 562, 570, 552 (while component 554 is closed), 527 (components 532, 525, 530 are closed), so that water is supplied to component 521 (open). Water may be pumped in the wash well 504 until a transparent window coupled to component 520 is filled with water, which may be detected by detecting a meniscus passing the light barrier adjacent the transparent window next to component 520. Upon receipt of a corresponding detection signal, the supply of water may be terminated.

An actuator (not shown) may then reciprocate upwardly and downwardly to compress a flexible cover element covering the wash well 504 to perform mixing to dissolve the salts provided therein.

Water filled channels may then be emptied by a corresponding control of the various valves and by supplying pressurized air, so that the water may be pumped into the waste chamber 514.

The prepared wash buffer in the wash well 504 may then be pressed into the central well 512 so that a washing procedure may be performed in the central well 512. After this washing, the wash solution may be pumped in the waste chamber 514. Next, a reverse transcription may be performed to convert target RNA into a corresponding DNA. Such a procedure is specifically necessary in case of detecting Retroviridae such as HIV, and may be dispensable in other cases, for instance when DNA viruses are detected. To perform such a reverse transcription, components required for reverse transcription such as a primer, an enzyme and a buffer may be pumped from a reverse transcription well 508 into the central well 512.

Optionally, the components in the reverse transcription well 508 may also comprise another set of further capture molecules which may have the specific capability of capturing DNA molecules in the central well 512 produced during reverse transcription.

Since, after the reverse transcription, target DNA does not remain at the beads of the chamber 512, transporting the solution into the waste container 514 would reduce the amount of sample. For this purpose, the sample is now pumped from the central well 512 into the PCR well 510, and may dissolve the PCR salts within this sample, wherein the PCR buffer in the PCR well 510 may comprise polymerase, reporter molecules capable of forming complexes with the target polynucleotide, primer, and/or buffer. Alternatively, the reverse transcription buffer contains capture molecules directed to the synthesised DNA strands and capturing these strands takes place the same way like the initial capturing of HIV nucleic acids. After this, the sample may be pumped back into the central well 512.

However, the actual PCR amplification is then performed in the central well 512. For this purpose, a PCR is performed in the central well 512 by performing a temperature cycle, that is to say by repeating e.g. 40 times a procedure with 5 s at 95° C. and 10 s at 60° C. In another embodiment a temperature cycle comprising 3 or more different temperatures, e.g. comprising 30 cycles of 20 s at 95° C., 30 s at 55° C. and 30 s at 72° C., can be performed. However, other PCR cycling protocols can be performed in the central chamber, too.

In some embodiments, for adjusting the temperature in the central well 512 two heating and/or cooling plates may be provided above and below the central well 512. In another embodiment, one of the two heating and/or cooling wells or plates may be continuous and the other one may have a recess to allow for a subsequent optical detection.

In some embodiments, the volume of the sample pumped from the PCR well 510 into the central well 512 may be such that the pressure in the central well is increased. This pressure increase forces the flexible cover elements of the central well against the two heating and/or cooling plates allowing, amongst others, for an efficient thermal transfer between the heating/cooling plates and the central well.

In some embodiments, during the amplification the detection may take place as described above.

E.g., in a first embodiment, a competitive assay of capture molecules may be performed in the central well 512. Thus, in this embodiment, a first binding member such as beads are used for capturing the complexes each comprising a target molecule and a capture molecule, and a second binding member comprising an array of reporter specific capture molecules immobilized in the central well 512 is used for detection. The competitive assay comprises forming complexes of a subset of the amount of reporter compound with at least a subset of the amount of target nucleic acid, the forming of these complexes inhibiting the capturing of the reporter compound by the array of reporter specific capture molecules immobilized in the central well 512. The reporter specific capture molecules immobilized in the central well 512 are capable of capturing at least a remaining subset of the amount of reporter compound not in complex with a target polynucleotide. By providing an array of different kinds of reporter specific capture molecules in the well 512 for detection, it is possible to distinguish between different types of the HI virus, for instance type 1 HIV and type 2 HIV, and it may be even possible to distinguish between different subtypes of the HI virus.

In a second embodiment, it is possible to use the same binding member, e.g. beads, which have already been used for the capturing procedure also for the detection. In this embodiment, a capture oligonucleotide being attached to the beads via an anchor group may hybridize with a complex of amplified target DNA, which itself may comprise a fluorescence label.

The captured reporter compounds or the captured target molecules may be detected by an optical detection for instance using the fluorescence label as described above. Particularly, an optical system having a light source (not shown) and a light detector (not shown) may be operated in a manner so as to measure the time dependence of the signal during the PCR, which allows deriving the viral load of HIV. In other words, the time dependence of the fluorescence signal may be acquired and evaluated.

In the following, referring to FIG. 20, a device 600 according to an exemplary embodiment will be explained.

Figure 20:
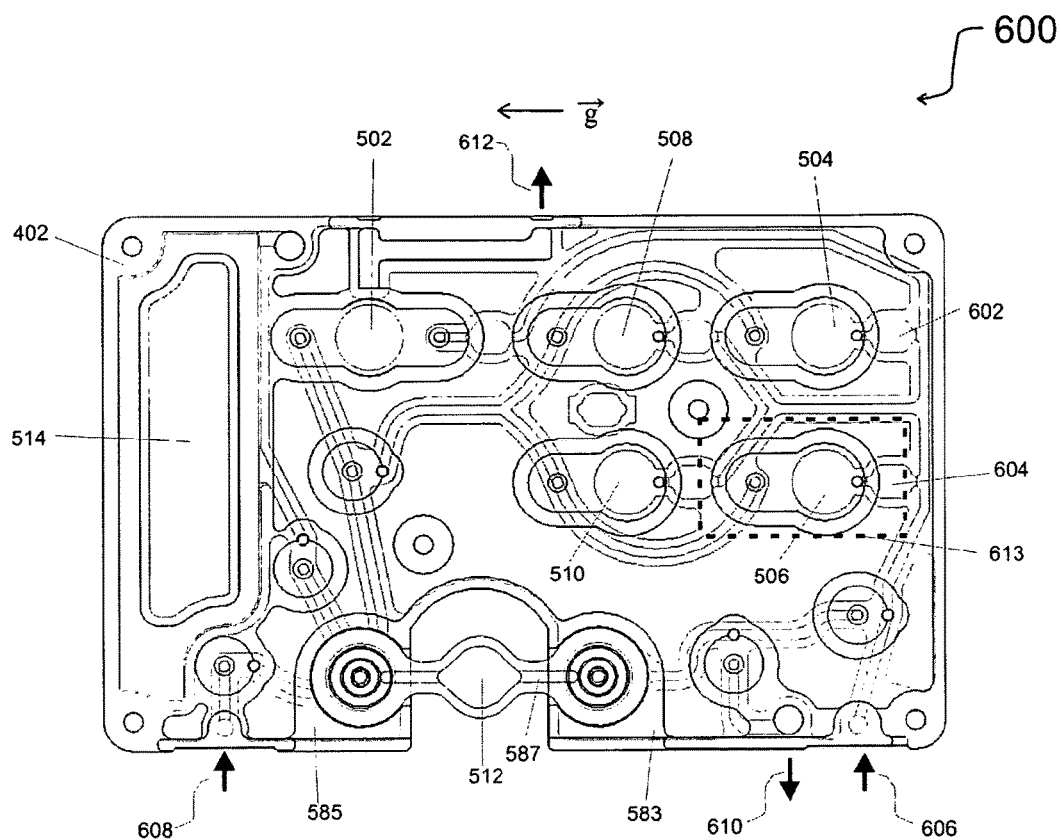
FIG. 20 illustrates a plan view of a device according to an exemplary embodiment.

The embodiment of FIG. 20 is similar to the embodiments of FIGS. 18, 19, so that corresponding components are denoted with the same reference numerals. For the sake of simplicity and clarity, the channels and fluid ports are not denoted with reference numerals in FIG. 20. For corresponding explanation, reference is made to FIG. 18 and FIG. 19.

FIG. 20 shows a window portion 602 related to the well 504 and a window portion 604 related to the well 506 to enable for a meniscus detection and therefore an overflow detection as a basis for determining control signals for controlling actuators acting on the wells 504, 506 and acting on the various fluid communication ports.

The direction of the gravity vector $\vec{g}$ is indicated to show in which position the device 600 can be operated in some embodiments. In these embodiments, the operation of the device 600 is based on a combination of the gravitational force and liquid transportation forces provided via a pressure air connection 606, and a water supply connection 608. Furthermore, a vent connection 610 and a vent connection 612 are provided for venting the corresponding fluidic structures.

FIG. 20 schematically shows a portion 613 which can be, as an alternative to the integral solution of FIG. 20, be provided as a separate module which can be combined with other modules to form a user-defined device in which the various modules are assembled together.

In the following, referring to FIG. 21, a device 700 according to another exemplary embodiment will be explained.

The device 700 comprises a rigid substrate 704 in which a first through hole 709 and a second through hole 707 are formed. On a first main surface of the substrate 704, a first well 720 and a second well 708 are formed. On an opposing main surface of the substrate 704, a channel 706 is formed. The channel 706 is in fluid communication with the wells 720, 708 via the through holes 709, 707, respectively.

On an upper surface of the rigid substrate 704, a first flexible cover element is formed and adhered to the rigid substrate 704. On a lower surface of the substrate 704, a second cover element 705 is formed and laminated to the rigid substrate 704.

Figure 21:
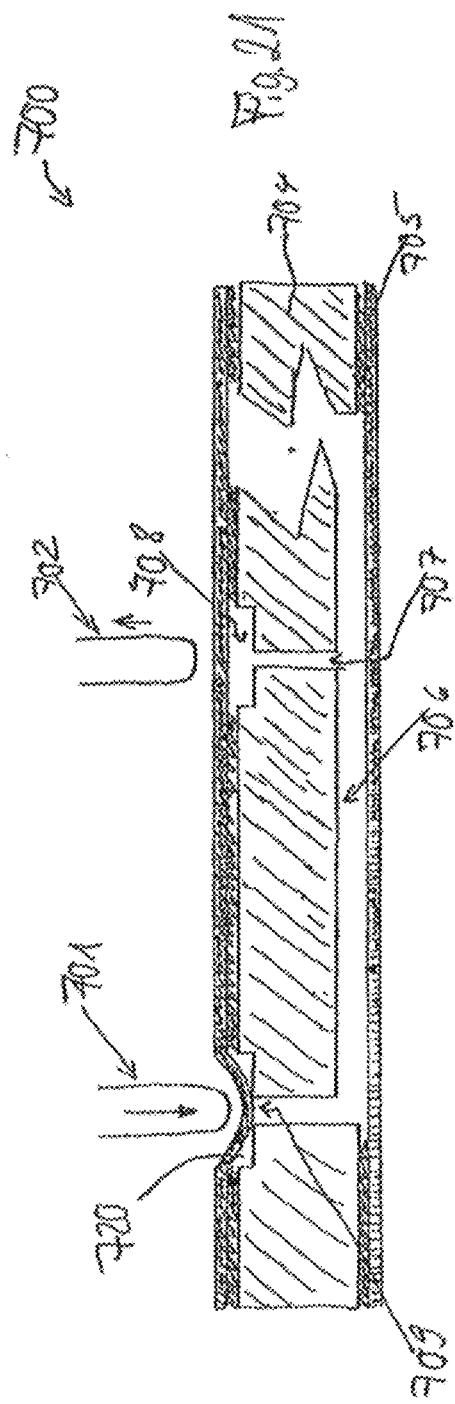
FIG. 21 illustrates a cross-sectional view of a device according to an exemplary embodiment.

As can further be taken from FIG. 21, a first actuator member 701 and a second actuator member 702 are provided, the first actuator member 701 being adapted for pressing on a first portion of the cover element 720 to selectively close the through hole channel 709 or the entire well 720. In a corresponding manner, the second actuator element 702 may selectively open or close the well 708 and/or the through hole 707. Thus, the flow of a fluid through channel 706 into one or both of the wells 720 or 708 can be controlled.

Figure 22:
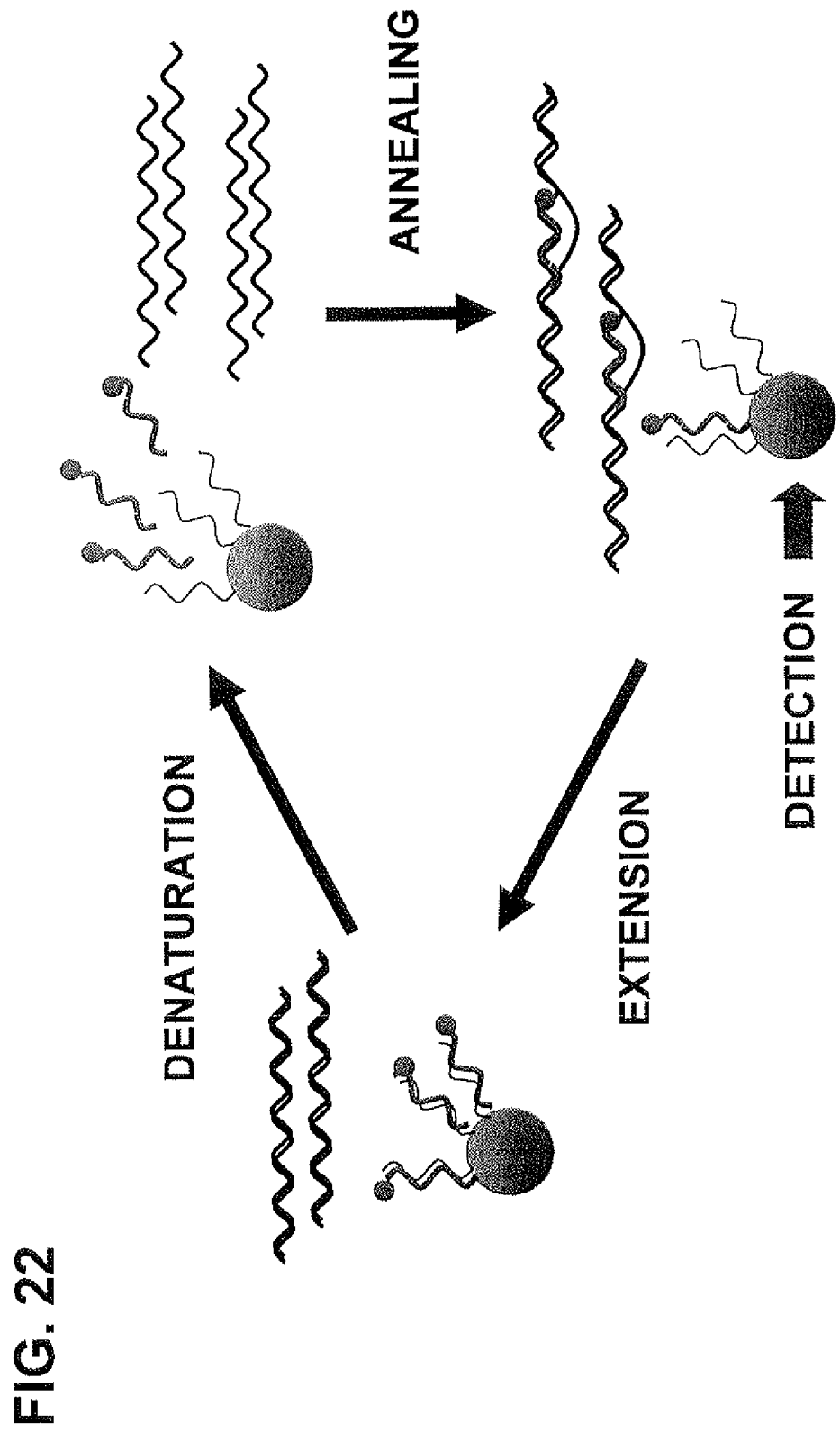
FIG. 22 schematically illustrates an exemplary embodiment of the competitive method for the detection of polynucleotides according to the present invention.

FIG. 22 represents a schematic illustration of an exemplary competitive assay according to the present invention. A labelled nucleic acid reporter molecule (shown as a grey sinuous line) is attached via a nucleic acid capture molecule (shown as a black sinuous line) on a binding member (here exemplified as a bead). The target nucleic acid to be detected is present in the sample in double-stranded form (the two strands are shown as light grey/black sinuous lines). Subjecting the sample to a denaturation step (of a cyclic amplification reaction) allows the strands of the target nucleic acid to dissociate and the reporter molecule to be released from the binding member. During the subsequent annealing step, a subset of the amount of reporter molecule is allowed to form complexes with at least a subset of the amount of the target nucleic acid, wherein the forming of target nucleic acid/reporter molecule complexes inhibits the capability of the reporter molecule of being captured on the binding member due to a competition of the capture molecule and the nucleic acid target for binding the reporter molecule. The remaining subset of the amount of reporter compound not in complex with a target nucleic acid is allowed to be re-captured on the binding member. At this stage, a value indicative for the presence and/or amount of reporter compound captured on the binding member, and based thereon a value indicative for the presence and/or amount of the target nucleic acid, is determined by detecting a signal generated by the label comprised in the receptor molecule. Consecutively or concomitantly to the annealing step, the extension step of the amplification reaction is performed. Then, the sample may be subjected to another amplification cycle.

Figure 23:
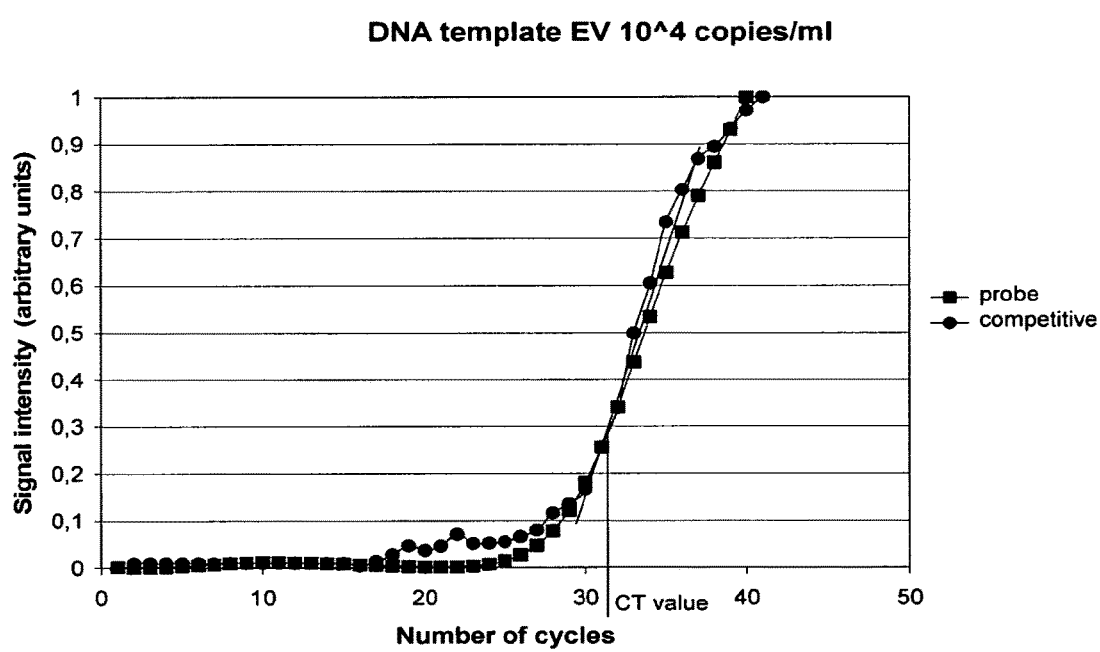
FIG. 23 shows the results of an exemplary embodiment of the competitive assay according to the present invention for determining the amount of human poliovirus 1 DNA in a sample.

FIG. 23 shows the results of an exemplary competitive assay according to the present invention for determining the amount of human poliovirus 1 DNA (designated "EV" for "enterovirus DNA") in a sample in comparison to a standard Taq-man assays performed with the same target. Two samples, each containing $10^4$ DNA copies were analyzed in parallel: the first sample (label "probe" in the diagram) was subjected to PCR amplification using a Rotor-Gene 6000 real-time rotary PCR analyzer (Corbett Life Sciences, Sydney, Australia) according to the manufactures instructions. The PCR primer employed resulted in the amplification of a 150 bp DNA fragment. Detection of the fragment was accomplished by means of a so-called Taqman® probe comprising a 6-carboxy-fluorescein (FAM) label at its 5' terminus and a 6-carboxytetramethylrhodamine-succinimidylester (TAMRA) label at its 3' terminus, respectively (Invitrogen Corporation, Carlsbad, Calif., USA). In total, 50 PCR cycles were performed. The second sample ("competitive assay") additionally included a reporter molecule having the same nucleotide sequence as the Taqman® probe but comprises a CY3 carbocyanine label (Invitrogen Corporation, Carlsbad, Calif., USA) at its 3' terminus instead of FAM/TAMRA labels and was amplified using a device according to one embodiment of the present invention. The fluorescence signals obtained detected during amplification are shown in the diagram.

FIG. 24 illustrates the principle and shows the results of an exemplary array-based competitive assay according to the present invention for determining the amount of a HIV gag/env PCR product in a sample. FIG. 24A schematically illustrates the principle of the assay (cf. also FIG. 22). Initially, no amplified PCR product, i.e. target nucleic acid is present. Labelled fluorescent nucleic acid reporter molecules are bound to reporter-specific probes captured on the substrate of an array. If no PCR product is produced, the amount of reporter molecule hybridizing to the reporter-specific probes remains constant after each cycle of the amplification reaction and thus the fluorescence signal determined remains constant as well. If a PCR product is synthesized, the amount of reporter molecule hybridizing to the reporter-specific probes decreases after each PCR cycle and, as a result, the fluorescence signal determined decreases accordingly. FIG. 24B shows the results of an array-based competitive assay for determining the amount of a 151 bp HIV1 gag/env PCR product. Different amounts of fragment (corresponding to $10^4$-$10^6$ copies) along with a reporter molecule ("anti_cdso29_5'CY3") comprising at its 5' terminus a CY3 carbocyanine label (Invitrogen Corporation, Carlsbad, Calif., USA) were subjected to 36 cycles of PCR amplification. Two different types of probe molecules—a non-specific one ("ara_54986_NH2") and a reporter-specific one ("cdso29_NH2")—were captured on an array substrate in an arrangement as shown in FIG. 25A and disposed within the reaction chamber of the assay device employed. The CT values ("threshold"; i.e. a measure for the onset of the exponential amplification phase, where the increase in fluorescence and thus DNA amount occurs in a linear manner) were determined using the Iconoclust software (Clondiag Chip Technologies GmbH, Jena, Germany) and plotted versus the respective DNA concentrations employed to generate a calibration curve (FIG. 24C). In all samples employing the receptor-specific probe a progressive decrease in fluorescence intensity was observed as the number of PCR cycles increased. In contrast, in the sample using the non-specific probe no fluorescence was observed (FIG. 24B).

FIG. 25 depicts the array employed in the assay shown in FIG. 24 at different stages of the PCR amplification. The arrangement of the different spots on the array substrate is schematically illustrated in FIG. 25A. The black circles denote spots (four parallel samples), where the specific probe (cf. FIG. 24) was used for capturing the reporter molecules, whereas the white circles refer to spots (four parallel samples), where the non-specific probe was used for capturing the reporter molecules. The grey circles represent positive controls, where the fluorescent label was spotted on the array substrate. FIG. 25B shows photographs of the array (corresponding to the $10^5$ DNA copies-samples in FIG. 24B) that were taken after amplification cycles 1, 12, 18, and 21, respectively. In the samples captured on the array via the specific probe molecules a decrease in fluorescence signal intensity can be observed during the course of the PCR amplification.

Figure 26A:
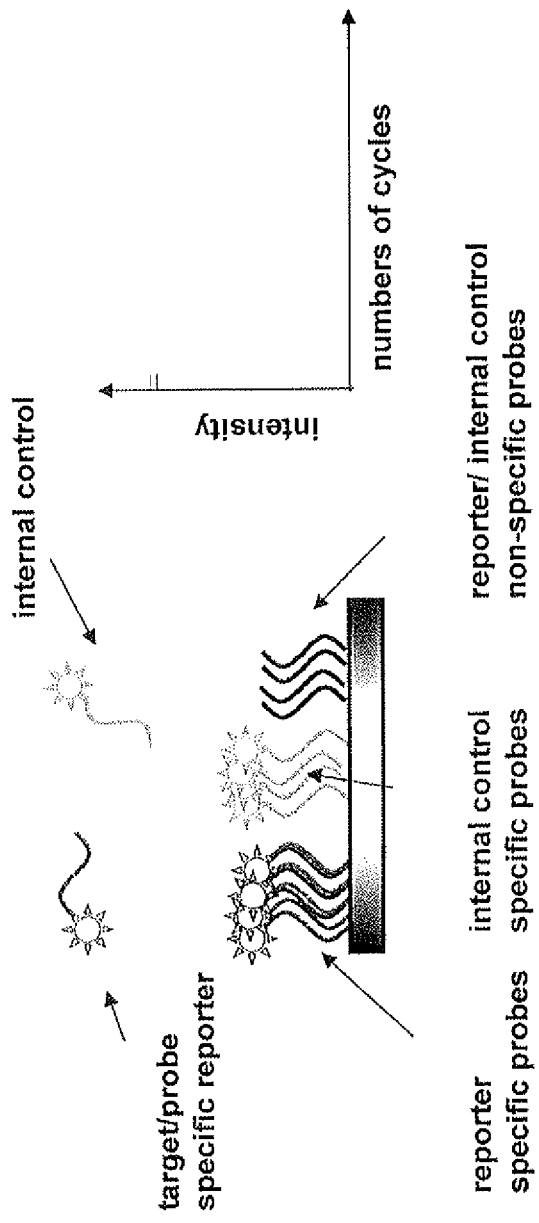
FIG. 26A shows no amplified PCR product.

FIGS. 26A-D represent a schematic illustration of an exemplary embodiment of the competitive method for the detection of polynucleotides according to the present invention. As shown in FIG. 26A, initially, no amplified PCR product, i.e. target nucleic, acid is present. Labelled nucleic acid reporter molecules (shown as a black sinuous line and denoted as target/probe specific reporter) are bound to reporter-specific probes captured on the substrate of an array. The signal corresponds to that of labelled internal control molecules (shown as light grey sinuous line) which are bound to internal control-specific probes captured on the substrate of an array. As shown in FIG. 26B, if the PCR enters into the early exponential phase the reporter molecules not only bind to reporter-specific probes captured on the substrate but also bind to the reporter-specific region of the PCR product. Thus, if a PCR product is synthesized, the amount of reporter molecule hybridizing to the reporter-specific probes captured on the substrate decreases and, as a result, the signal determined decreases accordingly. The signal decreases significantly when the PCR is in the exponential phase (see FIG. 26C). The signal on the reporter-specific probes captured on the substrate remains low when the PCR reaches the plateau phase (see FIG. 26D).

Figure 26:
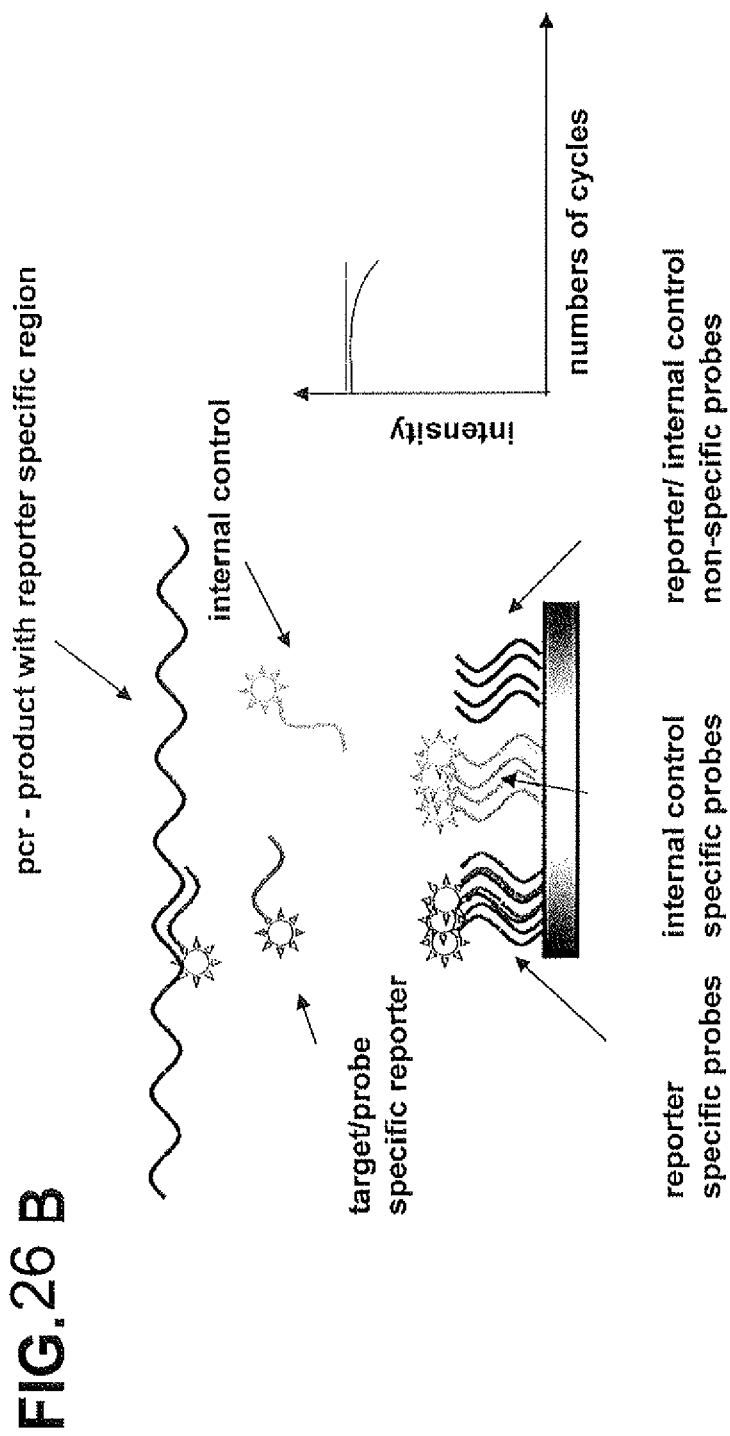
FIG. 26 schematically illustrates an exemplary embodiment of the competitive method for the detection of polynucleotides according to the present invention.
Figure 26:
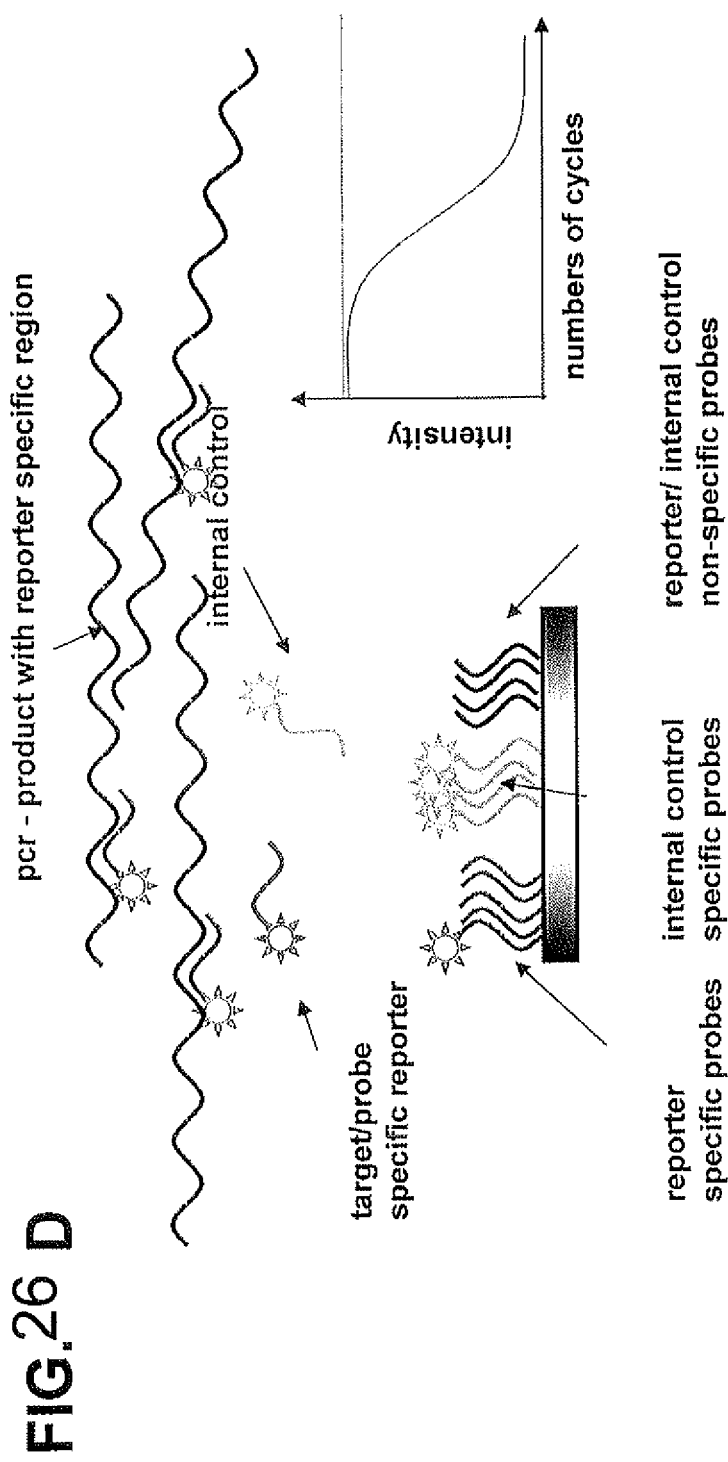
Figure 27:
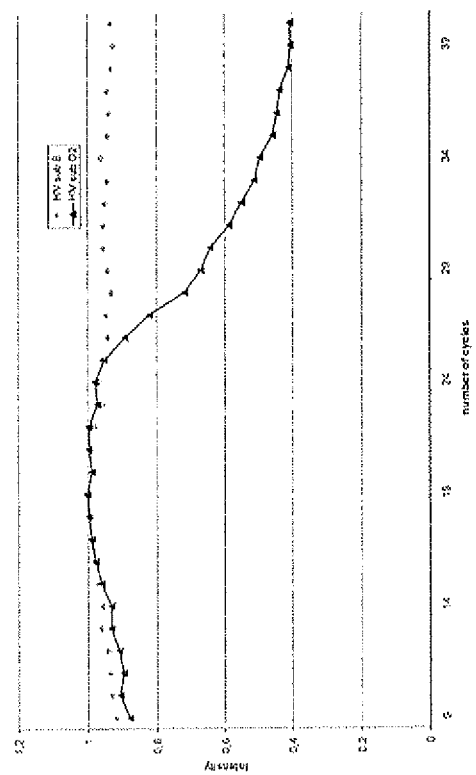
FIG. 27 shows the results of an exemplary embodiment of the competitive assay according to the present invention for determining the amount of HIV subtype B (FIG. 27A) and HIV subtype $O_2$ in a sample (FIG. 27B).
Figure 27:
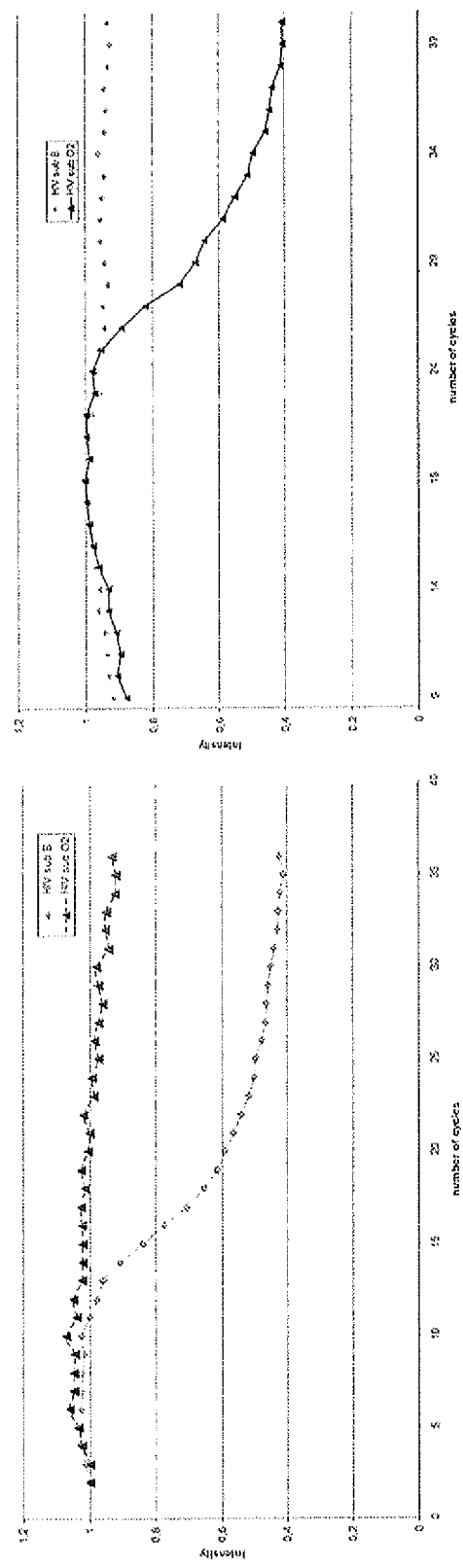

FIG. 27 shows the results of an exemplary embodiment of the competitive assay according to the present invention for determining the amount of HIV subtype B and HIV subtype O2 in a sample. In the experiment underlying FIG. 27A, only HIV Subtype B was present in the sample. It can be seen that the signal corresponding to a labelled nucleic acid reporter molecule specific for HIV subtype O2 (HIV sub O2) remains constant whereas the signal corresponding to a labelled nucleic acid reporter molecule specific for HIV subtype B (HIV sub B) decreases significantly after about 13 cycles of the PCR (cf. FIG. 26). In the experiment underlying FIG. 27B, only HIV Subtype O2 was present in the sample. It can be seen that the signal corresponding to a labelled nucleic acid reporter molecule specific for HIV subtype B (HIV sub B) remains constant whereas the signal corresponding to a labelled nucleic acid reporter molecule specific for HIV subtype O2 (HIV sub O2) decreases significantly after about 25 cycles of the PCR (cf. FIG. 26).

Figure 28A:
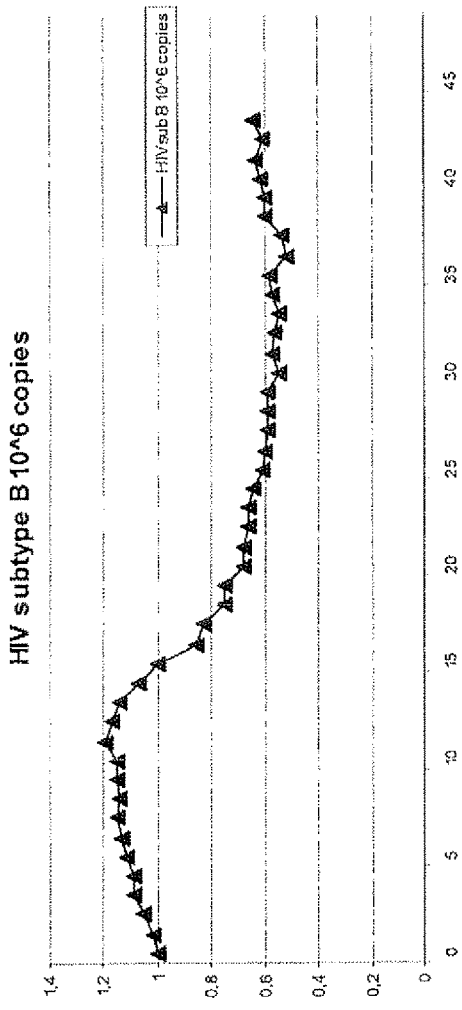
FIG. 28 shows the results of an exemplary embodiment of the competitive assay according to the present invention for determining different amounts of HIV subtype B in a sample.
Figure 28B:
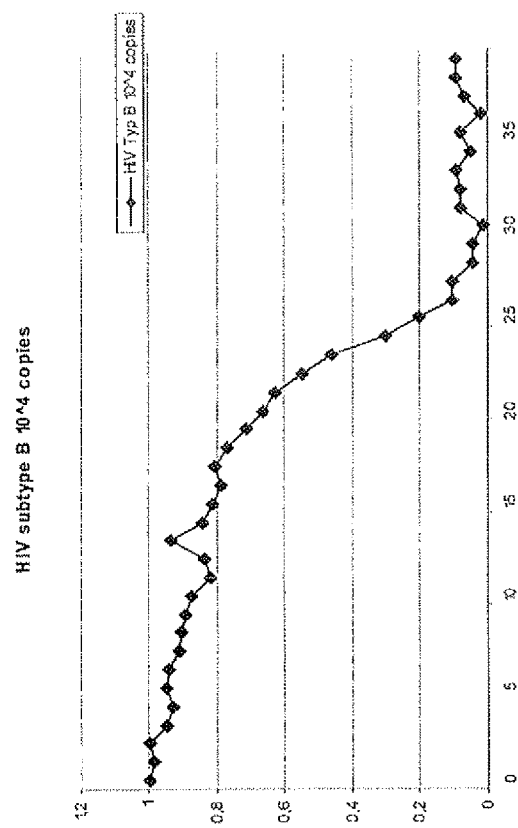

FIG. 28 shows the results of an exemplary embodiment of the competitive assay according to the present invention for determining different amounts of HIV subtype B in a sample. If $10^6$ copies of HIV are present in the sample the signal corresponding to a labelled nucleic acid reporter molecule specific for HIV subtype B (HIV sub B) decreases significantly after about 13 cycles of the PCR (see FIG. 28A). If only $10^4$ copies of HIV are present in the sample the signal corresponding to a labelled nucleic acid reporter molecule specific for HIV subtype B (HIV sub B) decreases significantly after about 19 cycles of the PCR (see FIG. 28B). It is apparent from FIG. 28 that the amount of PCR cycles required before a decrease in the signal is detectable allows conclusions as to the amount of target nucleic acid present in the sample to be analyzed.

Figure 29:
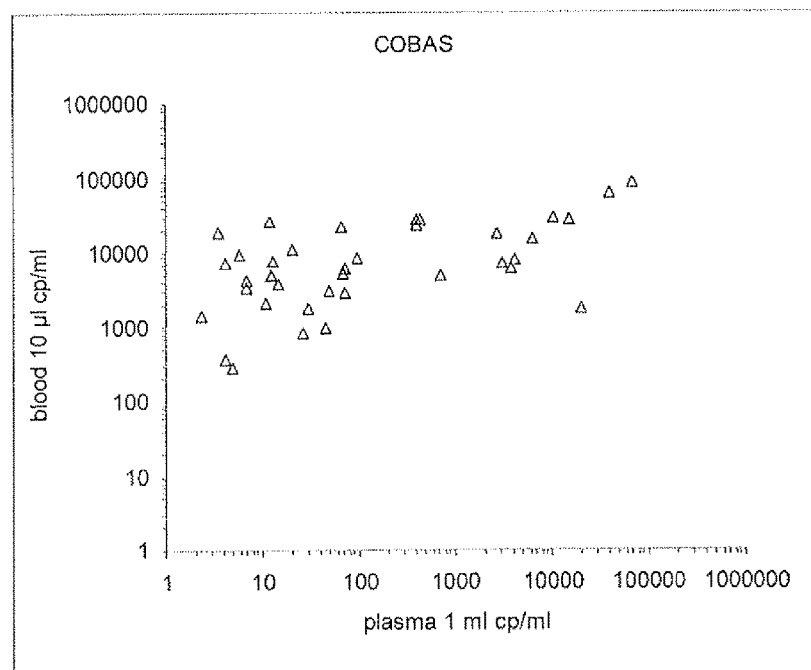
FIG. 29 shows the results of a PCR-based assay determining the respective copy numbers of HIV-1 RNA in blood plasma and whole blood samples from HIV-positive patients. Included in the analysis are only those samples in which at least 40 copies of HIV-1 RNA have been detected.

FIG. 29 depicts the results of a PCR-based assay (COBAS AmpliPrep/COBAS TaqMan HIV assay; Roche Diagnostics, Mannheim, Germany) determining the respective copy numbers of HIV-1 RNA in blood plasma and whole blood samples from 52 patients infected with HIV. In brief, whole blood samples of the patients were obtained by venous puncture. EDTA was added to the samples in order to prevent coagulation. Blood plasma was purified by centrifugation of the whole blood samples for 5 min at 4000×g and removal of the cell debris. 1 ml of the plasma samples and 10 µl of the whole blood samples (mixed with 990 µl phosphate buffered saline) were processed automatically in the COBAS AmpliPrep/COBAS TaqMan 48 devices (Roche Diagnostics, Mannheim, Germany) according to the manufacturer's instructions. The virus copy numbers (per ml sample volume) were automatically calculated by the COBAS AmpliLink software package and are shown as a scattered plot of the whole blood samples versus the plasma samples. The values obtained for the whole blood samples were multiplied by a factor 100 to correct for the different blood sample volumes (10 µl whole blood versus 1 ml plasma). For those blood plasma samples in which less than 40 virus copies were detected the copy number were calculated as described for FIG. 30. Due to the log scale, samples resulting in negative results (i.e. 0 virus copies per ml) in either blood or plasma samples are not shown.

Figure 30:
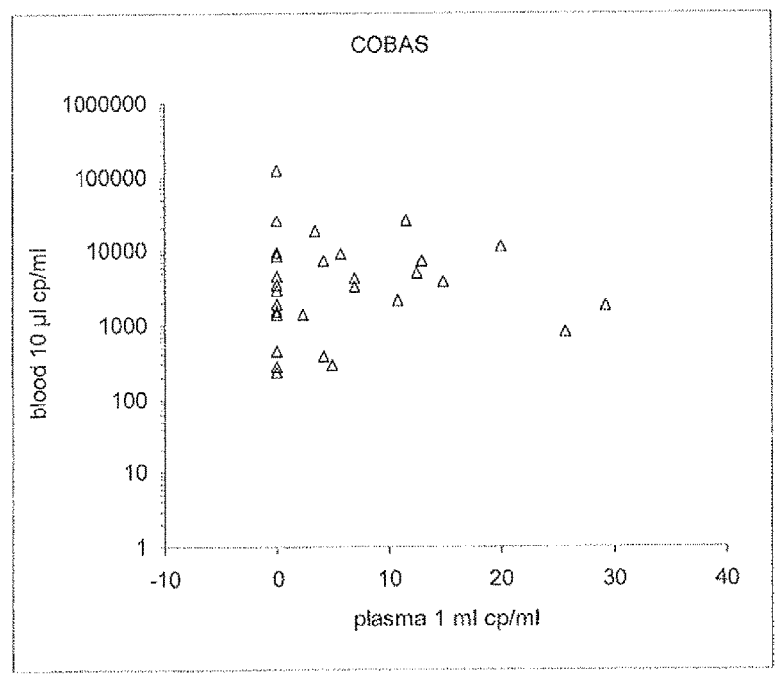
FIG. 30 shows the results of the PCR-based assay shown in FIG. 29 for those blood plasma samples in which no or less than 40 copies of HIV-1 RNA have been detected.

FIG. 30 depicts the results of the assay shown in FIG. 29 for those blood plasma samples in which no or less than 40 copies of HIV-1 RNA were detected. The virus copy numbers (per ml sample) were calculated manually by creating a calibration curve based on all calculated values for the respective copy numbers/ml sample (i.e. the threshold value given in the AmpliLink result file obtained).

Figure 31:
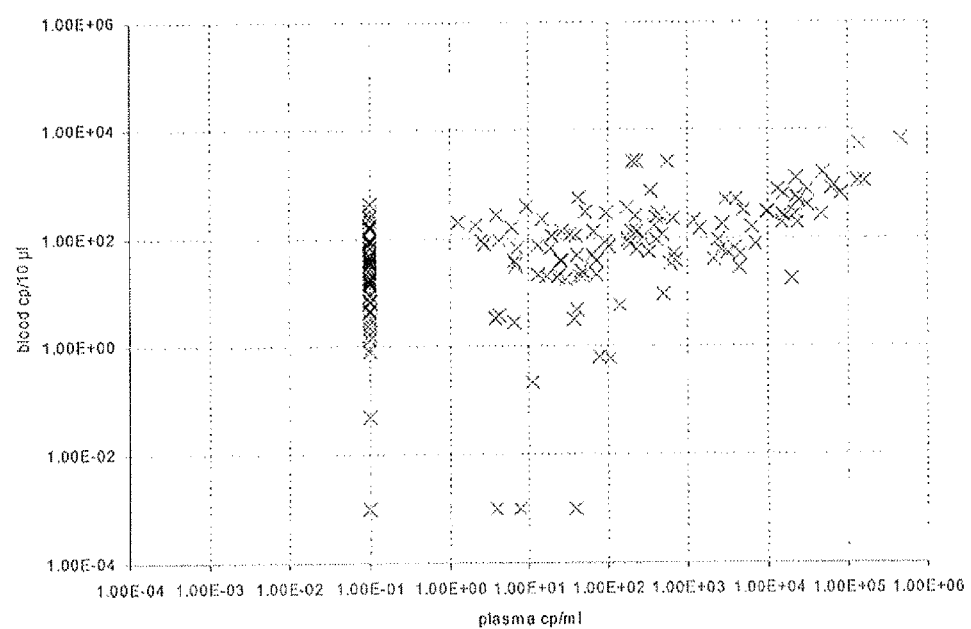
FIG. 31 shows the results of another PCR-based assay according to FIG. 29.

FIG. 31 depicts the results of another assay as shown in FIG. 1 determining the respective copy numbers of HIV-1 RNA in blood plasma and whole blood samples from 245 patients infected with HIV (including the 52 patients investigated in FIG. 29).

Figure 32:
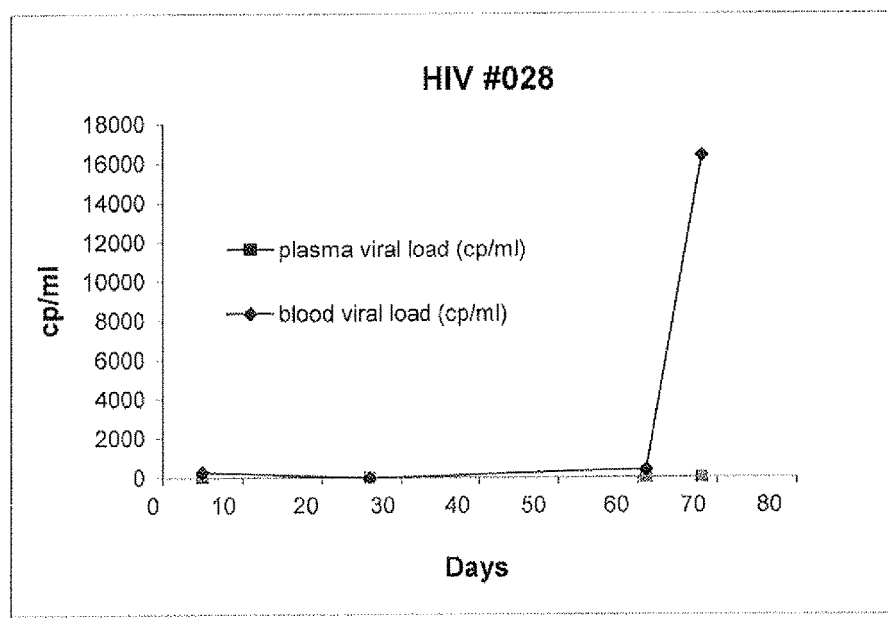

FIG. 32 shows the determination of the respective plasma and whole blood viral loads of a HIV-positive patient (patient #028) receiving a HIV antiviral therapy. The viral loads were determined according to the assay of FIG. 29. Whole blood and plasma samples were collected at different days during the regimen. Due to compliance problems (i.e. the patient had not taken the medicament as prescribed) a sudden increase of the HIV load was observed in the whole blood samples (but not in the plasma samples) about 60 days after onset of monitoring the patient's response to drug treatment.

FIG. 33 shows the determination of the respective plasma and whole blood viral loads of two HIV-positive patients receiving a HIV antiviral therapy: patient #003 (FIG. 33A), and patient #004 (FIG. 33B). The viral loads were determined according to the assay of FIG. 29. Whole blood and plasma samples were collected at different days during the regimen. In both patients, low viral loads in plasma and relatively high viral loads in whole blood were observed. From these data, it can be seen that the virus is still actively replicating during the regimen but that the replicating HIV pool is mainly cell-associated and thus the viral load in the plasma samples remains very low.

FIG. 34 shows the determination of the respective plasma and whole blood viral loads of two HIV-positive patients receiving a HIV antiviral therapy: patient #009 (FIG. 34A), and patient #066 (FIG. 34B). The viral loads were determined according to the assay of FIG. 29. Whole blood and plasma samples were collected at different days during the regimen. In patient #009, the viral load in plasma was below the limit of detection but in whole blood (apparently mainly cell-associated) HIV could be detected. In patient #066, due to compliance problems (i.e. the patient had not taken the medicament as prescribed) an increase of the HIV load was observed both in the whole blood samples until 35 days after onset of monitoring the patient's response to drug treatment. Afterwards, another therapy was started resulting in a decrease of the viral loads. Even though the respective time courses observed for whole blood and plasma viral loads were similar, in absolute numbers, the viral load in the whole blood samples was at any time higher than that of the plasma samples.

Figure 35:
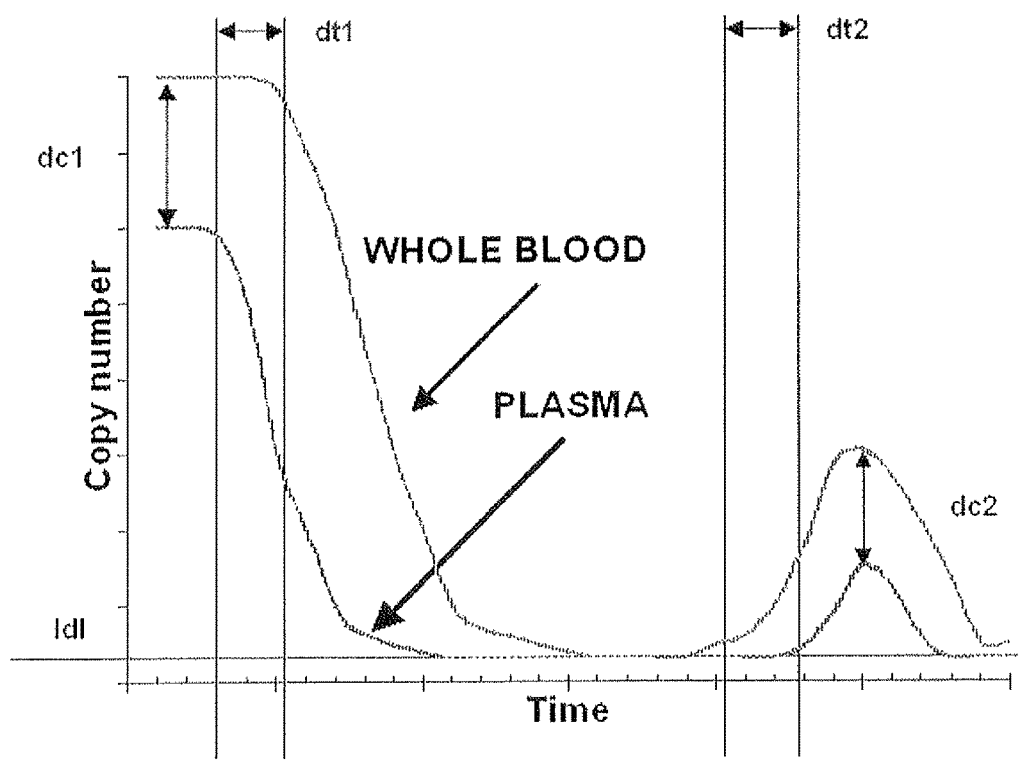
FIG. 35 depicts typical time courses of viral copy numbers in whole blood and blood plasma samples.

FIG. 35 depicts typical time courses of viral copy numbers observed in whole blood and blood plasma samples. The designation "ldl" denotes the lower detection limit of the analysis performed. At any time, the viral copy numbers observed in the whole blood samples are higher than the respective copy numbers of the blood plasma samples (cf. "dc1" and "dc2" designating "differences in copy number"). In many cases, however, in the plasma samples the virus copy numbers decrease earlier and increase later than in the whole blood samples, respectively (cf. "dt1" and "dt2" designating "differences in time").

In the following, referring to FIG. 36 a device 800 according to another exemplary embodiment will be explained.

A lysis chamber 802 is provided in which materials needed for lysing may be stored in a dried form. A central well 812 serves for performing all solid phase coupling procedures required for operating the device 800 as well as the amplification of the target. Additional wells 804, 806, and 808 are provided in which various further substances are provided in dried form and which may serve for washing procedures, a PCR procedure, etc. For instance, in the original state before starting the assay, lysis well 802, PCR/RT buffer well 808, wash buffer well 806 and wash buffer well 804 contain the appropriate agents for the respective step of the assay. A waste chamber 814 is provided as a well in which liquids can be transported which are no longer needed for the analysis.

Figure 36:
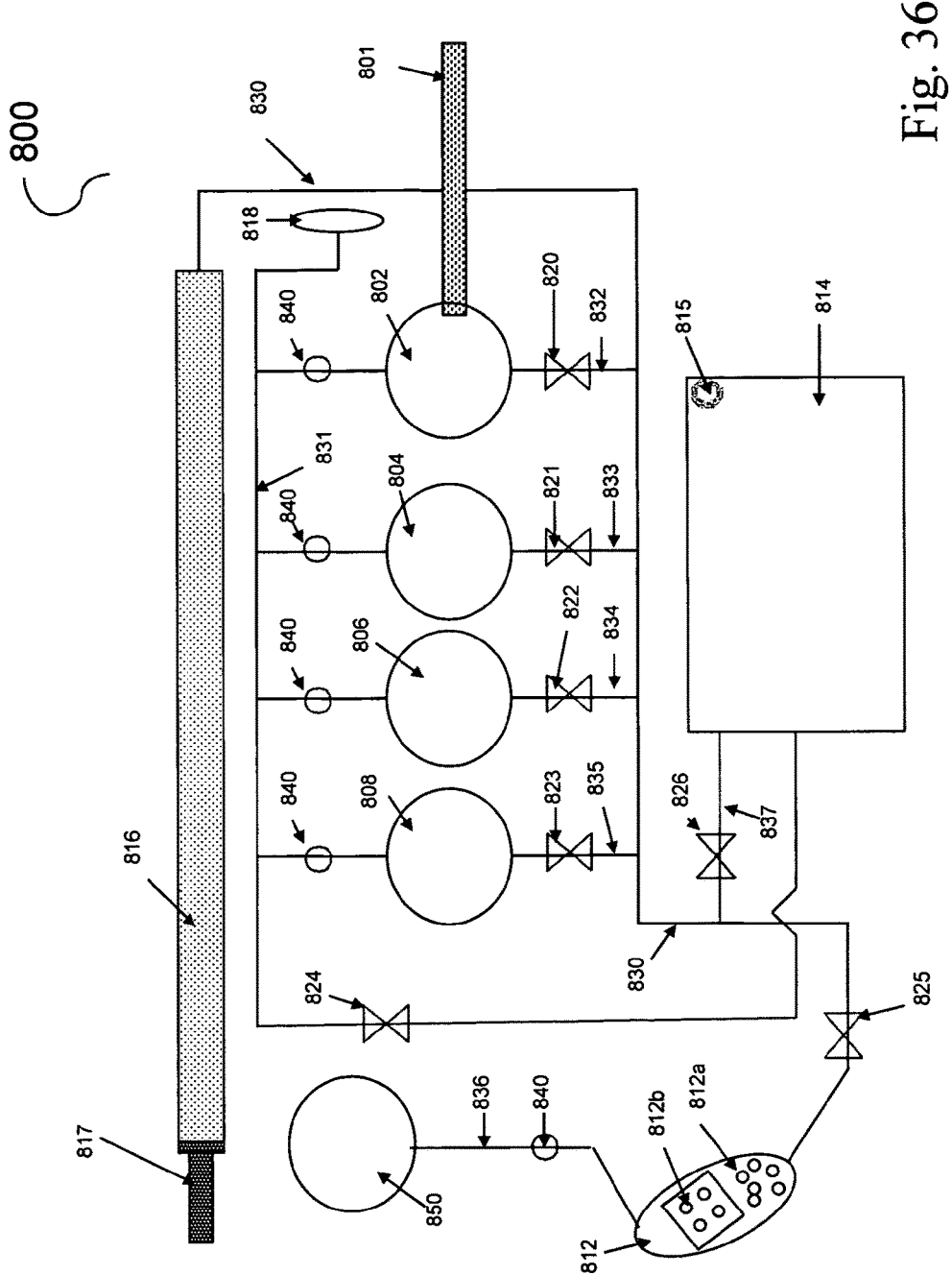
FIG. 36 schematically illustrates a device according to another exemplary embodiment.

Although not shown in FIG. 36, a liquid absorbent material may be provided in the waste chamber 814 which can absorb fluids entering the waste chamber 814. By taking this measure, undesired back flow of liquids from the waste chamber 814 into other portions of the device 800 may be securely prevented to thereby avoid any contamination. For instance, swellable polymers (which may also be used in diapers) may be employed for such a purpose.

Waste chamber 814 may include an opening 815 for venting the device 800. The opening may be capped by a filter which only allows gas to pass and which prevents liquids, aerosols and macromolecules such as DNA or RNA from leaving the device.

Beyond this, a fluid reservoir 816 is shown via which fluids may be stored within the device and/or injected into the device 800. In some embodiments, the fluid reservoir 816 is a reservoir containing water or another solvent which may be needed for analysis, wherein the reservoir has a variable volume. By lowering the volume e.g. by applying an external force via an actuator 817 the content of reservoir 816 may be injected into device 800. In some embodiments, fluid reservoir 816 is a chamber which is connected to the microfluidic network via a septum (not shown). Before starting the analysis, the chamber is fluidically separated from the fluidic network. When starting the analysis, the septum will be opened thereby connecting the fluid reservoir with the fluidic network allowing the content of the reservoir, under an external force, to be released into the channels and wells of device 800.

As can be taken particularly from FIG. 36, a plurality of fluid connection ports 820-826 are provided. Although not shown in FIG. 36, any one of the fluid connection ports 820-826 may be covered by a flexible member which may be compressed by an actuator pin (not shown in FIG. 36) so that the pins may serve for selectively opening or closing any individual one of the fluid connection ports 820-826 thus fulfilling a valve function, e.g. as explained in FIGS. 17a and b or FIG. 21.

Furthermore, a microfluidic network of a plurality of channels 830-837 are foreseen to connect the various fluid connection ports 820-826 and wells 802, 804, 806, 808 and 812.

Window portions 840 accessible by light barriers are shown which may serve to detect optically when a meniscus of a fluid column within the device 800 passes transparent window portions 840 related to the light barriers. When one of the light barriers detects that one of the chambers corresponding to the window portions 840 is full with a liquid or overflows, this may be detected optically and may serve to generate a control signal for controlling a control unit (not shown in FIG. 36) to control the operation of the device 800 correspondingly.

Although not shown in FIG. 36, any one of the wells 802, 804, 806, 808 and 812 may be covered by a flexible member which may be compressed by an actuator pin (not shown in FIG. 36) so that the pins may serve for selectively pressing on the wells 802, 804, 806, 808 and 812, thus serving as mixers or pumps.

Reference numeral 818 denotes a connection to pressurized air so that pressurized air may be introduced into device 800. For example, when fluid connection ports 821-824 and 826 are closed and fluid connection ports 820 and 825 are open, pressurized air may flow via connection 818 into well 802, via connection port 820, channel 830, fluid connection port 825 into well 812. Thus, in case well 802 is filled with a liquid it is possible to pump the content of well 802 into well 812 using pressurized air. For instance, the device may comprise a septum which may be punched in, in order to pump air or gas into the device. By pumping air or gas into the device, liquids may be forced or pressed from wells 802, 804, 806 and 808 into the central well 812 by opening the respective valves or fluid connecting ports.

In the following, an exemplary assay performed in the device 800, particularly based on the central well 812, will be explained which may allow to perform a determination of HIV load in a fast manner, for instance in less than one hour.

Within the central chamber 812, a binding member such as beads 812a may be provided. The binding member may be configured to capture target molecules (for instance HIV RNA and DNA) from a previously lysed sample. E.g., the binding member may be configured to bind an anchor group, such as biotin, of a capture molecule to bind complexes comprising a target polynucleotide and the capture molecule, wherein the capture molecule comprises a binding portion specific to a region of the target polynucleotide and the anchor group. The central well 812 may be equipped with filters such as fits (not shown in FIG. 36) preventing beads in the central well 812 from being removed from this well under the influence of the streaming force of the fluids.

In one embodiment, a whole blood sample (or any other sample) may be transported in the well 802, for instance for lysing. Blood may be introduced or pressed into the device 800 by first applying the blood to a capillary 801, the capillary 801 being in contact with the lysing chamber 802, then closing the capillary with a plug (not shown) thereby increasing the pressure within capillary 801 and forcing or pressing the blood sample into the lysing chamber 802.

For this purpose, the corresponding lysing agents as described above are provided in dried form in the lysis well 802. The lysis well may further comprise the capture molecules each comprising an anchor group and a binding portion specific to a region of the target polynucleotide. The sample which may now comprise complexes each comprising a target polynucleotide and a capture molecule may then be transported into the central well 812.

In the central well 812, a first binding member such as beads 812a or a surface functionalization may be provided so that targets or complexes comprising a target polynucleotide and a capture molecule may bind on solid capture structures in the central chamber 812. An incubation may be performed so that the beads properly mix with the sample material.

The central well 812 may be in fluid communication via e.g. a channel 836 with a further well 850 or chamber serving as a pneumatic spring. The further well 850, also denoted as spring well, may be adapted for receiving a content of the central well 812. The central well 812, out of which the content is displaced when the central well 812 is accommodated with liquids is connected via the microfluidic network. The filling substance, in normal cases air, being included in the central well 812 before accommodating the liquid can then be stored in the spring well 850. It should be noted that the spring well may store any substances irrespective of the consistency, i.e. liquids and gases.

The spring well 850 may also be adapted to build up a pressure when receiving a content from the central well 812. The well 850 may also be adapted to release a build up pressure into the central well 812 by releasing the content, e.g. gas or air, into the central well. Thus, the well 850 may serve as a pneumatic spring, allowing displacement of the liquid from the central well 812 through opened valve 825. In this embodiment, an active displacement by e.g. an external pressured air supply may be rendered superfluous, since the build up pressure instead of e.g. external pressured air serves for displacing an accommodated liquid from the central well 812.

For instance, when filling the central well 812, air or gas included in the pneumatic spring will be compressed and the pressure within the pneumatic spring will increase. Thus, when filling the central well the liquid may be introduced under pressure, e.g. with a pressure of 500 to 2000 mbar, for instance 800 mbar. If the filling pressure is reduced (e.g. by opening valve 825), the pressure in the pneumatic spring 850 will be greater than the filling pressure, so that the inserted solution will be pressed out or forced out of the central well 812.

The pneumatic spring 850 may be dimensioned such that the built-up accumulated pressure therein is sufficient to entirely empty the contents of the central well into the waste container 814. For instance, the volume of the pneumatic spring well 850 may be essentially as large as of the central well 812. In some embodiments, the volume of the pneumatic spring is twice or triple the volume of central well 812 or half the volume of central well 812. For instance, the volume of the pneumatic spring well 850 may be between 50 and 300 μl, such as 100 μl, 150 μl, 200 μl or 250 μl.

The well 850 may be provided with a channel 836 as a fluid communication, i.e. a liquid or gas communication, between the well 850 and central well 812. The orifice of the channel 836 on the central well side may be is positioned in a direction opposite a direction of gravity in a normal operating position. This means that the orifice is at the upper part of the central well 812 in normal gravity conditions. Thus, it can be avoided that the accommodating liquid of the central well 812 is unintentionally released into the well 850. The well 850 may be in fluid communication with the central well 812 via a microfluidic network. Thus, well 850 may serve as a pressure reservoir or a pressured gas spring and may be remotely located from the second structure.

According to an exemplary embodiment, a detecting device 840, e.g. a light barrier, is provided between the central well 812 and well 850, which detecting device 840 is adapted for detecting presence of an accommodating liquid accommodated in the central well 812. The device 840 may be anywhere in the fluid connection between the central well 412 and the well 850.

By releasing the built-up pressure in the spring well 850 (e.g. by opening fluid connection ports 825 and 826) the liquid (i.e. non-captured components of the lysed sample) is forced or pressed from the central well 812 into the waste 814. Thus, sample components which have not been captured by the beads in the central well 812 are transported into the waste chamber 814. Thus, only targets remain in the central well 812, and the remainder of the whole blood sample is now in the waste 814. Thus, the central well 812 now houses the beads together with complexes comprising capture probes and targets.

Subsequently, the central well 812 may be washed, wherein components for a wash buffer provided in a solid manner in a wash buffer well 804 are used to produce a wash buffer. Such a washing procedure may be advantageous since, after the capturing procedure, some impurities may still be present in the chamber 812.

As already indicated above, a wash buffer is prepared in the wash buffer well 804. In the wash well 804, salts for such a wash buffer may be present in dried form. For preparing the wash buffer, water from liquid reservoir 816 may be transported via channels 830, 833 and fluid connection port 821 (while fluid connection ports 820, 822, 823, 825 and 826 are closed) into the wash well 804 until a transparent window 840 coupled to component 821 is filled with water, which may be detected by detecting a meniscus passing the light barrier adjacent the transparent window next to well 804. Upon receipt of a corresponding detection signal, the supply of water may be terminated.

In some embodiments, an actuator (not shown) may then reciprocate upwardly and downwardly to compress a flexible cover element covering the wash well 804 to perform mixing to dissolve the salts provided therein.

The prepared wash buffer in the wash buffer well 804 may then be pumped into the central well 812 by applying a pressure via components 818, 831, 804, 821, 833, 830, 825 so that a washing procedure may be performed in the central well 812. By pumping the content of well 804 into well 812 the pressure in well 850 increases. After this washing, the wash solution may be pumped in the waste chamber 814 by releasing the pressure of well 850, e.g. as described above.

Then, the buffers in wells 806 and 808 may be prepared and transferred into and out from chamber 812 equally.

Next, a reverse transcription followed by PCR may be performed to convert target RNA into a corresponding DNA and subsequently amplify the DNA. Such a procedure is specifically necessary in case of detecting Retroviridae such as HIV, and the reverse transcription step may be dispensable in other cases, for instance when DNA viruses are detected. To perform such a reverse transcription PCR, components required for reverse transcription such as a primer, an enzyme and a buffer may be pumped from a RT/PCR well 808 into the central well 812.

PCR amplification is then performed in the central well 812. For this purpose, a PCR is performed in the central well 812 by performing a temperature cycle, that is to say by repeating e.g. 40 times a procedure with 5 s at 95° C. and 10 s at 60° C. In another embodiment a temperature cycle comprising 3 or more different temperatures, e.g. comprising 30 or 40 cycles of 20 s at 95° C., 30 s at 55° C. and 30 s at 72° C., can be performed. However, other PCR cycling protocols can be performed in the central chamber, too.

In some embodiments, for adjusting the temperature in the central well 812 two heating plates may be provided above and below the central well 812. In another embodiment, one of the two heating wells may be continuous and the other one may have a recess to allow for a subsequent optical detection. In some embodiments, the heating plates are heating and/or cooling plates, such as Peltier elements.

In some embodiments, during the amplification the detection may take place as described above.

For instance, in a first embodiment, a competitive assay of capture molecules may be performed in the central well 812. Thus, in this embodiment, a first binding member such as beads are used for capturing the complexes each comprising a target molecule and a capture molecule, and a second binding member comprising an array of reporter specific capture molecules immobilized in the central well 812 is used for detection. The competitive assay comprises forming complexes of a subset of the amount of reporter compound with at least a subset of the amount of target nucleic acid, the forming of these complexes inhibiting the capturing of the reporter compound by the array of reporter specific capture molecules immobilized in the central well 812. The reporter specific capture molecules immobilized in the central well 812 are capable of capturing at least a remaining subset of the amount of reporter compound not in complex with a target polynucleotide. By providing an array 812b of different kinds of reporter specific capture molecules in the well 812 for detection, it is possible to distinguish between different types of the HI virus, for instance type 1 HIV and type 2 HIV, and it may be even possible to distinguish between different subtypes of the HI virus.

In another embodiment, it is possible to use the same binding member, e.g. beads, which have already been used for the capturing procedure also for the detection. In this embodiment, a capture oligonucleotide being attached to the beads via an anchor group may hybridize with a complex of amplified target DNA, which itself may comprise a fluorescence label.

The captured reporter compounds or the captured target molecules may be detected by an optical detection for instance using the fluorescence label as described above. Particularly, an optical system having a light source (not shown) and a light detector (not shown) may be operated in a manner so as to measure the time dependence of the signal during the PCR, which allows deriving the viral load of HIV. In other words, the time dependence of the fluorescence signal may be acquired and evaluated.

According to an exemplary embodiment, the central well 812 will be irreversibly sealed before starting PCR. This sealing can be carried out by welding an inlet and, if necessary, an outlet. In case of the presence of a third structure, e.g. a pneumatic spring or spring well 850, it is possible to seal only the inlet. The sealing can be carried out for example by using a hot pin which is pressed into the valve 825 or onto the channel, causing the plastic to melt and thus sealing the valve or the channel. The PCR chamber can thus be safely sealed.

According to a further exemplary embodiment, the central well for PCR is filled such that a flexible first and second face or cover layer carries out a convex bending. The layers can thus be forced or pressed against the heating/cooling elements, thus allowing for an efficient thermal transition between the heating/cooling elements and the central well.

In some embodiments, for the test the capillary 801 of the device will be filled with blood. When covering the capillary with a cover (not shown in FIG. 36), the blood will be supplied to the lysis chamber or lysis well. The device will now be inserted into the detector and the assay will start. Firstly, all chambers or wells (except the central well) will be filled with water. The respective valves or fluid connecting ports will be opened and the water out of the reservoir 816 will be pumped into the wells until a light barrier or detecting device 840 at the upper section of the well 802 signals that the well 802 is filled. The water flow for the respective well will be stopped and the next well will be filled. By filling with water, the dried agents or reagents in the respective well will be dissolved. When the respective solutions are ready to use, firstly, the content of the lysis well 802 will be pumped into the central well 812. For this purpose, the valve or fluid connecting port below the lysis well as well as the valve or fluid connecting ports connecting the central well will be opened so that a fluid connection will be established between both wells. When the lysis mix containing the target nucleic acids flows into the central well 812, the target nucleic acids will be captured via the capture molecules onto the binding matrix in the central well. In order to increase the efficiency of capturing the of target nucleic acids, the lysis mix will be pumped into the central well a plurality number of times, by moving between the central well and the lysis well a plurality number of times. Then, the lysis solution will be pumped into the waste container by using the pneumatic spring 850 as described above.

The invention is further described by the following examples, which are solely for the purpose of illustrating specific embodiments of this invention, and are not to be construed as limiting the scope of the invention in any way.

EXAMPLES

Example 1: Competitive Assay for Determining Human Poliovirus 1 DNA

The principle of the competitive assay performed is schematically shown in FIG. 22. DNA of human poliovirus 1 isolate TCDC01-861 (GenBank accession number AF538843) cloned into a suitable expression vector (p 2.1-TOPO®, Clontech, Inc. Palo Alto, Calif., USA) was used as a DNA template (herein also designated "EV" (enterovirus) DNA).

Two samples, each containing 10⁴ DNA copies were analyzed in parallel: the first sample was subjected to PCR amplification using a Rotor-Gene 6000 real-time rotary PCR analyzer (Corbett Life Sciences, Sydney, Australia) according to the manufactures instructions.

The second sample additionally included a reporter molecule having the same nucleotide sequence as the Taqman® probe but comprises a CY3 carbocyanine label (Invitrogen Corporation, Carlsbad, Calif., USA) at its 3' terminus instead of FAM/TAMRA labels and was amplified using directly in a reaction chamber of an assay device, in which the array was disposed on the heatable base surface.

The following PCR primers were used:

```
forward PCR primer:
                                        (SEQ ID NO: 1)
pr_for_EV_02: 5'-CAAACCAGTGATTGGCCTGTCGTAACG-3'

(corresponding to the nucleotide positions 492-518 of AF538843).

reverse PCR primer:
                                        (SEQ ID NO: 2)
pr_rev_EV_01: 5'-TTCACCGGATGGCCAATCCAATTCG-3'

(corresponding to the nucleotide positions 617-641 of AF538843).
```

Thus, PCR resulted in the amplification of a 150 bp DNA fragment. PCR samples contained 200 nM (final concentration) each of the PCR primers as well as the EnzymMix® and the reaction buffer of the Ultrasense RT-PCR Kit (Invitrogen Corporation, Carlsbad, Calif., USA) according to manufactures instructions.

Furthermore, for detecting the amplified PCR fragment using the Rotor-Gene 6000 real-time rotary PCR analyzer the according PCR sample contained 100 nM (final concentration) of a dual-labelled so-called Taqman® probe comprising a 6-carboxy-fluorescein (FAM) label at its 5' terminus (i.e. the fluorophor) and a 6-carboxy-tetramethyl-rhodamine-succinimidylester (TAMRA) label at its 3' terminus (i.e. the quencher), respectively (both labels were purchased from Invitrogen Corporation, Carlsbad, Calif., USA). The probe has the following sequence:

```
HP_EV2_001:
                                        (SEQ ID NO: 3)
FAM-5'-ACCGACTACTTTGGGTGTCCGTGTTT-3'-TAMRA (corresponding to the nucleotide positions 536-561 of AF538843).
```

For performing the competitive analysis, the PCR sample further contained 20 nM (final concentration) of a reporter molecule having the same sequence but a different label as the Taqman® probe, namely a CY3 carbocyanine label at its 3' terminus (Invitrogen Corporation, Carlsbad, Calif., USA):

```
                                        (SEQ ID NO: 4)
EV2_02CY3: 5'-ACCGACTACTTTGGGTGTCCGTGTTT-3'-CY3

(corresponding to the nucleotide positions 536-561 of AF538843).
```

Real-time PCR was performed according to the following temperature profile: 2 min at 94° C., and subsequently 50 cycles of 5 s at 94° C., 30 s at 62° C., and 30 s at 72° C.

During PCR fluorescence signals for both reactions are shown in FIG. 23.

Example 2: Array-Based Competitive Assay for Determining HIV1 Gag/Env DNA

The principle of the competitive assay performed is schematically shown in FIG. 24A. DNA of a synthetic HIV1 gag/env fusion construct (EMBL accession number A06258) cloned into the EcoRI endonuclease restriction site of the expression vector pCR® 2.1-TOPO® (Clontech, Inc. Palo Alto, Calif., USA) was used as a DNA template.

Furthermore, the following PCR primers were used:

```
forward PCR primer:
                                        (SEQ ID NO: 5)
cdia: 5'-TGAAGGGTACTAGTAGTTCCTGCTATGTC-3'

(corresponding to the nucleotide positions 214-232 of A06258).

reverse PCR primer:
                                        (SEQ ID NO: 6)
cdis: 5'-ATCAAGCAGCCATGCAAATGTT-3'

(corresponding to the nucleotide positions 384-405 of A06258).
```

Thus, PCR resulted in the amplification of a 151 bp DNA fragment having the following sequence: 5'-ATC AAG CAG CCA TGC AAA TGT TAA AAG AGA CCA TCA ATG AGG AAG CTG CAG AAT GGG ATA GAT TGC ATC CAG TCC ATG GAG GGC CTA TTG CAC CAG GCC AGA TGA GAG AAC CAA GGG GAA GTG ACA TAG CAG GAA CTA CTA GTA CCC TTC A-3' (SEQ ID NO: 7).

PCR was performed directly in the reaction chamber of the assay device, in which the array was disposed on the heatable base surface. PCR samples contained 200 nM (final concentration) each of the PCR primers as well as the EnzymMix® and the reaction buffer of the Ultrasense RT-PCR Kit (Invitrogen Corporation, Carlsbad, Calif., USA). For generating a calibration curve, different amounts of DNA template (in 1 µl) were used corresponding to 0, 10⁴, 10⁵, and 10⁶ DNA copies (each performed in quadruplicate).

For performing the competitive analysis, the PCR sample further contained 10 nM (final concentration) of a reporter molecule having a CY3 carbocyanine label at its 5' terminus (Invitrogen Corporation, Carlsbad, Calif., USA):

```
anti_cdso29_5'CY3:
                                        (SEQ ID NO: 8)
CY3-5'-TCCCATTCTGCAGCTTCCTCATTGATGGT-3'

(complementary to the cdso29_NH2 probe molecule described below).
```

PCR was performed according to the following temperature profile: 30 s at 95° C., and subsequently 36 cycles of 5 s at 95° C., 30 s at 50° C., and 30 s at 72° C.

The interaction of the reporter molecule with the two types of probes was determined in each cycle at the end of the annealing step using an optical detection system positioned opposite to the top surface of the assay device and the Iconoclust software package (Clondiag Chip Technologies GmbH, Jena, Germany). The exposure time during data acquisition was 2.5 s.

Two different types of probe molecules were captured on the array substrate in an arrangement as shown in FIG. 25A. Fluorescent labels alone were used as positive controls. The following probes were employed:

```
non-specific probe:
                                    (SEQ ID NO: 9)
ara_54986_NH2: 5'-ACCAGCTTTGAACCCAACAC-3'.

receptor-specific probe:
                                    (SEQ ID NO: 10)
cdso29_NH2:   5'-ACCATCAATGAGGAAGCTGCAGAATGGGA-3'.
```

The CT values ("thresholds"), as a measure for the onset of the exponential amplification phase, where the increase in fluorescence and thus DNA amount occurs in a linear manner, were determined using the Iconoclust software (Clondiag Chip Technologies GmbH, Jena, Germany) and plotted versus the respective DNA concentrations employed to generate a calibration curve (FIG. 24C). The mean CT values determined were as follows: 22.0 in the $10^4$ DNA copies-samples; 18.5 in the $10^5$ DNA copies-samples; and 15.0 in the $10^6$ DNA copies-samples.

In all samples employing the receptor-specific probe a progressive decrease in fluorescence intensity was observed as the number of PCR cycles increased. In contrast, in the sample using the non-specific probe no fluorescence was observed (FIG. 24B).

The arrangement of the different spots on the array substrate is schematically illustrated in FIG. 25A. The black circles denote spots (four parallel samples), where the specific probe (cf. FIG. 24) was used for capturing the reporter molecules, whereas the white circles refer to spots (four parallel samples), where the non-specific probe was used for capturing the reporter molecules. The grey circles represent positive controls, where the fluorescent label was spotted on the array substrate.

FIG. 25B shows photographs of the array (corresponding to the $10^5$ DNA copies-samples in FIG. 24B) that taken after amplification cycles 1, 12, 18, and 21, respectively. In the samples captured on the array via the specific probe molecules a progressive decrease in fluorescence signal intensity can be observed during the course of the PCR amplification that, in turn, corresponds to a concomitant increase of the amount of PCR product amplified that can be quantified by comparison with a corresponding calibration curve.

Example 3: Determination of the HIV Load in Blood Samples of HIV-Positive Patients Blood samples were initially obtained from 52 patients infected with HIV, who were medicated at the HIV ambulance, Friedrich-Schiller-University Jena, Germany. The patients have not been grouped according to their gender, age, etiology of the HIV infection, clinical symptoms, HIV species/subtypes present, accompanying diseases, and the like.

Whole blood samples of the patients were obtained from the patients by venous puncture. EDTA in a final concentration of 5 mM was added to the samples in order to prevent coagulation (i.e. the formation of blood clots) of the samples. The samples were stored at 4° C. and analyzed within 24 hours after sample collection.

Blood plasma was purified from the whole blood samples by centrifugation for 5 min at 4000×g and removal of the cell debris. 1 ml of the plasma samples and 10 µl of the whole blood samples (mixed with 990 µl phosphate buffered saline) were subjected to further analysis. A sample volume of 1 ml is required for performing the COBAS AmpliPrep/COBAS TaqMan HIV assay used for virus detection (Roche Diagnostics, Mannheim, Germany).

The whole blood and plasma samples were processed automatically in the COBAS AmpliPrep device according to the manufacturer's instructions. In brief, 850 µl of the samples were lysed in a chaotropic buffer in the presence of proteinase K in order to release any nucleic acids. Furthermore, a negative control (without any nucleic acid) and two positive controls, which contain an RNA standard corresponding to a viral load of about 500 copies/ml and 500.000 copies/ml, respectively, were prepared.

The nucleic acids present in the samples were purified by non-specific capture onto magnetic silica particles. After washing, the nucleic acids were eluted from the silica particles by adding 75 µl elution buffer. 50 µl of the eluate were mixed with 50 µl of COBAS TaqMan master mix (also comprising HIV specific PCR primers) and transferred to the COBAS TaqMan 48 device for performing a quantitative RT-PCR according to the manufacturer's instructions.

The viral load of the samples (i.e. the HIV copy number/ml sample)—normalized with respect to a standard RNA added to each sample before start of processing—were automatically calculated by the COBAS AmpliLink software package. The values obtained for the whole blood samples were multiplied by a factor 100 to correct for the different blood sample volumes (10 µl whole blood versus 1 ml plasma).

Notably, included in this automatic data analysis are only those samples, in which at least 40 copies of HIV-1 RNA were detected, which represents the detection limit of the AmpliLink software. Any samples having less than 40 copies of HIV-1 RNA (i.e. in fact corresponding to 40 copies of HIV-1 RNA/ml plasma and 4.000 copies of copies of HIV-1 RNA/ml whole blood when corrected for the different sample volumes used) were analyzed manually. The virus copy numbers/ml sample were calculated by creating a calibration curve based on all calculated values for the respective copy numbers/ml sample (i.e. the threshold value given in the AmpliLink result file obtained).

The results obtained are summarized in the following Table 1, which illustrates the respective numbers of whole blood and plasma samples, in which no ("negative"), less than 40 copies/ml ("<40"), and more than 40 copies/ml ("positive") of HIV RNA were detected.

The results—expressed as scattered plots of the values calculated from the whole blood samples versus those calculated from the corresponding plasma samples—are also shown in FIGS. 30 and 31. In particular, FIG. 29 illustrates the results obtained by the automatic data analysis performed by the AmpliLink software, whereas FIG. 30 depicts the results obtained by manual calculation for those plasma and whole blood samples, in which no or less than 40 copies of HIV RNA were detected.

TABLE 1

| Number of samples | | 10 µl whole blood | | |
|---|---|---|---|---|
| | | negative | <40 | positive |
| 1 ml plasma | negative | 13 | 8 | 6 |
| | <40 | 3 | 8 | 8 |
| | positive | 0 | 4 | 18 |

Form the results obtained it becomes apparent that the use of plasma samples for detecting HIV may lead to false-negative results. The virus load in the plasma samples in several of the HIV-infected patients analyzed were negative, which suggests the absence of any infection HIV particles circulating in the blood stream, even though in the corresponding whole blood samples HIV RNA in considerable copy numbers could be detected.

These results were corroborated in a subsequent analysis comprising a collective of 245 HIV-infected patients (including the 52 patients investigated in the first analysis). The assay was performed as described above. The results obtained—expressed as a scattered plot—are shown in FIG. 31 and also summarized in the following Table 2.

TABLE 2

| Samples analyzed | total number | negative | positive <40 |
| --- | --- | --- | --- |
| 1 ml plasma | 245 | 109 (44%) | 42 (17%) |
| 10 µl whole blood | 245 | 50 (20%) | 36 (15%) |

61% of the 245 plasma samples analyzed were HIV-negative or contained less than 40 copies of HIV-1 RNA (i.e. in fact corresponding to 40 copies of HIV-1 RNA/ml plasma and 4.000 copies of copies of HIV-1 RNA/ml whole blood when corrected for the different sample volumes used), whereas this portion represents only 35% of the 245 whole blood samples analyzed. In other words, in 65 (43%) patients whose plasma samples comprised no or less than 40 copies of HIV-1 RNA the corresponding whole blood samples were in fact HIV-positive (i.e. more than 40 copies of HIV-1 RNA could be detected).

It is tempting to speculate that this "additional" pool of HIV is mainly attributable to those HIV particles being attached to blood cells such as neutrophils, B lymphocytes, platelets, and erythrocytes (cf. the discussion in the background section above) that are considered to represent an important marker for the continuous viral replication in infected cells. Thus, assay methods using plasma samples will fail to detect nucleic acids originating from cell-associated HIV and thus give rise to false-negative results that may potentially be detrimental for the patients affected. Accordingly, the amount of total HIV nucleic acids appear to represent a more accurate and reliable diagnostic marker than the viral load in the plasma.

Example 4: Use of the HIV Load in Whole Blood Samples as a Diagnostic Marker

The respective plasma and whole blood viral loads of five HIV-positive patients from the above collective of subjects receiving a HIV antiviral therapy (namely, patients #028, #003, #004, #009, and #066) were determined according to the assay described in Example 1 at different time points during the regimen. The respective results obtained are summarized in the following Tables 3 to 7 as well as FIGS. 33 to 35.

With regard to patient #028, whole blood and plasma samples were collected at different days (i.e. at day 5, 25, 61, and 68) after onset of monitoring the patient's response to HIV therapy. The assay results obtained are shown in Table 3 as well as in FIG. 32.

TABLE 3

| HIV #028 | | |
| --- | --- | --- |
| Day of sample collection | Viral load plasma (copies/ml) | Viral load whole blood (copies/ml) |
| 5 | 0 | 280 |
| 25 | 7 | 100 |
| 61 | 0 | 410 |
| 68 | 0 | 16384 |

Surprisingly, a dramatic and sudden increase of the HIV load in the whole blood was observed in the sample collected on day 68 after onset of monitoring the patient's response to drug treatment, whereas the HIV load in the plasma remains undetectable. After reporting this observation to the HIV ambulance at the Jena University Hospital it turned out that the patient has stopped taking the medicament as prescribed during the regimen. Apparently, this compliance problem has led to an increase in HIV replication which can only be detected in whole blood.

Even though the cause of this phenomenon remains unclear, it appears that the overall increase in HIV copy numbers is mainly attributable to an increasing number HIV particles remaining attached to blood cells, i.e. a HIV pool that cannot be detected in plasma samples.

With regard to patients #003 and #004, whole blood and plasma samples were collected at different days (i.e. at day 0, 60, 98, and 172 for #003; and at day 0, 42, 98, and 158 for #004) after onset of monitoring the patient's response to HIV therapy. The assay results obtained are shown in Tables 4 and 5 as well as in FIGS. 34A and 34B, respectively.

TABLE 4

| HIV #003 | | |
| --- | --- | --- |
| Day of sample collection | Viral load plasma (copies/10 µl) | Viral load whole blood (copies/10 µl) |
| 0 | 0.26 | 260.5 |
| 60 | 5.65 | 2565 |
| 98 | 2.04 | 2460 |
| 172 | 2.31 | 2470 |

TABLE 5

| HIV #004 | | |
| --- | --- | --- |
| Day of sample collection | Viral load plasma (copies/10 µl) | Viral load whole blood (copies/10 µl) |
| 0 | 0.24 | 21.1 |
| 42 | 0.20 | 112 |
| 98 | 2.19 | 259 |
| 158 | 0.97 | 249 |

In both patients, low viral loads in plasma and relatively high viral loads in whole blood were consistently observed. From these data, it can be seen that the virus is still actively replicating during the regimen but that the replicating HIV pool is again mainly cell-associated and thus not detectable in plasma samples.

With regard to patients #009 and #066, whole blood and plasma samples were collected at different days (i.e. at day 0, 66, and 136 for #009; and at day 0, 11, 35, and 42 for #066) after onset of monitoring the patient's response to HIV therapy. The assay results obtained are shown in Tables 6 and 7 as well as in FIGS. 35A and 35B, respectively.

TABLE 6

HIV #009

| Day of sample collection | Viral load plasma (copies/10 µl) | Viral load whole blood (copies/10 µl) |
| --- | --- | --- |
| 0 | 0 | 43.5 |
| 66 | 0 | 15.7 |
| 136 | 0 | 3.6 |

TABLE 7

HIV #066

| Day of sample collection | Viral load plasma (copies/10 µl) | Viral load whole blood (copies/10 µl) |
| --- | --- | --- |
| 0 | 2.3 | 61.4 |
| 11 | 1400 | 5410 |
| 35 | 4650 | 6675 |
| 42 | 75.8 | 292 |

In patient #009, the viral load in plasma was below the limit of detection but in whole blood HIV could be detected. Again, this pool of actively replicating HIV thus appears to be mainly cell-associated.

In patient #066, due to compliance problems (i.e. the patient had not taken the medicament as prescribed) an increase of the HIV load was observed both in the whole blood samples until 35 days after onset of monitoring the patient's response to drug treatment. Afterwards, another therapy was started resulting in a decrease of the viral loads. Even though the respective time courses observed for whole blood and plasma viral loads were similar, in absolute numbers, the viral load in the whole blood samples was at any time higher than that of the plasma samples.

Thus, based on these results the HIV load in whole blood appears to represent a more meaningful and significant diagnostic marker than the HIV load in plasma, not only for monitoring disease progression in a patient infected with HIV but also for monitoring the efficiency of antiviral treatment.

It should be noted that the term "comprising" does not exclude other elements or features and the "a" or "an" does not exclude a plurality. Also elements described in association with different embodiments may be combined.

It should also be noted that reference signs in the claims shall not be construed as limiting the scope of the claims.

The invention claimed is:

1. A method comprising:

providing an untreated fluid sample having a volume of 1 µl to 50 µl;

transporting the sample in a first structure of a device, the device including a microarray, in the first structure of the device, releasing contents from one or more cells, spores or viruses in the device, wherein the sample is modified by release of the content and wherein releasing comprises contacting the fluid sample with a lysing reagent;

separating one or more target nucleic acids from concomitant material;

amplifying the one or more target nucleic acids in presence of the microarray; and while one or more target nucleic acids is being amplified, determining a value indicative of the presence and/or amount of nucleic acids associated with a viral infection in the fluid sample by performing a microarray analysis in the device;

wherein the analysis performed in the device comprises forming complexes, each complex comprising a nucleic acid associated with a viral infection and a capture molecule, wherein each capture molecule comprises an anchor group and a binding portion specific to a region of the nucleic acid associated with a viral infection, contacting the complexes with a first binding member of the device, the first binding member being configured to bind the anchor group of the capture molecule to bind the complexes to the first binding member and providing an amount of a reporter compound capable of forming a complex with a nucleic acid associated with a viral infection, and a second binding member capable of capturing the reporter compound, the forming of complexes of the reporter compound with the nucleic acid inhibiting capturing of the reporter compound by the second binding member.

2. The method of claim 1, further comprising:

forming complexes of a subset of the amount of reporter compound with at least a subset of the amount of nucleic acid associated with a viral infection;

capturing a remaining subset of the amount of reporter compound not in complex with a nucleic acid associated with a viral infection on the second binding member; and determining a value indicative of the presence and/or amount of reporter compound captured on the second binding member; and, optionally, determining one or more values indicative of the amount of nucleic acids associated with a viral infection based on the values indicative of the amount of reporter compound.

3. The method of claim 2, wherein amplification of the one or more target nucleic acids is initiated prior to the step of forming complexes of a subset of the amount of reporter compound with at least a subset of the amount of nucleic acid.

4. The method of claim 1, wherein the device comprises a second structure adapted for accommodating liquids, configured for detecting the one or more target nucleic acids and containing the microarray, the second structure comprising a cover element covering the second structure, and an actuator unit adapted for being actuated to deform the cover element, and wherein determining the value indicative of the presence and/or the amount of nucleic acids is performed in the second structure.

5. The method of claim 1, wherein determining the value indicative for the presence and/or amount of nucleic acids comprises time-dependent monitoring of the indicative value.

* * * * *

SEQUENCE LISTING

```
<160> NUMBER OF SEQ ID NOS: 10

<210> SEQ ID NO 1
<211> LENGTH: 27
<212> TYPE: DNA
<213> ORGANISM: artificial
<220> FEATURE:
<223> OTHER INFORMATION: Primer

<400> SEQUENCE: 1
caaaccagtg attggcctgt cgtaacg                               27

<210> SEQ ID NO 2
<211> LENGTH: 25
<212> TYPE: DNA
<213> ORGANISM: artificial
<220> FEATURE:
<223> OTHER INFORMATION: Primer

<400> SEQUENCE: 2
ttcaccggat ggccaatcca attcg                                 25

<210> SEQ ID NO 3
<211> LENGTH: 26
<212> TYPE: DNA
<213> ORGANISM: artificial
<220> FEATURE:
<223> OTHER INFORMATION: Probe

<400> SEQUENCE: 3
accgactact ttgggtgtcc gtgttt                                26

<210> SEQ ID NO 4
<211> LENGTH: 26
<212> TYPE: DNA
<213> ORGANISM: artificial
<220> FEATURE:
<223> OTHER INFORMATION: Primer
```

```
<400> SEQUENCE: 4
accgactact ttgggtgtcc gtgttt                                          26

<210> SEQ ID NO 5
<211> LENGTH: 29
<212> TYPE: DNA
<213> ORGANISM: artificial
<220> FEATURE:
<223> OTHER INFORMATION: Primer

<400> SEQUENCE: 5
tgaagggtac tagtagttcc tgctatgtc                                       29

<210> SEQ ID NO 6
<211> LENGTH: 22
<212> TYPE: DNA
<213> ORGANISM: artificial
<220> FEATURE:
<223> OTHER INFORMATION: Primer

<400> SEQUENCE: 6
atcaagcagc catgcaaatg tt                                              22

<210> SEQ ID NO 7
<211> LENGTH: 151
<212> TYPE: DNA
<213> ORGANISM: artificial
<220> FEATURE:
<223> OTHER INFORMATION: Synthetic HIV1 gag/env fusion fragment

<400> SEQUENCE: 7
atcaagcagc catgcaaatg ttaaaagaga ccatcaatga ggaagctgca gaatgggata     60
gattgcatcc agtccatgga gggcctattg caccaggcca gatgagagaa ccaaggggaa    120
gtgacatagc aggaactact agtacccttc a                                   151

<210> SEQ ID NO 8
<211> LENGTH: 29
<212> TYPE: DNA
<213> ORGANISM: artificial
<220> FEATURE:
<223> OTHER INFORMATION: Reporter molecule

<400> SEQUENCE: 8
tcccattctg cagcttcctc attgatggt                                       29

<210> SEQ ID NO 9
<211> LENGTH: 20
<212> TYPE: DNA
<213> ORGANISM: artificial
<220> FEATURE:
<223> OTHER INFORMATION: Probe

<400> SEQUENCE: 9
accagctttg aacccaacac                                                 20

<210> SEQ ID NO 10
<211> LENGTH: 29
<212> TYPE: DNA
<213> ORGANISM: artificial
<220> FEATURE:
<223> OTHER INFORMATION: Probe
```

```
<400> SEQUENCE: 10
accatcaatg aggaagctgc agaatggga                                              29
```